United States Patent
Han et al.

(10) Patent No.: US 9,611,278 B2
(45) Date of Patent: Apr. 4, 2017

(54) SOLUBLE GUANYLATE CYCLASE ACTIVATORS

(71) Applicant: Merck Sharp & Dohme Corp., Rahway, NJ (US)

(72) Inventors: Xiaoqing Han, Edison, NJ (US); Alan Whitehead, Scotch Plains, NJ (US); Subharekha Raghavan, Teaneck, NJ (US); Jonathan Groeper, Indianapolis, IN (US); Jian Guo, Scotch Plains, NJ (US); Yong Zhang, West Windsor, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/103,140

(22) PCT Filed: Dec. 5, 2014

(86) PCT No.: PCT/US2014/068688
§ 371 (c)(1),
(2) Date: Jun. 9, 2016

(87) PCT Pub. No.: WO2015/088885
PCT Pub. Date: Jun. 18, 2015

(65) Prior Publication Data
US 2016/0304536 A1    Oct. 20, 2016

Related U.S. Application Data

(60) Provisional application No. 61/914,562, filed on Dec. 11, 2013.

(51) Int. Cl.
*A61K 31/519* (2006.01)
*A61K 31/52* (2006.01)
*A61K 45/06* (2006.01)
*C07D 519/00* (2006.01)

(52) U.S. Cl.
CPC .......... *C07D 519/00* (2013.01); *A61K 31/519* (2013.01); *A61K 31/52* (2013.01); *A61K 45/06* (2013.01)

(58) Field of Classification Search
None
See application file for complete search history.

(56) References Cited

U.S. PATENT DOCUMENTS

| | | |
|---|---|---|
| 3,211,732 A | 10/1965 | Schmidt et al. |
| 5,977,118 A | 11/1999 | Bacon et al. |
| 6,743,798 B1 | 6/2004 | Straub et al. |
| 7,173,037 B2 | 2/2007 | Alonso-Alija et al. |
| 8,420,656 B2 | 4/2013 | Follmann et al. |
| 8,455,638 B2 | 6/2013 | Bittner et al. |
| 8,507,512 B2 | 8/2013 | Kim et al. |
| 8,741,910 B2 | 6/2014 | Brockunier et al. |
| 8,859,569 B2 | 10/2014 | Follmann et al. |
| 8,895,583 B2 | 11/2014 | Tan et al. |
| 9,023,849 B2 | 5/2015 | Follmann et al. |
| 9,090,610 B2 | 7/2015 | Follmann et al. |
| 9,216,978 B2 | 12/2015 | Follmann et al. |
| 9,284,301 B2 | 3/2016 | Schmidt et al. |
| 9,365,574 B2 | 6/2016 | Raghavan et al. |
| 2003/0007992 A1 | 1/2003 | Gibson et al. |
| 2003/0114468 A1 | 6/2003 | Wilde et al. |
| 2011/0172216 A1 | 7/2011 | Dotson et al. |
| 2013/0072492 A1 | 3/2013 | Raghavan et al. |
| 2014/0171434 A1 | 6/2014 | Follmann et al. |
| 2014/0228366 A1 | 8/2014 | Follmann et al. |
| 2014/0357637 A1 | 12/2014 | Follmann et al. |
| 2016/0145272 A1 | 5/2016 | Berger et al. |

FOREIGN PATENT DOCUMENTS

| | | |
|---|---|---|
| WO | WO2012004258 | 1/2012 |
| WO | WO2015088886 A1 | 6/2015 |
| WO | WO2015187470 A1 | 12/2015 |

OTHER PUBLICATIONS

Follmann, N. et al., The Chemistry and Biology of Soluble Guanylate Cyclase Stimulators and Activators, Angewandte Chemie—International Edition, 2013, pp. 9442-9462, Vol. 52 Issue 36.
International Search Report and Written Opinion for PCT/US2014/068688, mailed Mar. 17, 2015, 12 pages.

*Primary Examiner* — Samantha Shterengarts
(74) *Attorney, Agent, or Firm* — Eric A Meade; Anna L. Cocuzzo

(57) ABSTRACT

A compound of Formula I or a pharmaceutically acceptable salt thereof, are capable of modulating the body's production of cyclic guanosine monophosphate ("cGMP") and are generally suitable for the therapy and prophylaxis of diseases which are associated with a disturbed cGMP balance. The invention furthermore relates to processes for preparing compounds of Formula I, or a pharmaceutically acceptable salt thereof, for their use in the therapy and prophylaxis of the abovementioned diseases and for preparing pharmaceuticals for this purpose, and to pharmaceutical preparations which comprise compounds of Formula I or a pharmaceutically acceptable salt thereof.

20 Claims, No Drawings

SOLUBLE GUANYLATE CYCLASE ACTIVATORS

CROSS-REFERENCE TO RELATED APPLICATIONS

This application is a U.S. National Phase application under 35 U.S.C. §371 of PCT/US2014/68688, filed Dec. 5, 2014, which claims priority from U.S. provisional application No. 61/914,562 filed Dec. 11, 2013.

BACKGROUND OF THE INVENTION

Cyclic GMP (cGMP) is an important intracellular messenger which triggers a multitude of different effects via the modulation of cGMP-dependent protein kinases, phosphodiesterases and ion channels. Examples are the relaxation of smooth muscles, the inhibition of thrombocyte activation and the inhibition of the proliferation of smooth-muscle cells and of leukocyte adhesion. cGMP is produced by particulate and soluble guanylate cyclases as a response to a number of extracellular and intracellular stimuli. In the case of the particulate guanylate cyclases, stimulation is essentially effected by peptidic messengers, such as the atrial natriuretic peptide or the cerebral natriuretic peptide. The soluble guanylate cyclases ("sGC"), which are cytosolic heterodimeric heme proteins, in contrast, are essentially regulated by a family of low-molecular-weight factors which are formed enzymatically. The most important stimulant is nitrogen monoxide ("NO") or a closely related species. The function of other factors such as carbon monoxide or the hydroxyl radical is still largely unclear. The binding of NO to the heme with formation of a penta-coordinate heme-nitrosyl complex is proposed as the mechanism of the activation by NO. The associated release of the histidine which is bound in the basal state to the iron converts the enzyme into the active conformation.

Active soluble guanylate cyclases are each composed of an α and a β subunit. Several subunit subtypes have been described which differ from one another with respect to sequence, tissue-specific distribution and expression in different development stages. The subtypes $α_1$ and $β_1$ are mainly expressed in brain and lung, while $β_2$ is found in particular in liver and kidney. The subtype $α_2$ was shown to be present in human fetal brain. The subunits referred to as $α_3$ and $β_3$ were isolated from human brain and are homologous to $α_1$ and $β_1$. More recent works indicate an $α_{2i}$ subunit which contains an insert in the catalytic domain. All subunits show great homologies in the region of the catalytic domain. The enzymes presumably contain one heme per heterodimer, which is bound via $β_1$-Cys-78 and/or $β_1$-His-105 and is part of the regulatory center.

Under pathologic conditions, the formation of guanylate-cyclase-activating factors can be reduced, or their degradation may be promoted owing to the increased occurrence of free radicals. The resulting reduced activation of the sGC leads, via a weakening of the respective cGMP-mediated cellular response, for example to an increase of the blood pressure, to platelet activation or to increased cell proliferation and cell adhesion. As a consequence, formation of endothelial dysfunction, atherosclerosis, hypertension, stable or unstable angina pectoris, thrombosis, myocardial infarction, strokes or erectile dysfunction results. Pharmacological stimulation of sGC offers a possibility to normalize cGMP production and therefore makes possible the treatment and/or prevention of such disorders.

For the pharmacological stimulation of the sGC, use has been made of compounds whose activity is based on an intermediate NO release, for example organic nitrates. The drawback of this treatment is the development of tolerance and a reduction of activity, and the higher dosage which is required because of this.

Various sGC stimulators which do not act via NO release were described by Vesely in a series of publications. However, the compounds, most of which are hormones, plant hormones, vitamins or natural compounds such as, for example, lizard poisons, predominantly only have weak effects on the cGMP formation in cell lysates. D. L. Vesely, Eur. J. Clin. Invest., vol. 15, 1985, p. 258; D. L. Vesely, Biochem. Biophys. Res. Comm., vol. 88, 1979, p. 1244. A stimulation of heme-free guanylate cyclase by protoporphyrin IX was demonstrated by Ignarro et al., Adv. Pharmacol., vol. 26, 1994, p. 35. Pettibone et al., Eur. J. Pharmacol., vol. 116, 1985 p. 307, described an antihypertensive action of diphenyliodonium hexafluorophosphate and attributed this to a stimulation of sGC. According to Yu et al., Brit. J. Pharmacol, vol. 114, 1995, p. 1587, isoliquiritigenin, which has a relaxing action on isolated rat aortas, also activates sGC. Ko et al., Blood vol. 84, 1994, p. 4226, Yu et al., Biochem. J. vol. 306, 1995, p. 787, and Wu et al., Brit. J. Pharmacol. vol. 116, 1995, p. 1973, demonstrated a sGC-stimulating activity of 1-benzyl-3-(5-hydroxymethyl-2-furyl)indazole and demonstrated an antiproliferative and thrombocyte-inhibiting action. Pyrazoles and fused pyrazoles which exhibit a sGC-stimulating activity are described in European Patent Application No. 908,456 and German Patent Application No. 19,744,027.

A series of 2-sulfonylaminobenzoic acid N-arylamides, the N-aryl group of which carries a thio substituent, have been mentioned in the literature. These compounds in which the N-aryl group generally carries as further substituents groups which are readily oxidizable such as, for example, two hydroxy groups being in para position with respect to one another and which in this case can be regarded as hydroquinone derivatives, are auxiliaries for the preparation of photographic materials (see, for example, Chemical Abstracts 119, 105757; 120, 41858; 123, 70224; or 126, 257007). British patent publication No. 876,526 (Chemical Abstracts 56, 15432e) discloses 3,5-dichloro-2-methylsulfonylaminobenzoic acid N-(5-chloro-2-(4-chlorophenylmercapto)-phenyl)-amide which can be used for the protection of wool against moths.

It has now been found that the compounds of the present invention effect a strong activation of guanylate cyclase and are therefore suitable for the therapy and prophylaxis of disorders which are associated with a low cGMP level.

SUMMARY OF THE INVENTION

The present invention relates to compounds which activate soluble guanylate cyclase and are valuable pharmaceutically active compounds for the therapy and prophylaxis of diseases, for example for cardiovascular diseases such as hypertension, heart failure, pulmonary hypertension, angina pectoris, diabetes, cardiac insufficiency, thrombosis, chronic kidney disease or atherosclerosis. The compounds of Formula I

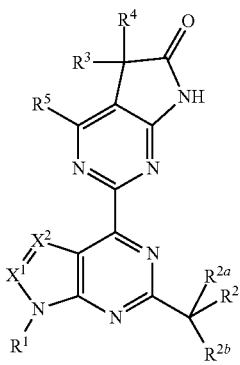

are capable of modulating the body's production of cyclic guanosine monophosphate ("cGMP") and are generally suitable for the therapy and prophylaxis of diseases which are associated with a disturbed cGMP balance. The invention furthermore relates to processes for preparing compounds of Formula I, to their use for the therapy and prophylaxis of the abovementioned diseases and for preparing pharmaceuticals for this purpose, and to pharmaceutical preparations which comprise compounds of Formula I.

DETAILED DESCRIPTION OF THE INVENTION

The present invention is directed to compounds having structural Formula I:

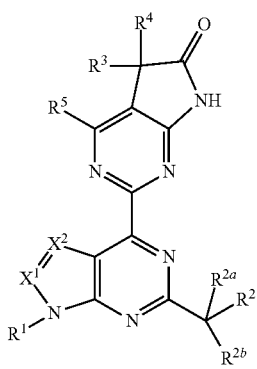

I or a pharmaceutically acceptable salt thereof wherein:
$X^1$ and $X^2$ are each independently CR or N;
R is —H, halo or cyclopropyl;
$R^1$ is —H or —$C_{1-6}$alkyl unsubstituted or substituted with one to three of —F;
$R^2$ is (a) —$C_{1-6}$alkyl unsubstituted or substituted with:
  (i) one to six of —F,
  (ii) —$C_{3-6}$cycloalkyl unsubstituted or substituted with one to three of —F, or
  (iii) phenyl unsubstituted or independently substituted at each occurrence with one to three of halo, —CN, —$CH_3$ or —$OCH_3$;
(b) —$C_{3-6}$cycloalkyl unsubstituted or substituted with one to three of —F, or
(c) phenyl unsubstituted or independently substituted at each occurrence with one to three of halo, —CN, —$CH_3$ or —$OCH_3$;

$R^{2a}$ is —H or —$C_{1-3}$alkyl unsubstituted or substituted with one to three of —F;
$R^{2b}$ is —H or —$C_{1-3}$alkyl unsubstituted or substituted with one to three of —F;
or $R^{2b}$ is —H and $R^2$ and $R^{2a}$ are joined together with the carbon to which they are both attached to represent
  (a) —$C_{3-6}$cycloalkyl unsubstituted or substituted with one to three of —F, or
  (b) a 4 to 6 membered heterocycle comprised of carbons and one or two heteroatoms independently selected from N, O or S, wherein the heterocycle is unsubstituted or independently substituted at each occurrence with one to three of halo, —CN, —$CH_3$ or —$OCH_3$;
$R^3$ is —$C_{1-6}$alkyl or —$C_{3-6}$cycloalkyl;
$R^4$ is
  (a) a 5-membered heteroaryl ring comprised of at least one and up to three carbon atoms, at least one and up to four N atoms, and optionally one O atom or one S atom;
  (b) a 6-membered heteroaryl ring comprised of carbon atoms and one or two N atoms; or
  (c) an 8 to 10 membered bicyclic heteroaryl ring system comprised of carbon atoms and one to two heteroatoms independently selected from N, O or S;
wherein $R^4$ is unsubstituted or substituted on an available carbon or nitrogen in the ring or ring system with $R^6$;
$R^6$ is selected from:
  (a) halo,
  (b) —$C_{1-6}$alkyl unsubstituted or substituted with one to three of —F, or —$C_{3-6}$ cycloalkyl for example but not limited to:

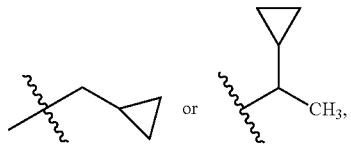 [SMILES: *CC1CC1 ; *C(C)C1CC1]

(c) —$C_{1-6}$alkyl substituted with —$C_{3-6}$ cycloalkyl, such that the cycloalkyl and the alkyl share a common carbon at the point of attachment to each other, wherein said attachment can be with any non-terminal carbon in the alkyl group, for example but not limited to:

(d) —$C_{3-6}$ cycloalkyl,
  (e) —$OC_{1-6}$alkyl,
  (f) —$C_{2-6}$alkenyl,
  (g) —$C(O)OC_{1-4}$alkyl,
  (h) —$C_{1-6}$alkyl-$C(O)OH$,
  (i) —$C_{1-6}$alkyl-$C(O)OC_{1-3}$alkyl, or
  (j) -$CD_3$;
$R^5$ is —H, —$OR^7$ or —$NHR^7$; and
$R^7$ is —H, —$C_{1-6}$alkyl or —$C_{3-6}$ cycloalkyl.
In an embodiment of this invention are compounds of Formula I having structural Formula Ia:

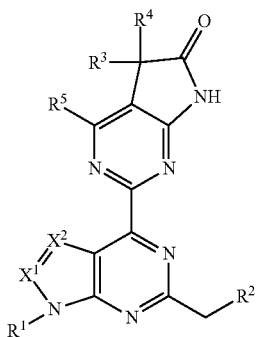

wherein all variables including $R^1$, $R^2$, $R^3$, $R^4$, $R^5$, $X^1$ and $X^2$ are as defined in Formula I.

In an embodiment of this invention are compounds of Formula I having structural Formula Ib:

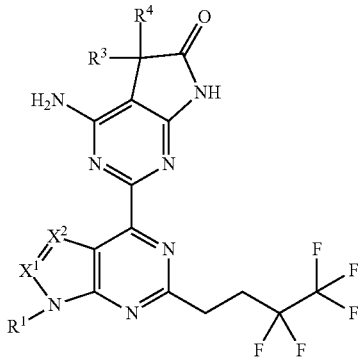

wherein all variables including $R^1$, $R^3$, $R^4$, $X^1$ and $X^2$ are as defined in Formula I.

In another embodiment of this invention, which is referred to as Embodiment 1 herein, are compounds of Formula I or Formula Ia wherein:
$X^1$ and $X^2$ are each independently CH or N;
$R^1$ is —H or —$C_{1-3}$alkyl; and
$R^3$ is —$C_{1-6}$alkyl or —$C_{3-6}$cycloalkyl;
wherein all other variables, including $R^2$, $R^4$ and $R^5$, are as defined in Formula I.

In another embodiment of this invention are compounds of Formula I, Formula Ia, Formula Ib or Embodiment 1 wherein $X^1$ and $X^2$ are both N. In another embodiment, $X^1$ and $X^2$ are both CR in Formula I, Formula Ia or Formula Ib; or $X^1$ and $X^2$ are both CH in Formula I, Formula Ia, Formula Ib or Embodiment 1. In another embodiment, $X^1$ is N and $X^2$ is CR in Formula I, Formula Ia or Formula Ib; or $X^1$ is N and $X^2$ is CH in Formula I, Formula Ia, Formula Ib or Embodiment 1.

In another embodiment of this invention are compounds of Formula I, Formula Ia, Formula Ib or Embodiment 1 wherein $R^1$ is —H or —$C_{1-3}$alkyl unsubstituted or substituted with one to three of —F; particularly it is —H, —$CH_3$, -$CD_3$, —$CH_2CH_3$ or -$CD_2CD_3$; and more particularly it is —$CH_3$ or -$CD_3$.

In another embodiment of this invention are compounds of Formula I, Formula Ia or Embodiment 1 wherein $R^2$ is unsubstituted —$C_{1-6}$alkyl, unsubstituted —$C_{3-6}$cycloalkyl or unsubstituted phenyl. In an alternate embodiment $R^2$ is (a) —$C_{1-6}$alkyl substituted with
   (i) one to six of —F,
   (ii) —$C_{3-6}$cycloalkyl substituted with one to three of —F; or
   (iii) phenyl independently substituted at each occurrence with one to three of halo, —CN, —$CH_3$ or —$OCH_3$,
(b) —$C_{3-6}$cycloallkyl substituted with one to three of —F, or
(c) phenyl independently substituted at each occurrence with one to three of -halo, —CN, —$CH_3$ or —$OCH_3$.

Particularly, $R^2$ can be —$C_{1-5}$alkyl-$CF_3$, —$C_{1-4}$alkyl-$CF_3$, —$C_{1-3}$alkyl-$CF_3$, or —$C_{1-2}$alkyl-$CF_3$, wherein each group is unsubstituted or substituted with one to three of —F on one or more available carbons. Alternatively, $R^2$ can be —$C_{3-6}$cycloalkyl or —$C_{1-3}$alkyl-$C_{3-6}$cycloalkyl wherein a carbon in the cycloalkyl ring is di-substituted with —F, for example but no limited to:

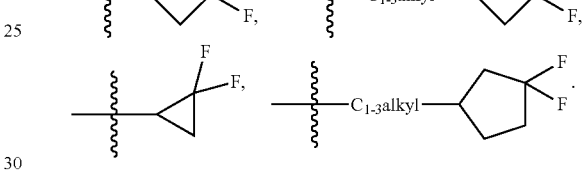

Alternatively, $R^2$ can be -phenyl or —$C_{1-3}$alkyl-phenyl, wherein each phenyl is substituted with one to three of —F.

In another embodiment of this invention are compounds of Formula I, Formula Ia, Formula Ib or Embodiment 1 wherein $R^3$ is —$C_{1-6}$alkyl or —$C_{3-6}$cycloalkyl, and particularly it is —$C_{1-3}$alkyl or cyclopropyl.

In another embodiment of this invention are compounds of Formula I, Formula Ia, Formula Ib or Embodiment 1 wherein $R^4$ is a 5-membered heteroaryl ring selected from:

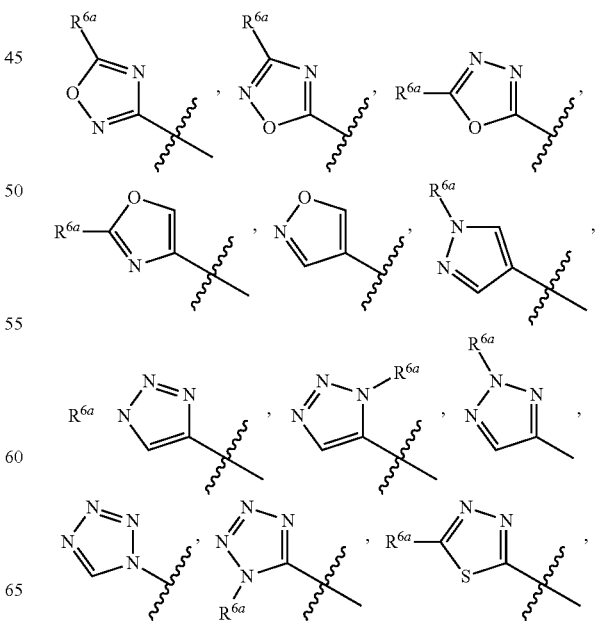

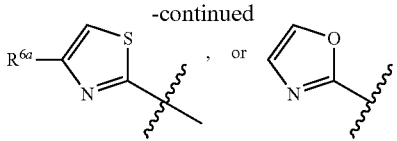, or and $R^{6a}$ is —H or $R^6$.

In another embodiment of this invention are compounds of Formula I, Formula Ia, Formula Ib or Embodiment 1 wherein $R^4$ is a 6-membered heteroaryl ring selected from:

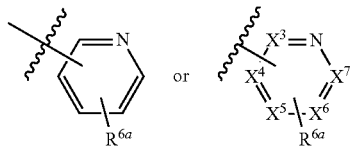

wherein one of $X^3$, $X^4$, $X^5$, $X^6$ or $X^7$ is N and the others are CH; and $R^{6a}$ is —H or $R^6$.

In another embodiment of this invention are compounds of Formula I, Formula Ia, Formula Ib or Embodiment 1 wherein $R^4$ is an 8 to 10 membered bicyclic heteroaryl comprised of carbon atoms and one to two heteroatoms independently selected from N, O or S and particularly selected from N and O. More particularly, $R^4$ is a bicyclic heteroaryl ring system selected from:

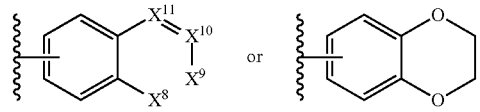 or wherein one or two of $X^8$, $X^9$, $X^{10}$ or $X^{11}$ is N and the others are CH.

In another embodiment of this invention are compounds of Formula I, Formula Ia or Embodiment 1 wherein $R^5$ it is —H, —OH or —NH$_2$, and more particularly it is —NH$_2$.

In another embodiment of this invention are compounds of Formula I, Formula Ia, Formula Ib or Embodiment 1 wherein $R^6$ is (a) —F or —Cl, (b) —C$_{1-6}$alkyl or more particularly —C$_{1-4}$alkyl, (c) —CF$_3$, (d) —CH$_2$—C$_{3-6}$cycloalkyl or more particularly —CH$_2$—C$_{3-4}$cycloalkyl, (e) —C$_{1-3}$alkyl substituted with —C$_{3-4}$ cycloalkyl such that the cycloalkyl and the alkyl share a common carbon at the point of attachment to each other, (f) —C$_{3-6}$cycloalkyl or more particularly —C$_{3-4}$cycloalkyl, (g) —OC$_{1-6}$alkyl or more particularly —OC$_{1-4}$alkyl, (h) —C$_{2-4}$alkenyl, (i) —C(O)OC$_{1-4}$alkyl, (j) —C$_{1-4}$alkyl-C(O)OH, (k) —C$_{1-4}$alkyl-C(O)OCH$_3$, or (l) -CD$_3$.

In another embodiment of this invention are each of the following compounds of Formula I, including the S and R enantiomers of such compounds, and the pharmaceutically acceptable salts of each said compound:

| EX | Compound Name |
|---|---|
| 1 | 4-Amino-5-(5-fluoropyridin-2-yl)-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one; |
| 2 | 4-Amino-5-(4-fluorophenyl)-5-methyl-2-(6-(3,3,4,4,4-pentafluorobutyl)-1-(methyl-d3)-1H-pyrazolo[3,4-d]pyrimidin-4-yl)-5H-pyrrolo[2,3-d]pyrimidin-6(7H)-one; |
| 3 | 4-Amino-2-(6-((3,3-difluorocyclobutyl)methyl)-1-methyl-1H-pyrazolo[3,4-d]pyrimidin-4-yl)-5-(5-fluoropyridin-2-yl)-5-methyl-5,7-dihydro-6H-pyrrolo[2,3-d]pyrimidin-6-one; |
| 4 | 4-Amino-5-(5-fluoropyridin-2-yl)-5-methyl-2-(1-methyl-6-(4,4,4-trifluorobutyl)-1H-pyrazolo[3,4-d]pyrimidin-4-yl)-5H-pyrrolo[2,3-d]pyrimidin-6(7H)-one; |
| 5 | 4-Amino-2-(6-(2,3-difluorobenzyl)-1-methyl-1H-pyrazolo[3,4-d]pyrimidin-4-yl)-5-methyl-5-(3-methyl-1,2,4-oxadiazol-5-yl)-5,7-dihydro-6H-pyrrolo[2,3-d]pyrimidin-6-one; |
| 6 | 4-Amino-5-(5-fluoropyridin-2-yl)-5-methyl-2-(1-methyl-6-(4,4,4-trifluorobutan-2-yl)-1H-pyrazolo[3,4-d]pyrimidin-4-yl)-5,7-dihydro-6H-pyrrolo[2,3-d]pyrimidin-6-one; |
| 7 | 4-Amino-5-methyl-2-(1-(methyl-d3)-6-(3,3,4,4,4-pentafluorobutyl)-1H-pyrazolo[3,4-d]pyrimidin-4-yl)-5-(pyridin-2-yl)-5,7-dihydro-6H-pyrrolo[2,3-d]pyrimidin-6-one; |
| 8 | 4-Amino-5-(3-cyclopropyl-1,2,4-oxadiazol-5-yl)-5-methyl-2-(1-(methyl-d3)-6-(3,3,4,4,4-pentafluorobutyl)-1H-pyrazolo[3,4-d]pyrimidin-4-yl)-5,7-dihydro-6H-pyrrolo[2,3-d]pyrimidin-6-one; |
| 9 | 4-Amino-5-methyl-2-(1-(methyl-d3)-6-(3,3,4,4,4-pentafluorobutyl)-1H-pyrazolo[3,4-d]pyrimidin-4-yl)-5-(pyrimidin-2-yl)-5,7-dihydro-6H-pyrrolo[2,3-d]pyrimidin-6-one; |
| 10 | 4-Amino-5-methyl-2-(1-(methyl-d3)-6-(3,3,4,4,4-pentafluorobutyl)-1H-pyrazolo[3,4-d]pyrimidin-4-yl)-5-(6-(trifluoromethyl)pyridin-3-yl)-5,7-dihydro-6H-pyrrolo[2,3-d]pyrimidin-6-one; |
| 11 | 4-Amino-5-methyl-2-(1-(methyl-d3)-6-(3,3,4,4,4-pentafluorobutyl)-1H-pyrazolo[3,4-d]pyrimidin-4-yl)-5-(2-methyloxazol-4-yl)-5,7-dihydro-6H-pyrrolo[2,3-d]pyrimidin-6-one; |
| 12 | 4-Amino-5-(5-methoxypyridin-2-yl)-5-methyl-2-(1-(methyl-d3)-6-(3,3,4,4,4-pentafluorobutyl)-1H-pyrazolo[3,4-d]pyrimidin-4-yl)-5,7-dihydro-6H-pyrrolo[2,3-d]pyrimidin-6-one; |
| 13 | 4-Amino-5-methyl-2-(1-(methyl-d3)-6-(3,3,4,4,4-pentafluorobutyl)-1H-pyrazolo[3,4-d]pyrimidin-4-yl)-5-(quinolin-7-yl)-5,7-dihydro-6H-pyrrolo[2,3-d]pyrimidin-6-one; |
| 14 | 4-Amino-5-(5-methoxypyridin-3-yl)-5-methyl-2-(1-(methyl-d3)-6-(3,3,4,4,4-pentafluorobutyl)-1H-pyrazolo[3,4-d]pyrimidin-4-yl)-5,7-dihydro-6H-pyrrolo[2,3-d]pyrimidin-6-one; |
| 15 | 4-Amino-5-cyclopropyl-5-(1-methyl-1H-pyrazol-4-yl)-2-(1-methyl-6-(3,3,4,4,4-pentafluorobutyl)-1H-pyrazolo[3,4-d]pyrimidin-4-yl)-5,7-dihydro-6H-pyrrolo[2,3-d]pyrimidin-6-one; |
| 16 | 4-Amino-5-cyclopropyl-5-(isoxazol-4-yl)-2-(1-methyl-6-(3,3,4,4,4-pentafluorobutyl)-1H-pyrazolo[3,4-d]pyrimidin-4-yl)-5,7-dihydro-6H-pyrrolo[2,3-d]pyrimidin-6-one; |
| 17 | 4-Amino-5-ethyl-5-(6-methoxypyridin-3-yl)-2-(1-methyl-6-(3,3,4,4,4-pentafluorobutyl)-1H-pyrazolo[3,4-d]pyrimidin-4-yl)-5,7-dihydro-6H-pyrrolo[2,3-d]pyrimidin-6-one; |

| EX | Compound Name |
|---|---|
| 18 | Methyl 4-(4-amino-5-methyl-2-(1-(methyl-d3)-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidin-5-yl)picolinate; |
| 19 | 4-Amino-5-methyl-5-(5-methyl-1,2,4-oxadiazol-3-yl)-2-(1-(methyl-d3)-6-(3,3,4,4,4-pentafluorobutyl)-1H-pyrazolo[3,4-d]pyrimidin-4-yl)-5,7-dihydro-6H-pyrrolo[2,3-d]pyrimidin-6-one; |
| 20 | 4-Amino-5-methyl-5-(5-methyl-1,2,4-oxadiazol-3-yl)-2-(1-methyl-6-(3,3,4,4,4-pentafluorobutyl)-1H-pyrazolo[3,4-d]pyrimidin-4-yl)-5,7-dihydro-6H-pyrrolo[2,3-d]pyrimidin-6-one; |
| 21 | 4-Amino-5-methyl-2-(1-methyl-6-(4,4,4-trifluorobutyl)-1H-pyrazolo[3,4-d]pyrimidin-4-yl)-5-(pyridin-2-yl)-5,7-dihydro-6H-pyrrolo[2,3-d]pyrimidin-6-one; |
| 22 | 4-Amino-5-methyl-2-(1-methyl-6-(3,3,4,4,4-pentafluorobutyl)-1H-pyrazolo[3,4-d]pyrimidin-4-yl)-5-(pyridin-2-yl)-5,7-dihydro-6H-pyrrolo[2,3-d]pyrimidin-6-one; |
| 23 | 4-Amino-5-methyl-5-(1-methyl-1H-pyrazol-4-yl)-2-(1-methyl-6-(3,3,4,4,4-pentafluorobutyl)-1H-pyrazolo[3,4-d]pyrimidin-4-yl)-5,7-dihydro-6H-pyrrolo[2,3-d]pyrimidin-6-one; |
| 24 | 4-Amino-5-cyclopropyl-5-(1-methyl-1H-pyrazol-4-yl)-2-(1-(methyl-d3)-6-(3,3,4,4,4-pentafluorobutyl)-1H-pyrazolo[3,4-d]pyrimidin-4-yl)-5,7-dihydro-6H-pyrrolo[2,3-d]pyrimidin-6-one; |
| 25 | 4-Amino-5-cyclopropyl-5-(1-methyl-1H-tetrazol-5-yl)-2-(1-(methyl-d3)-6-(3,3,4,4,4-pentafluorobutyl)-1H-pyrazolo[3,4-d]pyrimidin-4-yl)-5,7-dihydro-6H-pyrrolo[2,3-d]pyrimidin-6-one; |
| 26 | 4-Amino-5-cyclopropyl-5-(1-isopropyl-1H-pyrazol-4-yl)-2-(1-methyl-6-(3,3,4,4,4-pentafluorobutyl)-1H-pyrazolo[3,4-d]pyrimidin-4-yl)-5,7-dihydro-6H-pyrrolo[2,3-d]pyrimidin-6-one; |
| 27 | 4-Amino-5-methyl-5-(5-methyl-1,3,4-thiadiazol-2-yl)-2-(1-methyl-6-(3,3,4,4,4-pentafluorobutyl)-1H-pyrazolo[3,4-d]pyrimidin-4-yl)-5,7-dihydro-6H-pyrrolo[2,3-d]pyrimidin-6-one; |
| 28 | 4-Amino-5-cyclopropyl-2-(1-methyl-6-(3,3,4,4,4-pentafluorobutyl)-1H-pyrazolo[3,4-d]pyrimidin-4-yl)-5-(oxazol-2-yl)-5,7-dihydro-6H-pyrrolo[2,3-d]pyrimidin-6-one; |
| 29 | 4-Amino-2-(6-(2-(3,3-difluorocyclobutyl)ethyl)-1-methyl-1H-pyrazolo[3,4-d]pyrimidin-4-yl)-5-(5-fluoropyridin-2-yl)-5-methyl-5,7-dihydro-6H-pyrrolo[2,3-d]pyrimidin-6-one; |
| 30 | 4-Amino-2-(6-(2-cyclobutylethyl)-1-methyl-1H-pyrazolo[3,4-d]pyrimidin-4-yl)-5-(5-fluoropyridin-2-yl)-5-methyl-5,7-dihydro-6H-pyrrolo[2,3-d]pyrimidin-6-one; |
| 31 | 4-Amino-5-(5-chloropyridin-2-yl)-5-cyclopropyl-2-(6-((3,3-difluorocyclobutyl)methyl)-1-methyl-1H-pyrazolo[3,4-d]pyrimidin-4-yl)-5,7-dihydro-6H-pyrrolo[2,3-d]pyrimidin-6-one; |
| 32 | 4-Amino-5-cyclopropyl-2-(6-((3,3-difluorocyclobutyl)methyl)-1-methyl-1H-pyrazolo[3,4-d]pyrimidin-4-yl)-5-(5-(trifluoromethyl)pyridin-2-yl)-5,7-dihydro-6H-pyrrolo[2,3-d]pyrimidin-6-one; |
| 33 | 4-Amino-2-(6-((3,3-difluorocyclobutyl)methyl)-1-methyl-1H-pyrazolo[3,4-d]pyrimidin-4-yl)-5-(5-methoxypyridin-2-yl)-5-methyl-5,7-dihydro-6H-pyrrolo[2,3-d]pyrimidin-6-one; |
| 34 | 4-Amino-2-(6-butyl-1-methyl-1H-pyrazolo[3,4-d]pyrimidin-4-yl)-5-(5-fluoropyridin-2-yl)-5-methyl-5,7-dihydro-6H-pyrrolo[2,3-d]pyrimidin-6-one; |
| 35 | 4-Amino-2-(6-butyl-1-methyl-1H-pyrazolo[3,4-d]pyrimidin-4-yl)-5-(5-isopropylpyridin-2-yl)-5-methyl-5,7-dihydro-6H-pyrrolo[2,3-d]pyrimidin-6-one; |
| 36 | 4-Amino-2-(6-butyl-1-methyl-1H-pyrazolo[3,4-d]pyrimidin-4-yl)-5-(5-methoxypyridin-2-yl)-5-methyl-5,7-dihydro-6H-pyrrolo[2,3-d]pyrimidin-6-one; |
| 37 | 4-Amino-5-(5-chloropyridin-2-yl)-2-(6-((3,3-difluorocyclobutyl)methyl)-1-methyl-1H-pyrazolo[3,4-d]pyrimidin-4-yl)-5-methyl-5,7-dihydro-6H-pyrrolo[2,3-d]pyrimidin-6-one; |
| 38 | 4-Amino-5-cyclopropyl-5-(5-cyclopropyl-1,3,4-oxadiazol-2-yl)-2-(1-(methyl-d3)-6-(3,3,4,4,4-pentafluorobutyl)-1H-pyrazolo[3,4-d]pyrimidin-4-yl)-5,7-dihydro-6H-pyrrolo[2,3-d]pyrimidin-6-one; |
| 39 | 4-Amino-5-(5-cyclopropyl-1,3,4-oxadiazol-2-yl)-5-methyl-2-(1-(methyl-d3)-6-(3,3,4,4,4-pentafluorobutyl)-1H-pyrazolo[3,4-d]pyrimidin-4-yl)-5,7-dihydro-6H-pyrrolo[2,3-d]pyrimidin-6-one; |
| 40A | 4-Amino-5-cyclopropyl-5-(5-methyl-1,3,4-oxadiazol-2-yl)-2-(1-(methyl-d3)-6-(3,3,4,4,4-pentafluorobutyl)-1H-pyrazolo[3,4-d]pyrimidin-4-yl)-5,7-dihydro-6H-pyrrolo[2,3-d]pyrimidin-6-one; |
| 40B | 4-Amino-5-cyclopropyl-5-(5-methyl-1,3,4-oxadiazol-2-yl)-2-(1-(methyl-d3)-6-(3,3,4,4,4-pentafluorobutyl)-1H-pyrazolo[3,4-d]pyrimidin-4-yl)-5,7-dihydro-6H-pyrrolo[2,3-d]pyrimidin-6-one; |
| 42 | 4-Amino-5-(5-cyclopropyl-1,3,4-oxadiazol-2-yl)-5-ethyl-2-(1-(methyl-d3)-6-(3,3,4,4,4-pentafluorobutyl)-1H-pyrazolo[3,4-d]pyrimidin-4-yl)-5,7-dihydro-6H-pyrrolo[2,3-d]pyrimidin-6-one; |
| 43 | 4-Amino-5-cyclopropyl-5-(5-cyclopropyl-1,3,4-oxadiazol-2-yl)-2-(1-(methyl-d3)-6-(4,4,4-trifluorobutyl)-1H-pyrazolo[3,4-d]pyrimidin-4-yl)-5,7-dihydro-6H-pyrrolo[2,3-d]pyrimidin-6-one; |
| 44 | 4-Amino-5-cyclopropyl-5-(5-cyclopropyl-1,3,4-oxadiazol-2-yl)-2-(1-methyl-6-(3,3,4,4,4-pentafluorobutyl)-1H-pyrazolo[3,4-d]pyrimidin-4-yl)-5,7-dihydro-6H-pyrrolo[2,3-d]pyrimidin-6-one; |
| 45 | 4-Amino-5-cyclopropyl-5-(5-cyclopropyl-1,3,4-oxadiazol-2-yl)-2-(1-ethyl-6-(3,3,4,4,4-pentafluorobutyl)-1H-pyrazolo[3,4-d]pyrimidin-4-yl)-5,7-dihydro-6H-pyrrolo[2,3-d]pyrimidin-6-one; |
| 46 | 4-Amino-5-(5-cyclobutyl-1,3,4-oxadiazol-2-yl)-5-cyclopropyl-2-(1-(methyl-d3)-6-(3,3,4,4,4-pentafluorobutyl)-1H-pyrazolo[3,4-d]pyrimidin-4-yl)-5,7-dihydro-6H-pyrrolo[2,3-d]pyrimidin-6-one; |

| EX | Compound Name |
|---|---|
| 47 | 4-Amino-5-cyclopropyl-5-(5-cyclopropyl-1,3,4-oxadiazol-2-yl)-2-(1-(methyl-d3)-6-(3,3,3-trifluoropropyl)-1H-pyrazolo[3,4-d]pyrimidin-4-yl)-5,7-dihydro-6H-pyrrolo[2,3-d]pyrimidin-6-one; |
| 48 | 4-Amino-5-cyclopropyl-2-(1-methyl-6-(3,3,4,4-pentafluorobutyl)-1H-pyrazolo[3,4-d]pyrimidin-4-yl)-5-(5-(1-methylcyclopropyl)-1,3,4-oxadiazol-2-yl)-5,7-dihydro-6H-pyrrolo[2,3-d]pyrimidin-6-one; |
| 49 | 4-Amino-5-cyclopropyl-5-(5-isopropyl-1,3,4-oxadiazol-2-yl)-2-(1-methyl-6-(3,3,4,4-pentafluorobutyl)-1H-pyrazolo[3,4-d]pyrimidin-4-yl)-5,7-dihydro-6H-pyrrolo[2,3-d]pyrimidin-6-one; |
| 50 | 4-Amino-5-(5-isopropyl-1,3,4-oxadiazol-2-yl)-5-methyl-2-(1-methyl-6-(3,3,4,4-pentafluorobutyl)-1H-pyrazolo[3,4-d]pyrimidin-4-yl)-5,7-dihydro-6H-pyrrolo[2,3-d]pyrimidin-6-one; |
| 51 | 4-Amino-5-cyclopropyl-5-(5-cyclopropyl-1,3,4-oxadiazol-2-yl)-2-(6-((3,3-difluorocyclobutyl)methyl)-1-methyl-1H-pyrazolo[3,4-d]pyrimidin-4-yl)-5,7-dihydro-6H-pyrrolo[2,3-d]pyrimidin-6-one; |
| 52 | 4-Amino-5-cyclopropyl-2-(6-((3,3-difluorocyclobutyl)methyl)-1-methyl-1H-pyrazolo[3,4-d]pyrimidin-4-yl)-5-(5-ethyl-1,3,4-oxadiazol-2-yl)-5,7-dihydro-6H-pyrrolo[2,3-d]pyrimidin-6-one; |
| 53 | 4-Amino-5-(5-cyclopropyl-1,3,4-oxadiazol-2-yl)-5-ethyl-2-(1-methyl-6-(3,3,4,4-pentafluorobutyl)-1H-pyrazolo[3,4-d]pyrimidin-4-yl)-5,7-dihydro-6H-pyrrolo[2,3-d]pyrimidin-6-one; |
| 54 | 4-Amino-5-cyclopropyl-5-(1-methyl-1H-1,2,3-triazol-4-yl)-2-(1-(methyl-d3)-6-(3,3,4,4-pentafluorobutyl)-1H-pyrazolo[3,4-d]pyrimidin-4-yl)-5,7-dihydro-6H-pyrrolo[2,3-d]pyrimidin-6-one; |
| 55 | 4-Amino-5-cyclopropyl-5-(1-methyl-1H-1,2,3-triazol-4-yl)-2-(1-methyl-6-(3,3,4,4-pentafluorobutyl)-1H-pyrazolo[3,4-d]pyrimidin-4-yl)-5,7-dihydro-6H-pyrrolo[2,3-d]pyrimidin-6-one; |
| 56 | 4-Amino-5-(1-isopropyl-1H-1,2,3-triazol-4-yl)-5-methyl-2-(1-methyl-6-(3,3,4,4-pentafluorobutyl)-1H-pyrazolo[3,4-d]pyrimidin-4-yl)-5,7-dihydro-6H-pyrrolo[2,3-d]pyrimidin-6-one; |
| 57 | 4-Amino-5-(1-isopropyl-1H-1,2,3-triazol-4-yl)-5-methyl-2-(1-(methyl-d3)-6-(3,3,4,4-pentafluorobutyl)-1H-pyrazolo[3,4-d]pyrimidin-4-yl)-5,7-dihydro-6H-pyrrolo[2,3-d]pyrimidin-6-one; |
| 58 | 4-Amino-5-ethyl-5-(1-methyl-1H-1,2,3-triazol-4-yl)-2-(1-methyl-6-(3,3,4,4-pentafluorobutyl)-1H-pyrazolo[3,4-d]pyrimidin-4-yl)-5,7-dihydro-6H-pyrrolo[2,3-d]pyrimidin-6-one; |
| 59 | 4-Amino-5-(1-cyclopropyl-1H-1,2,3-triazol-4-yl)-5-methyl-2-(1-methyl-6-(3,3,4,4-pentafluorobutyl)-1H-pyrazolo[3,4-d]pyrimidin-4-yl)-5,7-dihydro-6H-pyrrolo[2,3-d]pyrimidin-6-one; |
| 60 | 4-Amino-5-methyl-2-(1-methyl-6-(3,3,4,4-pentafluorobutyl)-1H-pyrazolo[3,4-d]pyrimidin-4-yl)-5-(1H-1,2,3-triazol-4-yl)-5,7-dihydro-6H-pyrrolo[2,3-d]pyrimidin-6-one; |
| 61 | 4-Amino-5-(2-isopropyl-2H-1,2,3-triazol-4-yl)-5-methyl-2-(1-methyl-6-(3,3,4,4-pentafluorobutyl)-1H-pyrazolo[3,4-d]pyrimidin-4-yl)-5,7-dihydro-6H-pyrrolo[2,3-d]pyrimidin-6-one; |
| 62 | 4-Amino-5-cyclopropyl-5-(1-methyl-1H-1,2,3-triazol-4-yl)-2-(1-methyl-6-(4,4,4-trifluorobutyl)-1H-pyrazolo[3,4-d]pyrimidin-4-yl)-5,7-dihydro-6H-pyrrolo[2,3-d]pyrimidin-6-one; |
| 63 | 4-Amino-5-(1-(cyclopropylmethyl)-1H-1,2,3-triazol-4-yl)-5-methyl-2-(1-(methyl-d3)-6-(3,3,4,4-pentafluorobutyl)-1H-pyrazolo[3,4-d]pyrimidin-4-yl)-5,7-dihydro-6H-pyrrolo[2,3-d]pyrimidin-6-one; |
| 64 | 4-Amino-5-(1-ethyl-1H-1,2,3-triazol-4-yl)-5-methyl-2-(1-(methyl-d3)-6-(3,3,4,4-pentafluorobutyl)-1H-pyrazolo[3,4-d]pyrimidin-4-yl)-5,7-dihydro-6H-pyrrolo[2,3-d]pyrimidin-6-one; |
| 65 | 4-Amino-5-(1-(cyclopropylmethyl)-1H-1,2,3-triazol-4-yl)-5-methyl-2-(1-methyl-6-(3,3,4,4-pentafluorobutyl)-1H-pyrazolo[3,4-d]pyrimidin-4-yl)-5,7-dihydro-6H-pyrrolo[2,3-d]pyrimidin-6-one; |
| 66 | 4-Amino-5-ethyl-5-(1-ethyl-1H-1,2,3-triazol-4-yl)-2-(1-methyl-6-(3,3,4,4-pentafluorobutyl)-1H-pyrazolo[3,4-d]pyrimidin-4-yl)-5,7-dihydro-6H-pyrrolo[2,3-d]pyrimidin-6-one; |
| 67 | 4-Amino-5-(1-isopropyl-1H-1,2,3-triazol-4-yl)-5-methyl-2-(1-(methyl-d3)-6-(3,3,4,4-pentafluorobutyl)-1H-pyrazolo[3,4-d]pyrimidin-4-yl)-5,7-dihydro-6H-pyrrolo[2,3-d]pyrimidin-6-one; |
| 68 | 4-Amino-5-ethyl-5-(1-isopropyl-1H-1,2,3-triazol-4-yl)-2-(1-methyl-6-(3,3,4,4-pentafluorobutyl)-1H-pyrazolo[3,4-d]pyrimidin-4-yl)-5,7-dihydro-6H-pyrrolo[2,3-d]pyrimidin-6-one; |
| 69 | 4-Amino-5-(1-ethyl-1H-1,2,3-triazol-4-yl)-5-methyl-2-(1-methyl-6-(3,3,4,4-pentafluorobutyl)-1H-pyrazolo[3,4-d]pyrimidin-4-yl)-5,7-dihydro-6H-pyrrolo[2,3-d]pyrimidin-6-one; |
| 70 | 34-Amino-5-(1-isobutyl-1H-1,2,3-triazol-4-yl)-5-methyl-2-(1-methyl-6-(3,3,4,4-pentafluorobutyl)-1H-pyrazolo[3,4-d]pyrimidin-4-yl)-5,7-dihydro-6H-pyrrolo[2,3-d]pyrimidin-6-one; |
| 71 | 4-Amino-5-methyl-2-(1-methyl-6-(3,3,4,4-pentafluorobutyl)-1H-pyrazolo[3,4-d]pyrimidin-4-yl)-5-(1-propyl-1H-1,2,3-triazol-4-yl)-5,7-dihydro-6H-pyrrolo[2,3-d]pyrimidin-6-one; |

| EX | Compound Name |
|---|---|
| 72 | 4-Amino-5-ethyl-2-(1-methyl-6-(3,3,4,4,4-pentafluorobutyl)-1H-pyrazolo[3,4-d]pyrimidin-4-yl)-5-(1-propyl-1H-1,2,3-triazol-4-yl)-5,7-dihydro-6H-pyrrolo[2,3-d]pyrimidin-6-one; |
| 73 | 4-Amino-5-ethyl-2-(1-methyl-6-(3,3,4,4,4-pentafluorobutyl)-1H-pyrazolo[3,4-d]pyrimidin-4-yl)-5-(1-propyl-1H-1,2,3-triazol-4-yl)-5,7-dihydro-6H-pyrrolo[2,3-d]pyrimidin-6-one; |
| 74 | 4-Amino-5-(1-cyclobutyl-1H-1,2,3-triazol-4-yl)-5-methyl-2-(1-methyl-6-(3,3,4,4,4-pentafluorobutyl)-1H-pyrazolo[3,4-d]pyrimidin-4-yl)-5,7-dihydro-6H-pyrrolo[2,3-d]pyrimidin-6-one; |
| 75 | 5-(1-allyl-1H-1,2,3-triazol-4-yl)-4-amino-5-methyl-2-(1-methyl-6-(3,3,4,4,4-pentafluorobutyl)-1H-pyrazolo[3,4-d]pyrimidin-4-yl)-5,7-dihydro-6H-pyrrolo[2,3-d]pyrimidin-6-one; |
| 76 | 4-Amino-5-methyl-5-(1-(methyl-d3)-1H-1,2,3-triazol-4-yl)-2-(1-(methyl-d3)-6-(3,3,4,4,4-pentafluorobutyl)-1H-pyrazolo[3,4-d]pyrimidin-4-yl)-5,7-dihydro-6H-pyrrolo[2,3-d]pyrimidin-6-one; |
| 77 | 4-Amino-5-methyl-2-(1-methyl-6-(3,3,4,4,4-pentafluorobutyl)-1H-pyrazolo[3,4-d]pyrimidin-4-yl)-5-(1-(methyl-d3)-1H-1,2,3-triazol-4-yl)-5,7-dihydro-6H-pyrrolo[2,3-d]pyrimidin-6-one; |
| 78 | 4-Amino-5-(1-isopropyl-1H-1,2,3-triazol-4-yl)-5-methyl-2-(1-methyl-6-(4,4,4-trifluorobutyl)-1H-pyrazolo[3,4-d]pyrimidin-4-yl)-5,7-dihydro-6H-pyrrolo[2,3-d]pyrimidin-6-one; |
| 79 | 4-Amino-5-(2-ethyl-2H-1,2,3-triazol-4-yl)-5-methyl-2-(1-methyl-6-(3,3,4,4,4-pentafluorobutyl)-1H-pyrazolo[3,4-d]pyrimidin-4-yl)-5,7-dihydro-6H-pyrrolo[2,3-d]pyrimidin-6-one; |
| 80 | 4-Amino-5-methyl-5-(2-methyl-2H-1,2,3-triazol-4-yl)-2-(1-methyl-6-(3,3,4,4,4-pentafluorobutyl)-1H-pyrazolo[3,4-d]pyrimidin-4-yl)-5,7-dihydro-6H-pyrrolo[2,3-d]pyrimidin-6-one; |
| 81 | 4-Amino-5-(1-isopropyl-1H-1,2,3-triazol-4-yl)-5-methyl-2-(1-methyl-6-(3,3,4,4,4-pentafluorobutyl)-1H-pyrazolo[3,4-d]pyrimidin-4-yl)-5,7-dihydro-6H-pyrrolo[2,3-d]pyrimidin-6-one; |
| 82 | Ethyl 3-(2-(4-amino-5-cyclopropyl-2-(1-(methyl-d3)-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidin-5-yl)thiazol-4-yl)-2,2-dimethylpropanoate; |
| 83 | 3-(2-(4-Amino-5-cyclopropyl-2-(1-(methyl-d3)-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidin-5-yl)thiazol-4-yl)-2,2-dimethylpropanoic acid; |
| 84 | 4-Amino-5-methyl-2-(1-methyl-6-(3,3,4,4,4-pentafluorobutyl)-1H-pyrazolo[3,4-d]pyrimidin-4-yl)-5-(1H-tetrazol-1-yl)-5,7-dihydro-6H-pyrrolo[2,3-d]pyrimidin-6-one; |
| 85 | 4-Amino-5-(5-fluoropyridin-2-yl)-5,7'-dimethyl-2'-(3,3,4,4,4-pentafluorobutyl)-5,7-dihydro-6H,7'H-[2,4'-bipyrrolo[2,3-d]pyrimidin]-6-one; |
| 86 | 4-Amino-5-(5-cyclopropyl-1,3,4-oxadiazol-2-yl)-5,7'-dimethyl-2'-(3,3,4,4,4-pentafluorobutyl)-5,7-dihydro-6H,7'H-[2,4'-bipyrrolo[2,3-d]pyrimidin]-6-one; |
| 87 | 4-Amino-5,7'-dimethyl-5-(5-methyl-1,3,4-oxadiazol-2-yl)-2'-(3,3,4,4,4-pentafluorobutyl)-5,7-dihydro-6H,7'H-[2,4'-bipyrrolo[2,3-d]pyrimidin]-6-one; or |
| 88 | 4-Amino-cyclopropyl-5-(5-cyclopropyl-1,3,4-oxadiazol-2-yl)-7'-methyl-2'-(3,3,4,4,4-pentafluorobutyl)-5,7-dihydro-6H,7'H-[2,4'-bipyrrolo[2,3-d]pyrimidin]-6-one; |

All structural Formulas, embodiments and classes thereof described herein include the pharmaceutically acceptable salts of the compounds defined therein. Reference to the compounds of structural Formula I includes the compounds of other generic structural Formulas and embodiments that fall within the scope of Formula I, including but not limited to Formula Ia, Formula Ib and Embodiment 1.

As used herein except where noted, "alkyl" is intended to include both branched- and straight-chain saturated aliphatic hydrocarbon groups having the specified number of carbon atoms when noted. Commonly used abbreviations for alkyl groups are used throughout the specification, e.g. methyl may be represented by conventional abbreviations including "Me" or $CH_3$ or a symbol that is an extended bond without a defined terminal group, e.g., a methyl substituent on phenyl may be represented as:

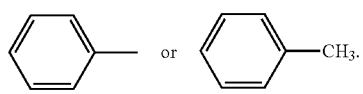

Ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_{1-6}$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. If no number is specified, 1-10 carbon atoms are intended for linear or branched alkyl groups. A phrase like or similar to "$C_{1-6}$alkyl unsubstituted or substituted with 1-3 fluorine atoms" refers to alkyl groups having 0, 1, 2 or 3 fluorine atoms wherein each fluorine is attached to one or more carbon atoms. The term "cycloalkyl" means a cyclized alkyl ring (i.e., a carbocycle) containing no heteroatoms. Examples of cycloalkyl include cyclopropyl (cPr or cyPr), cyclobutyl (cBu or cyBu), cyclopentyl, cyclohexyl, cycloheptyl, decahydronaphthyl and the like. In an embodiment, cycloalkyl is cyclopropyl or cyclobutyl, and particularly cyclopropyl.

Alkyl, alkenyl, alkynyl and cycloalkyl are each intended to include such carbon moieties containing isotopic forms of hydrogen (H) such as protium ($^1H$), for example but not limited to —$CH_3$, and/or deuterium ($^2H$, also denoted herein as D), for example but not limited to -$CD_3$.

"Alkenyl" unless otherwise indicated, means carbon chains which contain at least one carbon-carbon double bond, and which may be linear or branched or combinations thereof. Examples of alkenyl include, but are not limited to, vinyl, allyl, isopropenyl, pentenyl, hexenyl, heptenyl, 1-propenyl, 2-butenyl, 2-methyl-2-butenyl, and the like. The term "alkynyl" refers to a hydrocarbon radical straight or branched, containing the specified number of carbon atoms and at least one carbon to carbon triple bond. Alkynyl groups include ethynyl, propynyl, butynyl, 3-methylbutynyl and so on.

"Heteroaryl" unless otherwise indicated, means a mono- or bicyclic aromatic ring or ring system, wherein the ring or ring system is made up of a specified number of atoms when noted, and which contains at least one heteroatom selected from O, S and N or a specified number and selection of heteroatoms when noted. Examples include, but are not limited to, pyrrolyl, isoxazolyl, isothiazolyl, pyrazolyl, pyridyl, oxazolyl, oxadiazolyl, 1,3,4-oxadiazolyl-2(3H)-one, thiadiazolyl, thiazolyl, imidazolyl, triazolyl, tetrazolyl, furanyl, triazinyl, thienyl, pyridinyl, pyrimidinyl, pyrimidyl, pyridazinyl, pyrazinyl, and the like. Heteroaryl also includes a bicyclic ring system comprised of a mono-heteroaryl ring fused to a heterocyclic ring or a cycloalkyl ring. Additional examples of heteroaryls include, but are not limited to, indazolyl, thienopyrazolyl, imidazopyridazinyl, pyrazolopyrazolyl, pyrazolopyridinyl, imidazopyridinyl and imidazothiazolyl. Heteroaryl also includes such groups in charged form, e.g., pyridinium.

"Heterocyclyl," "heterocyclic," "heterocycle" or the like, unless otherwise indicated, means a 5- or 6-membered monocyclic non-aromatic or saturated ring containing at least one heteroatom selected from N, S and O, in which the point of attachment may be via an available carbon or nitrogen in the ring. Examples include, but are not limited to, pyrrolidinyl, piperidinyl, piperazinyl, morpholinyl, imidazolidinyl, 2,3-dihydrofuro(2,3-b)pyridyl, benzoxazinyl, oxetanyl, tetrahydrofuranyl or tetrahydropyranyl and the like. The terms also includes partially unsaturated monocyclic rings that are not aromatic, such as 2- or 4-pyridones attached through the nitrogen or N-substituted-(1H, 3H)-pyrimidine-2, 4-diones (N-substituted uracils). The terms also include such moieties in charged form, e.g., piperidinium.

"Halogen" (or "halo") unless otherwise indicated, includes fluorine (fluoro), chlorine (chloro), bromine (bromo) and iodine (iodo). In one embodiment, halo is fluoro (—F) or chloro (—Cl).

When any variable (e.g., $R^1$, $R^2$, etc.) occurs more than one time in any constituent or in Formula I or other generic Formulae herein, its definition on each occurrence is independent of its definition at every other occurrence. Combinations of substituents and/or variables are permissible only if such combinations result in stable compounds. In choosing compounds of the present invention, one of ordinary skill in the art will recognize that the various substituents, i.e., $R^1$, $R^2$, etc., are to be chosen in conformity with well-known principles of chemical structure connectivity and stability. Unless expressly stated to the contrary, substitution by a named substituent is permitted on any atom in a ring (e.g., aryl, a heteroaryl ring, or a saturated heterocyclic ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

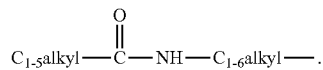

Unless expressly depicted or described otherwise, variables depicted in a structural formula with a "floating" bond, such as $R^6$, are permitted on any available carbon atom in the ring to which the variable is attached. When a moiety is noted as being "optionally substituted" in Formula I or any embodiment thereof, it means that Formula I or the embodiment thereof encompasses compounds that contain the noted substituent (or substituents) on the moiety and also compounds that do not contain the noted substituent (or substituents) on the moiety.

Compounds of structural Formula I may contain one or more asymmetric centers and can thus occur as racemates and racemic mixtures, single enantiomers, diastereoisomeric mixtures and individual diastereoisomers. Centers of asymmetry that are present in the compounds of Formula I can all independently of one another have S configuration or R configuration. The compounds of this invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The present invention is meant to comprehend all such stereo-isomeric forms of the compounds of structural Formula I.

Compounds of structural Formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration. Alternatively, any stereoisomer or isomers of a compound of Formula I may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

For compounds of Formula I described herein which contain olefinic double bonds, unless specified otherwise, they are meant to include both E and Z geometric isomers.

Some of the compounds described herein may exist as tautomers which have different points of attachment of hydrogen accompanied by one or more double bond shifts. For example, a ketone and its enol form are keto-enol tautomers. The individual tautomers as well as mixtures thereof are encompassed with compounds of Formula I of the present invention.

In the compounds of structural Formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention as described and claimed herein is meant to include all suitable isotopic variations of the compounds of structural Formula I and embodiments thereof. For example, different isotopic forms of hydrogen (H) include protium (1H) and deuterium ($^2$H, also denoted herein as D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within structural Formula I, can be prepared without undue experimentation by conventional techniques well known to those skilled in the art or by processes analogous to those described in the Schemes and Examples herein using appropriate isotopically-enriched reagents and/or intermediates.

It will be understood that, as used herein, references to the compounds of structural Formula I are meant to also include the pharmaceutically acceptable salts thereof. and also salts that are not pharmaceutically acceptable when they are used as precursors to the free compounds or their pharmaceutically acceptable salts or in other synthetic manipulations. The compounds of the present invention, including the compounds of the Examples, also includes all salts of the compounds of Formula I which, owing to low physiological compatibility, are not directly suitable for use in pharmaceuticals but which can be used, for example, as intermediates for chemical reactions or for the preparation of physiologically acceptable salts.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, benzenesulfonate, benzoate, bicarbonate, bisulfate, bitartrate, borate, bromide, butyrate, camphorate, camphorsulfonate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, methanesulfonate, mucate, napsylate, nitrate, N-methylglucamine ammonium salt, oleate, oxalate, pamoate (embonate), palmitate, pantothenate, phosphate/diphosphate, polygalacturonate, propionate, salicylate, stearate, sulfate, subacetate, succinate, tannate, tartrate, teoclate, thiocyanate, tosylate, triethiodide, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

Furthermore, compounds of the present invention may exist in amorphous form and/or one or more crystalline forms, and as such all amorphous and crystalline forms and mixtures thereof of the compounds of Formula I, including the Examples, are intended to be included within the scope of the present invention. In addition, some of the compounds of the instant invention may form solvates with water (i.e., a hydrate) or common organic solvents such as but not limited to ethyl acetate. Such solvates and hydrates, particularly the pharmaceutically acceptable solvates and hydrates, of the instant compounds are likewise encompassed within the scope of this invention, along with un-solvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid (—COOH) group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Included are those esters and acyl groups known in the art for modifying the solubility or hydrolysis characteristics for use as sustained-release or prodrug formulations. Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed.

Accordingly, the compounds within the generic structural formulas, embodiments and specific compounds described in the Examples and claimed herein encompass salts, all possible stereoisomers and tautomers, physical forms (e.g., amorphous and crystalline forms), solvate and hydrate forms thereof and any combination of these forms, as well as the salts, pro-drug forms thereof, and salts of pro-drug forms thereof, where such forms are possible unless specified otherwise.

The present invention also relates to processes for the preparation of the compounds of Formula I which are described in the following and by which the compounds of the invention are obtainable.

The compounds of Formula I according to the invention effect an increase of cGMP concentration via the activation of the soluble guanylate cyclase (sGC), and they are therefore useful agents for the therapy and prophylaxis of disorders which are associated with a low or decreased cGMP level or which are caused thereby, or for whose therapy or prophylaxis an increase of the present cGMP level is desired. The activation of the sGC by the compounds of Formula I can be examined, for example, in the activity assay described below.

The terms "therapeutically effective (or efficacious) amount" and similar descriptions such as "an amount efficacious for treatment" are intended to mean that amount of a pharmaceutical drug that will elicit the biological or medical response of a tissue, a system, animal or human that is being sought by a researcher, veterinarian, medical doctor or other clinician. The terms "prophylactically effective (or efficacious) amount" and similar descriptions such as "an amount efficacious for prevention" are intended to mean that amount of a pharmaceutical drug that will prevent or reduce the risk of occurrence of the biological or medical event that is sought to be prevented in a tissue, a system, animal or human by a researcher, veterinarian, medical doctor or other clinician. As an example, the dosage a patient receives can be selected so as to achieve the desired reduction in blood pressure; the dosage a patient receives may also be titrated over time in order to reach a target blood pressure. The dosage regimen utilizing a compound of the instant invention is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition. It is understood that a specific daily dosage amount can simultaneously be both a therapeutically effective amount, e.g., for treatment of hypertension, and a prophylactically effective amount, e.g., for prevention of myocardial infarction.

Disorders and pathological conditions which are associated with a low cGMP level or in which an increase of the cGMP level is desired and for whose therapy and prophylaxis it is possible to use compounds of Formula I are, for example, cardiovascular diseases, such as endothelial dysfunction, diastolic dysfunction, atherosclerosis, hypertension, heart failure, pulmonary hypertension, which includes pulmonary arterial hypertension (PAH), stable and unstable angina pectoris, thrombosis, restenosis, myocardial infarction, strokes, cardiac insufficiency or pulmonary hypertonia, or, for example, erectile dysfunction, asthma bronchiale, chronic kidney disease and diabetes. Compounds of Formula I can additionally be used in the therapy of cirrhosis of the liver and also for improving a restricted memory performance or ability to learn.

The compounds of Formula I and their pharmaceutically acceptable salts can be administered to animals, preferably to mammals, and in particular to humans, as pharmaceuticals by themselves, in mixtures with one another or in the form of pharmaceutical preparations. The term "patient" includes animals, preferably mammals and especially humans, who use the instant active agents for the prevention or treatment of a medical condition. Administering of the drug to the patient includes both self-administration and administration to the patient by another person. The patient may be in need of, or desire, treatment for an existing disease or medical condition, or may be in need of or desire prophylactic treatment to prevent or reduce the risk of occurrence of said disease or medical condition. As used herein, a patient "in need" of treatment of an existing condition or of prophylactic treatment encompasses both a determination of need by a medical professional as well as the desire of a patient for such treatment.

A subject of the present invention therefore also are the compounds of Formula I and their pharmaceutically acceptable salts for use as pharmaceuticals, their use for activating soluble guanylate cyclase, for normalizing a disturbed cGMP balance and in particular their use in the therapy and prophylaxis of the abovementioned syndromes as well as their use for preparing medicaments for these purposes.

A therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. It is understood that a specific daily dosage amount can simultaneously be both a therapeutically effective amount, e.g., for treatment of hypertension, and a prophylactically effective amount, e.g., for prevention of myocardial infarction.

Furthermore, a subject of the present invention are pharmaceutical preparations (or pharmaceutical compositions) which comprise as active component an effective dose of at least one compound of Formula I and/or a pharmaceutically acceptable salt thereof and a customary pharmaceutically acceptable carrier, i.e., one or more pharmaceutically acceptable carrier substances and/or additives.

Thus, a subject of the invention are, for example, said compound and its pharmaceutically acceptable salts for use as a pharmaceutical, pharmaceutical preparations which comprise as active component an effective dose of said compound and/or a pharmaceutically acceptable salt thereof and a customary pharmaceutically acceptable carrier, and the uses of said compound and/or a pharmaceutically acceptable salt thereof in the therapy or prophylaxis of the above-mentioned syndromes as well as their use for preparing medicaments for these purposes.

The pharmaceuticals according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

The amount of active compound of Formula I and/or its pharmaceutically acceptable salts in the pharmaceutical preparations normally is from 0.2 to 200 mg, preferably from 1 to 200 mg, per dose, but depending on the type of the pharmaceutical preparation it can also be higher. The pharmaceutical preparations usually comprise 0.5 to 90 percent by weight of the compounds of Formula I and/or their pharmaceutically acceptable salts. The preparation of the pharmaceutical preparations can be carried out in a manner known per se. For this purpose, one or more compounds of Formula I and/or their pharmaceutically acceptable salts, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine.

For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of Formula I and their pharmaceutically acceptable salts and to use the resulting lyophilisates, for example, for preparing preparations for injection or infusion. Suitable carriers for microcapsules, implants or rods are, for example, copolymers of glycolic acid and lactic acid.

Besides the active compounds and carriers, the pharmaceutical preparations can also contain customary additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the active compound of Formula I and/or of a pharmaceutically acceptable salt thereof to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. In general, a daily dose of approximately 0.01 to 100 mg/kg, preferably 0.01 to 10 mg/kg, in particular 0.3 to 5 mg/kg (in each case mg per kg of bodyweight) is appropriate for administration to an adult weighing approximately 75 kg in order to obtain the desired results. The daily dose can be administered in a single dose or, in particular when larger amounts are administered, be divided into several, for example two, three or four individual doses. In some cases, depending on the individual response, it may be necessary to deviate upwards or downwards from the given daily dose. A single daily dose is preferred.

The compounds of Formula I activate soluble guanylate cyclase. On account of this property, apart from use as pharmaceutically active compounds in human medicine and veterinary medicine, they can also be employed as a scientific tool or as an aid for biochemical investigations in which such an effect on soluble guanylate cyclase is intended, and also for diagnostic purposes, for example in the in vitro diagnosis of cell samples or tissue samples. The compounds of Formula I and salts thereof can furthermore be employed, as already mentioned above, as intermediates for the preparation of other pharmaceutically active compounds.

One or more additional pharmacologically active agents may be administered in combination with a compound of Formula I. An additional active agent (or agents) is intended to mean a pharmaceutically active agent (or agents) that is active in the body, including pro-drugs that convert to pharmaceutically active form after administration, which are different from the compound of Formula I, and also includes free-acid, free-base and pharmaceutically acceptable salts of said additional active agents. Generally, any suitable additional active agent or agents, including but not limited to anti-hypertensive agents, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists (e.g., losartan i.e., COZAAR®, valsartan, candesartan, olmesartan, telmesartan and any of these drugs used in combination with hydrochlorothiazide such as HYZAAR®); neutral endopeptidase inhibitors (e.g., thiorphan and phosphoramidon), aldosterone antagonists, aldosterone synthase inhibitors, renin inhibitors (e.g. urea derivatives of di- and tri-peptides (See U.S. Pat. No. 5,116,835), amino acids and derivatives (U.S.

Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451)); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, phosphodiesterase-5 inhibitors (e.g. sildenafil, tadalfil and vardenafil), vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine); lipid lowering agents e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®) and ezetimibe in combination with any other lipid lowering agents such as the HMG-CoA reductase inhibitors noted above and particularly with simvastatin (e.g., VYTORIN®) or with atorvastatin calcium (e.g. LIPTRUZET®); niacin in immediate-release or controlled release forms; niacin receptor agonists such as acipimox and acifran, as well as niacin receptor partial agonists; metabolic altering agents including insulin sensitizing agents and related compounds (e.g., muraglitazar, glipizide, metformin, rosiglitazone) or with other drugs beneficial for the prevention or the treatment of the above-mentioned diseases including nitroprusside and diazoxide the free-acid, free-base, and pharmaceutically acceptable salt forms of the above active agents where chemically possible.

The following examples are provided so that the invention might be more fully understood. Unless otherwise indicated, the starting materials are commercially available. They should not be construed as limiting the invention in any way.

Several methods for preparing the compounds of this invention are described in the following Schemes and Examples. Starting materials and intermediates are purchased, made from known procedures, or as otherwise illustrated. Some frequently applied routes to the compounds of Formula I are also described by the Schemes as follows. In some cases the order of carrying out the steps of reaction schemes may be varied to facilitate the reaction or to avoid unwanted reaction products. The "R" and "X" groups in the Schemes correspond to the variables defined in Formula I at the same positions on the structures. Compounds 1a, 6d and 8a, which each have a —CH$_2$—R$^2$ moiety, are used for illustration purposes in Schemes 1, 6 and 8, but analogs of each compound having —CR$_2$R$^{2b}$R$^2$ in place of —CH$_2$—R$^2$ can likewise be employed resulting in downstream intermediates and final products containing the corresponding —CR$_2$R$^{2b}$R$^2$ moiety.

Compounds with structure 1 may be prepared by the sequence depicted in Scheme 1.

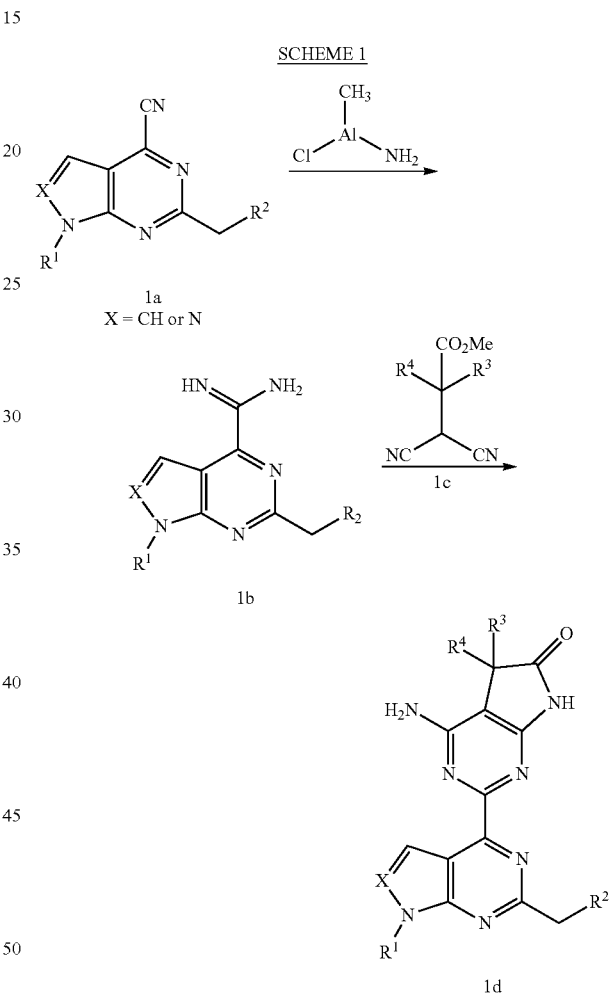

Conversion of the nitrile 1a to the amidine 1b can be accomplished with a reagent such as amino(chloro)methylaluminum, prepared from trimethylaluminum and ammonium chloride, in a non-polar solvent such as toluene at 100° C. as described by Garigipati, R. S. et al *Tetrahedron Letters* 1990, 31(14), 1969. The reaction may also be carried out on the corresponding methyl ester of compound 1a. Reaction of compound 1b with the amidine 1c in an alcoholic solvent such as MeOH, n-BuOH or t-BuOH and a base such as NaOMe, NaOEt, t-BuOK, K$_2$CO$_3$, KHCO$_3$, or NaHCO$_3$ at 90° C. to 150° C. affords the pyrimidine lactam 1d. The reaction may also be carried out in the absence of a base. Additionally, the reaction may also be carried out on the corresponding ethyl or propyl ester of compound 1c.

SCHEME 2

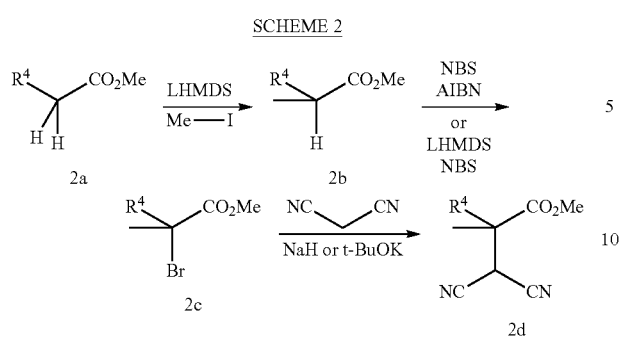

The preparation of compound 2d is outlined in Scheme 2. Deprotonation of ester 2a using a base such as LiHMDS, NaHMDS, NaH or LDA in a solvent such as THF or DMF followed by treatment with methyl iodide affords the ester 2b. The esters 2a and 2b may be prepared from the corresponding carboxylic acid by treatment with trimethylsilyl diazomethane or MeOH with catalytic sulfuric acid. Alternatively, the esters 2a and 2b may be prepared by the α-heteroarylation of esters as described by Buchwald, S. L. et al *Organic Letters* 2009, 11(8), 1773; or by Shen, H. C. et al *Organic Letters* 2006, 8(7), 1447. Compounds 2a and 2b, where $R^4$ is 5-membered ring heterocycle, may be prepared using methods familiar to those skilled in the art. For example, compound 2a, where $R^4$ is a 2-methyl-1,3-oxazol-4-yl group, may be prepared by the condensation of methyl chloroacetoacetate and acetamide. Compound 2b, where $R^4$ is a 3-methyl-1,2,4-oxadiazol-5-yl group, may be prepared from dimethyl methyl malonate using the procedure described by Du, W. et al *Tetrahedron Letters* 2006, 47(25), 4271. Compound 2b, where $R^4$ is a 5-methyl-1,3-oxazol-2-yl group, may be prepared from dimethyl methyl malonate using the procedure described by Hashmi, A. S. K. et al *Organic Letters* 2004, 6(23), 4391. In another example, compound 2b, where $R^4$ is a 5-methyl-1,2,4-oxadiazol-3-yl group, may be prepared by the reaction of methyl 2-methylcyanoacetate with hydroxylamine and acetic anhydride. The compound 2c is prepared by treating compound 2b with a brominating reagent such as NBS and AIBN in a solvent such as carbon tetrachloride at refluxing temperatures. Alternatively, the compound 2c may be prepared by reaction with NBS and magnesium perchlorate in acetonitrile solvent at RT as described by Yang, D. et al *Journal of Organic Chemistry* 2002, 67(21), 7429. Compound 2c may also be prepared by treating compound 6 with a base such as sodium hydride or LHMDS followed by treatment with NBS. Compound 2d is obtained from 2c by reaction with malononitrile and a base such as sodium hydride, t-BuOK, $K_2CO_3$ or DBU in a solvent such as THF or DMF at ambient temperature to 100° C. The synthetic sequence depicted in Scheme 2 may also be used to prepare the corresponding ethyl or propyl ester of compound 2d.

SCHEME 3

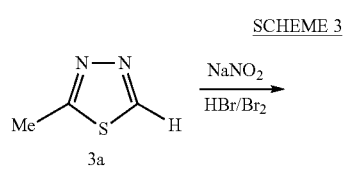

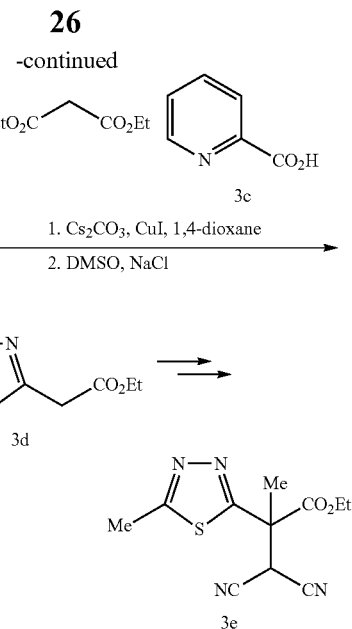

The preparation of 3e is outlined in Scheme 3 above. Starting with commercially available 2-methyl-1,3,4-thiadiazole 3a, bromination of the unsubstituted position of the thiadiazole with sodium nitrite and bromine affords 3b. Subsequent CuI mediated cross-coupling with diethyl malonate in the presence of 3c followed by decarboxylation affords afforded ester 3d. Ester 3d could be further elaborated to 3e via the sequence outlined in Scheme 2 starting from intermediate 2a.

SCHEME 4

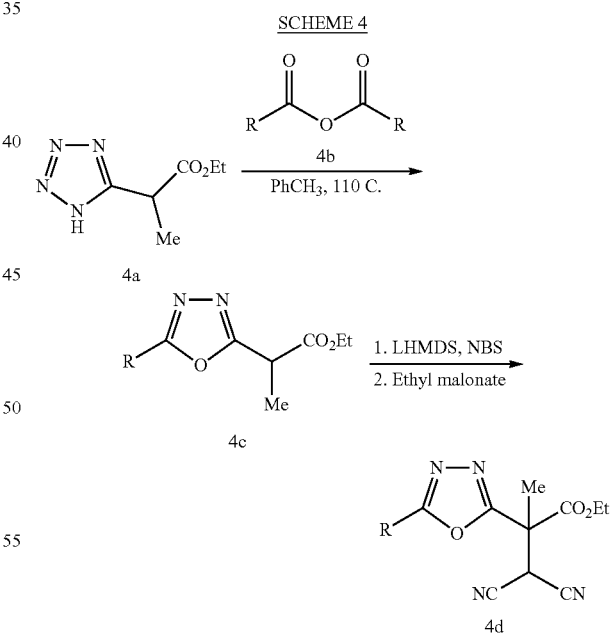

The preparation of 4d is outlined in Scheme 4 above. Starting with readily prepared ethyl 2-(1H-tetrazol-5-yl)propanoate (prepared analogous to *J. Med. Chem.* 1996, 39 (12), 2354 from commercially available 2-ethyl 2-cyanopropanoate), treatment with the desired carbonyl anhydride while heating in toluene affords the substituted oxadiazole 4c. Subsequent elaboration to 4d is achieved analogous to the conversion of 2b to 2d outlined in Scheme 2.

SCHEME 5

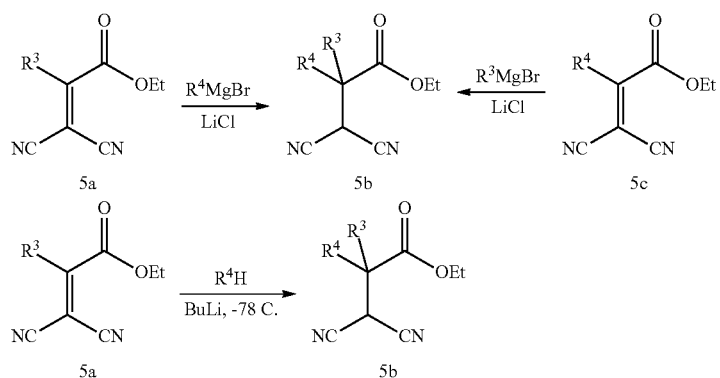

In addition to the methods described in Scheme 2 for the synthesis of intermediates of the generic structure 2d, similar compounds of the generic structure 5b (depicted as the ethyl ester) may also be prepared as shown in Scheme 3. Reaction of a suitable alkyl ($R^3$) magnesium halide, or heteroaryl ($R^4$) magnesium halide, with or without lithium chloride additive, or the lithiate of heteroaryl reagents derived via metal-halogen exchange or deprotonation, with the dicyanopropenoate 5a or 5c in a solvent such as THF affords compound 5b. Cycloalkyl ($R^3$), magnesium halides are also suitable reagents for this reaction. Compound 5a ($R^3$ is $CO_2Et$) can be prepared using the procedure described by Sentman et. al. *J. Org. Chem.* 1982, 47, 4577. Compound 5c ($R^4$=Me) can be prepared using the procedure described by Hagiware et. al. *Synthesis* 1974, 9, 669. Other analogs of this type ($R^4$=alkyl), can be prepared in a similar fashion.

SCHEME 6

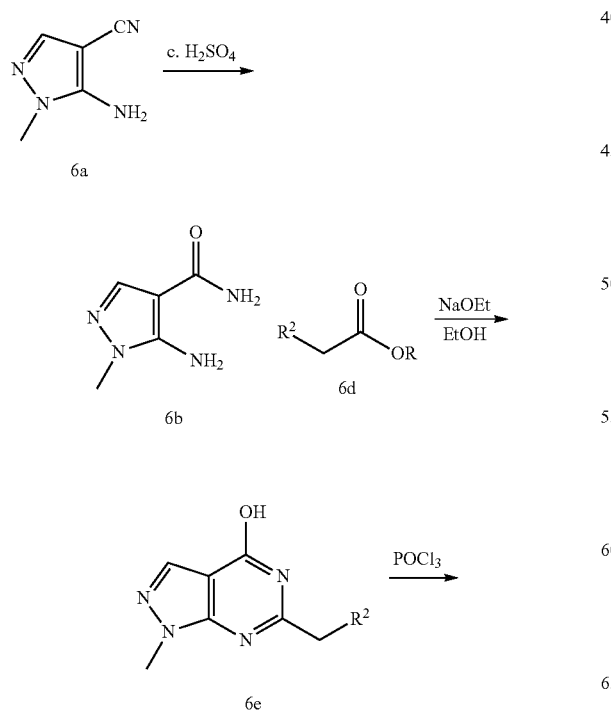

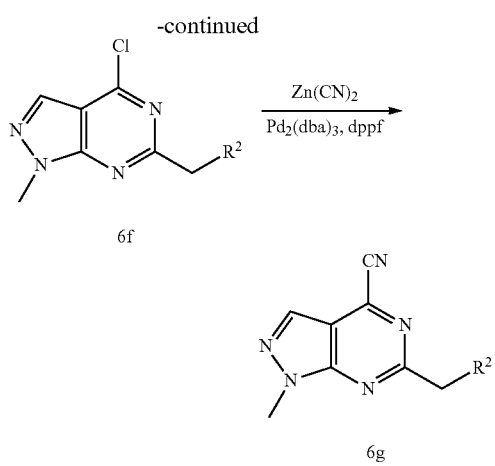

Compounds with structure 6g may be prepared by the sequence depicted in Scheme 6. Commercially available 5-amino-1-methyl-1H-pyrazole-4-carbonitrile (6a) can be converted the amide 6b by treatment with concentrated sulfuric acid, which can then be coupled to a suitable ester (6d) in the presence of a base such as sodium ethoxide (NaOEt) to afford 6e. Treatment of 6e with either neat phosphorous oxychloride or in a mixture of DCE and phosphorous oxychloride affords 6f. Finally, the nitrile 6g can be prepared by treatment of the chloride 6f with zinc cyanide in the presence of a suitable catalyst such as $Pd_2(dba)_3$ and a ligand such as dppf in a polar solvent such a DMF.

SCHEME 7

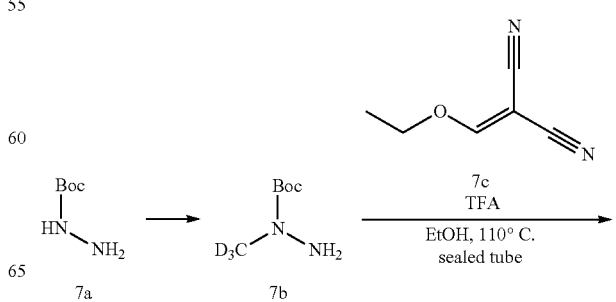

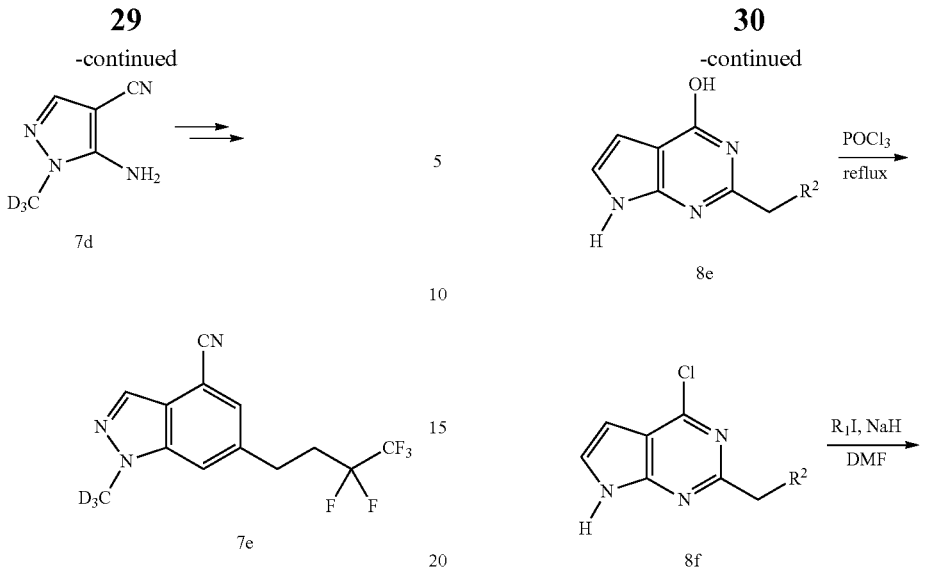

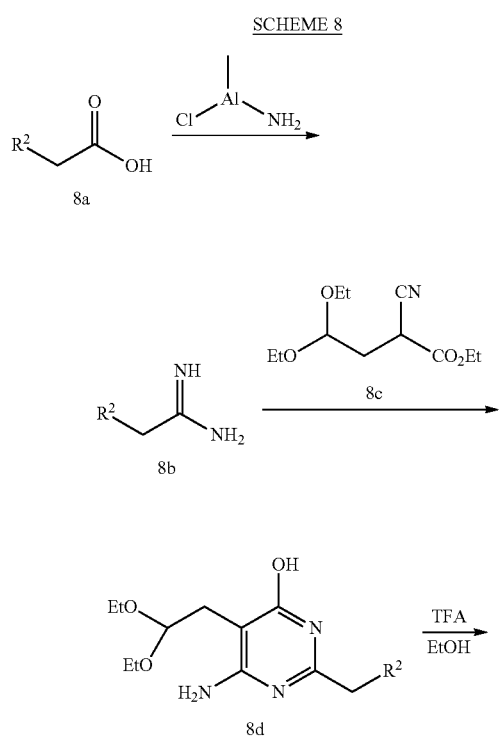

Compounds with structure 7e may be prepared by the sequence depicted in Scheme 7. Thus, treatment of tert-butyl carbazate (7a) with a suitable base such as solid NaHMDS in a solvent such as THF at ambient temperature followed by the addition of iodomethane-d₃ at 0° C. affords the desired product 7a which upon treatment with 2-(ethoxymethylene) malononitrile in the presence of TFA and an alcoholic solvent, such as EtOH, under refluxing conditions affords the desired product 5-Amino-1-(methyl-d3)-1H-pyrazole-4-carbonitrile (7d) which can be elaborated to 7e using the procedures described for conversion of 6a to 6g in Schemes 6.

Compounds with structure 8h may be prepared by the sequence depicted in Scheme 8. Conversion of an appropriately substituted acid 8a to the amidine 8b can be accomplished with a reagent such as amino(chloro)methylaluminum, prepared from trimethylaluminum and ammonium chloride, in a non-polar solvent such as toluene. Treatment of 8b with ethyl 2-cyano-4,4-diethoxybutanoate (8c) under refluxing conditions in an alcoholic solvent such as EtOH and suitable base such as sodium ethoxide affords the pyrimidine 8d. De-protection of the acetal under standard conditions such as TFA in EtOH at RT results in ring cyclization to afford 8e which can be converted to 8f by refluxing in phosphorous oxychloride. Alkylation of the NH can be accomplished using a suitable alkyl halide and a base such as sodium hydride in a suitable solvent such as DMF to give 8g. Finally, conversion of the chloride 8g to the nitrile 8h can be accomplished either by treatment of 8g with potassium cyanide in DMSO or treatment of 8g with zinc cyanide in the presence of a suitable catalyst such as Pd₂(dba)₃ and a ligand such as dppf in a polar solvent such a DMF.

SCHEME 9

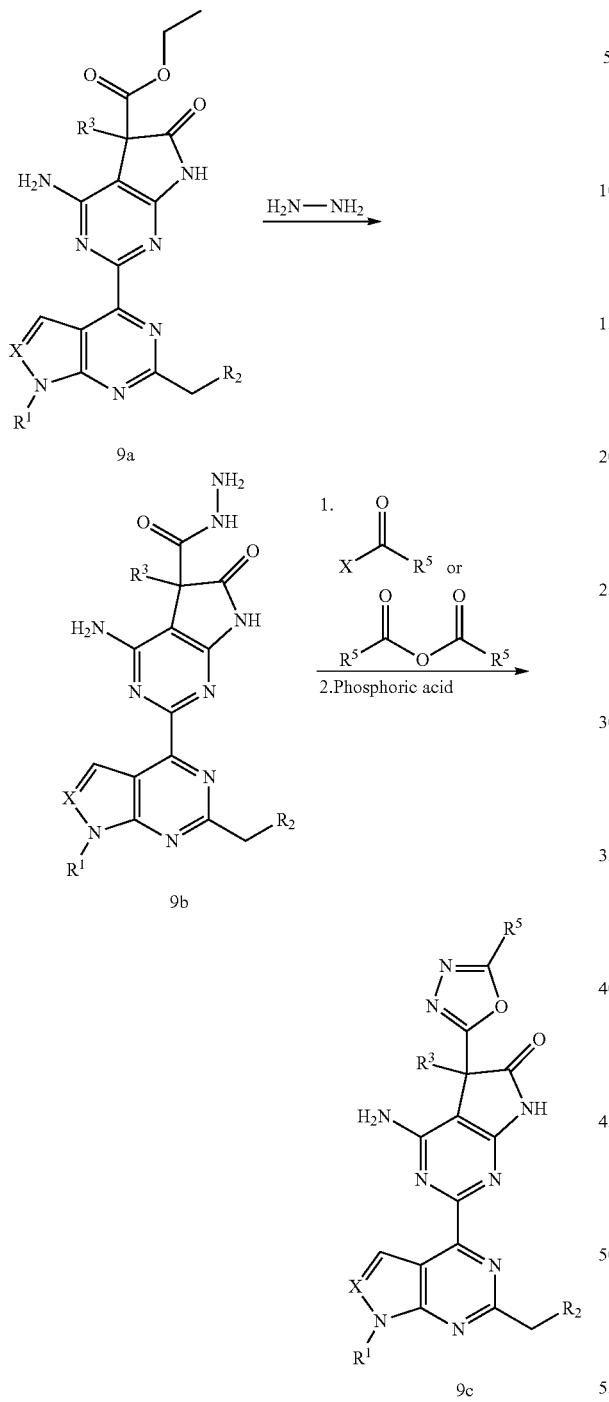

SCHEME 10

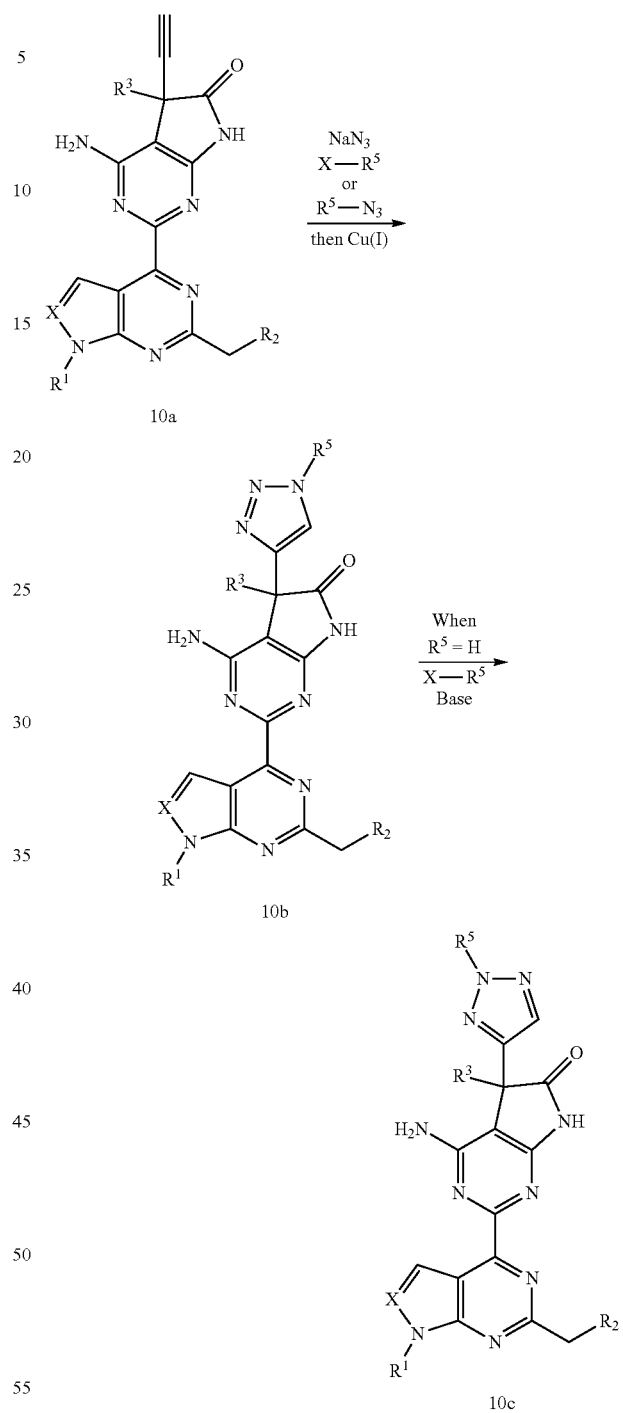

Compounds with structure 9c may be prepared by the sequence depicted in Scheme 9. Structure 9a can be formed analogously to the conversion of 1b to 1d as outlined in Scheme 1. Treatment of an intermediate of type 9a with hydrazine forms the acyl hydrazide intermediate 9b. Acylation of the primary amino group of the acyl hydrazide with an appropriate acylation reagent bearing the desired $R^5$ substitution forms an acyclic bis-acylated intermediate that can be subsequently cyclized in the presence of phosphoric acid en route to 9c.

Compounds with structure 10c may be prepared by the sequence depicted in Scheme 10. Structure 10a can be formed analogous to the conversion of 1b to 1d as outlined in Scheme 1. Treatment of alkyne 10a with a suitable alkyl azide that is either commercially available or formed in situ in the presence of a suitable copper source affords triazoles 10b. When $R^5$ is equal to a proton, the material can subsequently be treated with a alkyl halide and base to access the internally substituted triazoles 10c.

Compounds of the present invention possess an asymmetric center at the carbon bearing the $R^3$ substituent which can be either R or S configuration. These enantiomeric mixtures may be separated or resolved to single enantiomers using chiral SFC chromatography. Racemic material can be resolved to enantiomerically pure compounds at the final step, or one of the earlier steps in the route. For example, intermediates 9a, 9b or 9c in Scheme 9 can undergo chiral resolution to afford enantiopure isomers that may be carried on in the sequence to enantiomerically pure compounds.

achieved as known in the art by appropriate modification of the methodology disclosed herein. Their absolute stereochemistry may be determined by X-ray crystallography of crystalline products or crystalline intermediates which are derivatized, if necessary, with a reagent containing an asymmetric center of known absolute stereochemistry, or by vibrational circular dichroism (VCD) spectroscopy.

Throughout the synthetic schemes and examples, abbreviations and acronyms may be used with the following meanings unless otherwise indicated:

| | |
|---|---|
| aq, aq. = aqueous | AIBN = 2,2'-Azobisisobutyronitrile |
| Ar = aryl | $AuCl_3$ = gold trichloride |
| Ac = acetate | Bn = benzyl |
| $BF_3OEt_2$ = boron trifluoride diethyl etherate | t-BuOK = potassium tert-butoxide |
| Bu = butyl, t-Bu = tert-butyl | $t-Boc_2O$ = di-tent-butyl dicarbonate |
| t-BuONO = tert-butyl nitrite | conc, conc. = concentrated |
| cPr, cyPr = cyclopropyl | DBU = 1,8-Diazabicyclo[4.3.0]undec-7-ene |
| dppf = 1,1'-Bis(diphenylphosphino)ferrocene | dba = dibenzylideneacetone |
| DCE = 1,2-dichloroethane | DCM = dichloromethane |
| DIEA = diisopropylethylamine | DME = 1,2-dimethoxyethane |
| DMA, DMAC = dimethylacetamide | DMF = N,N-dimethylformamide |
| DMAP = 4-dimethylaminopyridine | DMSO = dimethylsulfoxide |
| Et = ethyl | EDC = 1-Ethyl-3-(3-dimethylaminopropyl) carbodiimidehydrochloride |
| EtOAc = ethyl acetate | |
| eq., eq, equiv = equivalent(s) | EtOH = ethanol |
| HOAc = acetic acid | $Fe(acac)_3$ = iron(III) acetylacetonate |
| h, hr = hour | HPLC = High pressure liquid chromatography |
| iPr = isopropyl | HMPA = hexamethylphosphoramide |
| IPA, i-PrOH = isopropanol | iPA = isopropyl alcohol |
| LAH = Lithium aluminum hydride | LDA = lithium diisopropylamide |
| Me = methyl | LiHMDS, LHMDS = lithium bis(trimethylsilyl)amide |
| min, min. = minute | |
| mCPBA = 3-chloroperoxybenzoic acid | MeOH = methanol |
| NaHMDS = sodium bis(trimethylsilyl)amide | mp, m.p. = melting point |
| NIS = N-iodosuccinimide | NMP = N-methylpyrrolidone |
| PDA = photodiode array | NBS = N-bromo succinmide |
| $Pd_2(dba)_3$ = tris(dibenzylideneacetone)dipalladium (0) | NMR = nuclear magnetic resonance |
| | Pd/C = palladium on activated carbon |
| $Pd(PPH_3)_4$ = tetrakis(triphenylphosphine)palladium (0) | Ph = phenyl |
| | Pr = propyl |
| iPrMgCl = isopropylmagnesium chloride | psig = pounds per square inch gauge |
| rt = retention time | PTFE = polytetrafluoroethylene |
| RT = room temperature or ambient temperature | sat., sat'd = saturated |
| SFC = supercritical fluid chromatography | TEA = triethylamine |
| TFA = trifluoroacetic acid | THF = tetrahydrofuran |
| TLC = thin layer chromatography | prep TLC = preparative thin layer chromatography |
| TMSCN = trimethylsilyl cyanide | TsCl = 4-toluenesulfonyl chloride |
| LCMS, LC/MS = liquid chromatography-mass spectrometry | PyBOP = (Benzotriazol-1-yloxy)tripyrrolidinophosphonium hexafluorophosphate |
| V = volume | |
| b.p. = boiling point | W = weight |
| mL = milliliters | L = liter(s) |
| mg = milligram(s) | g = gram(s) |
| Mmol = millimoles(s) | mol = mole(s) |
| nM = nanomolar | μM = micromolar |
| MeI = methyl iodide | ca = circa/about |
| mBar = millibar | $Et_2O$ = diethyl ether |
| MeCN = acetonitrile | t-BuOH = tertiary butanol |
| | HPLC = High Performance Liquid Chromatography |

Alternatively, enantiomeric resolution can be performed prior to the transformation of 1b to 1d. For example, chiral resolution of intermediates of the type 1c, 2d, 3e, 4d, and 5b to single enantiomers may be further elaborated to enantiopure compounds of the type 1d, 9a and 10a without additional chiral resolution. Characterization data may be of the chiral or racemic material. Unless otherwise noted, the examples in the present invention are enantiomerically pure isomers (R or S). Biochemical assay data is listed for the more active enantiomer if only one of the enantiomers is active.

The independent synthesis of diastereomers and enantiomers or their chromatographic separations may be The following examples are provided to more fully illustrate the present invention, and shall not be construed as limiting the scope in any manner. Unless stated otherwise, the following conditions were employed. All operations were carried out at RT, that is, at a temperature in the range 18-25° C. Reactions are generally done using commercially available anhydrous solvents under an inert atmosphere, either nitrogen or argon. Microwave reactions were done using a Biotage Initiator™ or CEM Explorer® system. Evaporation of solvent was carried out using a rotary evaporator under reduced pressure (4.5-30 mmHg) with a bath temperature of up to 50° C. The course of reactions was followed by TLC and/or tandem high HPLC followed by electron spray mass spectroscopy (MS), herein termed LCMS, and any reaction times are given for illustration only. The structure of all final compounds was assured by at least one of the following techniques: MS or proton nuclear magnetic resonance (1H NMR) spectrometry, and the purity was assured by at least one of the following techniques: TLC or HPLC. $^1$H NMR spectra were recorded on either a Varian Unity or a Varian Inova instrument at 400, 500 or 600 MHz using the indicated solvent; when line-listed, NMR data is in the form of delta values for major diagnostic protons, given in parts per million (ppm) relative to residual solvent peaks (multiplicity and number of hydrogens); conventional abbreviations used for signal shape are: s. singlet; d. doublet (apparent); t. triplet (apparent); m. multiplet; br. broad; etc. MS data were recorded on a Waters Micromass unit, interfaced with a Hewlett-Packard (Agilent 1100) HPLC instrument, and operating on MassLynx/OpenLynx software; electrospray ionization was used with positive (ES+) or negative ion (ES−) detection; and diode array detection. Purification of compounds by preparative reverse phase HPLC was performed on a Gilson system using a YMC-Pack Pro C18 column (150×20 mm i.d.) eluting at 20 mL/min with a water/acetonitrile (0.1% TFA) gradient (typically 5% acetonitrile to 95% acetonitrile) using a Sunfire Prep C18 OBD 5 μM column (100×30 mm i.d.) eluting at 50 mL/min with a water/acetonitrile (0.1% TFA) gradient. Purification of compounds by preparative thin layer chromatography (PTLC) was conducted on 20×20 cm glass plates coated with silica gel, commercially available from Analtech; or E. Merck. Flash column chromatography was carried out on a glass silica gel column using Kieselgel 60, 0.063-0.200 mm (SiO$_2$), or on a Biotage SiO$_2$ cartridge system using the Biotage Horizon and Biotage SP-1 systems; or a Teledyne Isco SiO$_2$ cartridge using the CombiFlashRf system.

The following are representative procedures for the preparation of intermediates used to prepare the final products described in the Examples that follow thereafter. These examples are provided for the purpose of further illustration only and are not intended to be limitations on the disclosed invention.

It is understood that a chiral center in a compound may exist in the "S" or "R" stereo-configurations, or as a mixture of both. In some of the examples for intermediate compounds and final compounds, such compounds having a racemic chiral center were separated into individual stereoisomers, for example, referred to as isomer A (or enantiomer A or the like), which refers to the observed faster eluting isomer, and isomer B (or enantiomer B or the like), which refers to the observed slower eluting isomer, and each such isomer may be noted in the example as either the fast or slow eluting isomer. When a single "A" or "B" isomer intermediate is used to prepare a downstream compound, the downstream compound may take the "A" or "B" designation that corresponds to the previously used intermediate.

Any Intermediates described below may be referred to herein by their number preceded by "I-." For illustration, in the example titled "Intermediate 2," the racemic parent title compound would be referred to as Intermediate 2 (or 1-2), and the separated stereoisomers are noted as Intermediates 2A and 2B (or I-2A and I-2B). In some examples, compounds having a chiral center were derived synthetically from a single isomer intermediate; e.g., Example 1 was made using stereoisomer I-2B. Absolute stereochemistry (R or S) of each of the separated isomers was not determined, unless specifically described otherwise. An asterisk (*) may be used in a chemical structure drawing that indicates the location of a chiral center.

INTERMEDIATE 1

Methyl 3,3-dicyano-2-methyl-2-(pyridin-2-yl)propanoate and the S and R isomers thereof

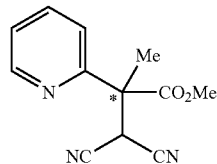 [SMILES: COC(=O)C(C)(c1ccccn1)C(C#N)C#N]

Step A

Methyl 2-(pyridin-2-yl)propanoate

Methyl 2-pyridylacetate (6.81 mL, 50 mmol) was added dropwise to LHMDS (1.0M in THF, 50 mL) and THF (65 mL) cooled to 0° C. After 30 min, iodomethane (3.97 g, 63.5 mmol) was added to the solution. After stirring for 1 h at 0° C. the solution was concentrated and the residue was purified by silica gel chromatography using a hexanes/EtOAc gradient to give the title product.

Step B

Methyl 2-bromo-2-(pyridin-2-yl)propanoate

Magnesium perchlorate (0.46 g, 2.08 mmol) was added to an acetonitrile (18 mL) solution containing the intermediate from Step A (1.04 g, 6.30 mmol). After stirring for 5 min, NBS (1.35 g, 7.55 mmol) was added and the reaction solution was stirred at RT overnight. The solution was then partitioned between EtOAc and 1N aq. NaHCO$_3$ solution. The organic layer was washed with brine, dried over MgSO$_4$, filtered and concentrated. The residue was purified by silica gel chromatography using a hexanes/EtOAc gradient to give the title product.

Step C

Methyl 3,3-dicyano-2-methyl-2-(pyridin-2-yl)propanoate

A DMF (7 mL) solution of malononitrile (0.413 g, 6.24 mmol) was added to a suspension of NaH (0.252 g, 6.30 mmol, 60%) in DMF (9 mL) cooled to 0° C. After 10 min a DMF (7 mL) solution of the intermediate from Step B (1.438 g, 5.89 mmol) was added. The reaction solution was then stirred overnight at RT. The solution was then partitioned between EtOAc and water. The organic layer was washed with brine, dried over MgSO$_4$, filtered and concentrated. The residue was purified by silica gel chromatography using a hexanes/EtOAc gradient to obtain the title racemic product. $^1$H NMR (400 MHz, CDCl$_3$): δ 8.59 (1H, d, J=4.8 Hz), 7.79 (1H, td, J=7.7, 1.8 Hz), 7.50 (1H, d, J=8.0 Hz), 7.32 (1H, dd, J=7.6, 4.8 Hz), 5.25 (1H, s), 3.77 (3H, s), 2.01 (3H, s). m/z=230.2 (M+H). The racemic material was resolved by chiral SFC (IA-H column CO$_2$/MeOH/MeCN) to obtain isomer I-1A (faster eluting) and isomer I-1B (slower eluting).

INTERMEDIATE 2

Ethyl 3,3-dicyano-2-(5-fluoropyridin-2-yl)-2-methylpropanoate and the S and R isomers thereof

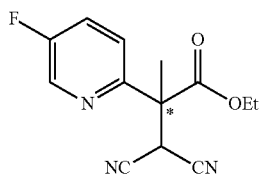 [SMILES: CCOC(=O)C(C)(c1ccc(F)cn1)C(C#N)C#N]

Step A

Diethyl 2-(5-fluoropyridin-2-yl)malonate

Into a 1-L round-bottom flask, was placed 2-bromo-5-fluoropyridine (20 g, 113.65 mmol, 1.0 equiv), 1,3-diethyl propanedioate (54.5 g, 340.27 mmol, 3.0 equiv), picolinic acid (5.6 g, 45.53 mmol, 0.4 equiv), $Cs_2CO_3$ (143 g, 438.65 mmol, 4.0 equiv), CuI (4.3 g, 22.58 mmol, 0.2 equiv), dioxane (500 mL). The resulting solution was stirred for 12 h at 100° C. in an oil bath. The resulting solution was quenched by the addition of 300 mL of water. The resulting solution was extracted with 2×200 mL of EtOAc and the organic layers combined and dried over anhydrous sodium sulfate and concentrated under vacuum. The residue was purified by silica chromatography using EtOAc/petroleum ether (0%~20%) to give the title compound.

Step B

Ethyl 2-(5-fluoropyridin-2-yl)acetate

Into a 100-mL 3-necked round-bottom flask, was placed intermediates from Step A (46 g, crude), NaCl (20 g), water (6 mL), DMSO (90 mL). The resulting solution was stirred for 3 h at 180° C. in an oil bath. The resulting solution was diluted with 500 mL of EtOAc, washed with 5×80 mL of water and dried over anhydrous sodium sulfate and concentrated under vacuum. The residue was purified by silica chromatography using EtOAc/petroleum ether (0%~20%) to give the title compound.

Step C

Ethyl 2-(5-fluoropyridin-2-yl)propanoate

Into a 500-mL round-bottom flask purged and maintained with an inert atmosphere of nitrogen, was placed THF (200 mL), LiHMDS (45 mL, 1.1 equiv, 1.0 M). This was followed by dropwise addition of the intermediate from Step B (7.5 g, 40.9 mmol, 1.0 equiv) with stirring at 0° C. After stirring the resulting solution for 1 h at 0° C., a solution of iodomethane (5.82 g, 41.0 mmol, 1.0 equiv) in THF (10 mL) was added dropwise with stirring at 0° C. The resulting solution was stirred for 3 h at 0° C. The reaction was then quenched by the addition of 200 mL of water. The resulting solution was extracted with 3×200 mL of EtOAc and the organic layers combined and dried over anhydrous sodium sulfate and concentrated in vacuo. The residue purified by silica chromatography using EtOAc/petroleum ether (0%~20%) to afford the title compound

Step D

Ethyl 2-bromo-2-(5-fluoropyridin-2-yl)propanoate

Into a 100-mL round-bottom flask purged and maintained with an inert atmosphere of nitrogen, was added the intermediate from Step C (1 g, 5.07 mmol, 1.0 equiv), and THF (50 mL). This was followed by the addition of LiHMDS (5 mL, 1.2 equiv, 1.0M) dropwise with stirring at −78° C. The resulting solution was stirred for 30 min at −78° C. Then NBS (1.27 g, 7.14 mmol, 1.4 equiv) in THF (10 mL) was added. The resulting solution was warmed to RT and stirred for 1 h. The reaction was then quenched by the addition of 50 mL of water. The resulting solution was extracted with 3×50 mL of EtOAc and the organic layers combined and dried over anhydrous sodium sulfate. The residue purified by silica chromatography using EtOAc/petroleum ether (0%~10%) to afford the title compound.

Step E

Ethyl 3,3-dicyano-2-(5-fluoropyridin-2-yl)-2-methylpropanoate

Into a 50-mL round-bottom flask was placed DMF (20 mL), sodium hydride (260 mg, 6.5 mmol, 1.9 equiv, 60%). This was followed by the addition of malononitrile (460 mg, 6.96 mmol, 2.0 equiv) dropwise with stirring at 0° C. The resulting solution was stirred for 30 min at 0° C. To this was added the intermediate from Step D (950 mg, 3.44 mmol, 1.0 equiv) in DMF dropwise with stirring at 0° C. The resulting solution was stirred for 1 h at RT. The resulting solution was quenched with 200 mL of water, and extracted with 300 mL of EtOAc. The organic layer was dried over anhydrous sodium sulfate. The residue purified by silica chromatography using EtOAc/petroleum ether (0%-20%). The racemic material was resolved using a chiral SFC (IA column) to afford isomer I-2A (faster eluting) and isomer I-2B (slower eluting) of the title compound. $^1$H-NMR: (300 MHz, $CDCl_3$, ppm): δ 1.22-1.27 (t, J=6.9 Hz, 3H), 2.002 (s, 3H), 4.19-4.29 (m, 2H), 5.17 (s, 1H), 7.47-7.57 (m, 2H), 8.44-8.45 (dd, J=0.9, 2.4 Hz, 1H).

INTERMEDIATE 3

Methyl 3,3-dicyano-2-methyl-2-(3-methyl-1,2,4-oxadiazol-5-yl)propanoate

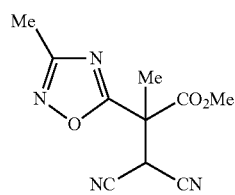 [SMILES: COC(=O)C(C)(c1nc(C)no1)C(C#N)C#N]

Step A

Methyl 2-(3-methyl-1,2,4-oxadiazol-5-yl)propanoate

To a screw cap pressure vessel was added acetamide oxime (0.900 g, 12.2 mmol) and dimethyl methyl malonate (3.55 g, 24.3 mmol) and the resulting mixture was heated at 140° C. for 4 h. The residue was purified by silica gel chromatography using a hexanes/EtOAc gradient to give the title product.

Step B

Methyl 2-bromo-2-(3-methyl-1,2,4-oxadiazol-5-yl)propanoate

The intermediate from Step A (0.765 g, 4.50 mmol), NBS (0.960 g, 5.39 mmol), and AIBN (0.037 g, 0.225 mmol) in 20 mL of $CCl_4$ was refluxed for 2 h. The mixture was cooled to RT, filtered, and concentrated. The residue was purified by silica gel chromatography using a hexanes/EtOAc gradient to give the title product

Step C

Methyl 3,3-dicyano-2-methyl-2-(3-yl-2-(3-methyl-1,2,4-oxadiazol-5-yl)propanoate

To NaH (0.525 g, 13.1 mmol, 60%) in 10 mL of DMF at 0° C. was added dropwise malononitrile (0.867 g, 13.1 mmol) in 10 mL of DMF. After stirring at RT for 20 min, the intermediate from Step B (2.97 g, 11.92 mmol) in 5 mL of DMF was added. The resulting mixture was stirred for 3 h. The solution was then quenched with saturated aq. $NH_4Cl$. The mixture was extracted with EtOAc, dried with $MgSO_4$, and concentrated. The residue was purified by silica gel chromatography using a hexanes/EtOAc gradient to give the title product. $^1H$ NMR ($CDCl_3$, 500 MHz) δ 4.83 (1H, s), 3.91 (3H, s), 2.48 (3H, s), 2.10 (3H, s).

INTERMEDIATE 4

Methyl 3,3-dicyano-2-methyl-2-(2-methyl-1,3-oxazol-4-yl)propanoate

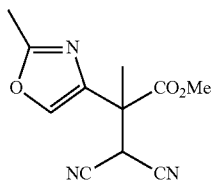 [SMILES: COC(=O)C(C)(c1coc(C)n1)C(C#N)C#N]

Step A

Methyl (2-methyl-1,3-oxazol-4-yl)acetate

A mixture of acetamide (1.312 g, 22.21 mmol) and methyl chloroacetoacetate in 20 mL of 1,4-dioxane and 20 mL of toluene was heated at 120° C. for 4 h. The solution was concentrated and the residue was purified by silica gel chromatography using a hexanes/EtOAc gradient to give the title product.

Step B

Methyl 2-(2-methyl-1,3-oxazol-4-yl)propanoate

To the intermediate from Step A (1.35 g, 8.71 mmol) and HMPA (6.24 g, 34.8 mmol) in 10 mL of THF at −78° C. was added dropwise an LDA solution (2.0 M, 5.22 mL, 10.5 mmol). The mixture was stirred at −78° C. for 30 min and MeI (1.48 g, 10.45 mmol) was added dropwise. The resulting mixture was slowly warmed to RT. The reaction was quenched with saturated aq. $NH_4Cl$ and extracted with EtOAc. The organic phase was washed with brine, dried with $MgSO_4$, filtered, and concentrated. The residue was purified by silica gel chromatography using a hexanes/EtOAc gradient to give the title product.

Step C

Methyl 2-bromo-2-(2-methyl-1,3-oxazol-4-yl)propanoate

A mixture of the intermediate from Step B (2.336 g, 13.81 mmol), NBS (2.458 g, 13.81 mmol), and AIBN (0.113 g, 0.690 mmol) in 50 mL of $CCl_4$ was refluxed for 1 h. The mixture was cooled to RT, filtered, and concentrated. The residue was purified by silica gel chromatography using a hexanes/EtOAc gradient to give the title product.

Step D

Methyl 3,3-dicyano-2-methyl-2-(2-methyl-1,3-oxazol-4-yl)propanoate

To NaH (60%, 0.293 g, 7.32 mmol) in 10 mL of DMF at RT was added dropwise malononitrile (0.483 g, 7.32 mmol) in 5 mL of DMF. After stirring at RT for 15 min, the intermediate from Step C (1.82 g, 7.32 mmol) in 10 mL of DMF was added. The resulting mixture was stirred for 2 h at RT and then quenched with water. The mixture was extracted with EtOAc, dried with $MgSO_4$, filtered, and concentrated. The residue was purified by silica gel chromatography using a hexanes/EtOAc gradient to give the title product. $^1H$ NMR ($CDCl_3$, 500 MHz): δ 7.66 (1H, s), 4.88 (1H, s), 3.87 (3H, s), 2.49 (3H, s), 1.92 (3H, s). m/z=234 (M+H).

INTERMEDIATE 5

Ethyl 3,3-dicyano-2-methyl-2-(5-methyl-1,2,4-oxadiazol-3-yl)propanoate

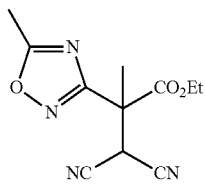 [SMILES: CCOC(=O)C(C)(c1noc(C)n1)C(C#N)C#N]

Step A

Ethyl (3Z)-3-amino-3-(hydroxyimino)-2-methylpropanoate

Ethyl 2-methylcyanoacetate (5 g, 39 mmol) and hydroxylamine (2.6 g, 39 mmol) were dissolved in 50 mL of MeOH. The solution was heated at the 50° C. overnight. The solution was then concentrated and the residue purified by silica gel chromatography using a hexanes/EtOAc gradient to give the title product.

Step B

Ethyl 2-(5-methyl-1,2,4-oxadiazol-3-yl)propanoate

Acetic anhydride (4.6 mL, 49 mmol) was added to a pyridine (50 mL) solution of the intermediate from Step A (2.6 g, 16.2 mmol). The solution was heated at reflux for 1 h and then at RT overnight. The solution was then concentrated to remove most of the pyridine. The concentrated solution was diluted with EtOAc and washed twice with water. The organic layer was concentrated and the residue purified by silica gel chromatography using a hexanes/EtOAc gradient to give the title product.

Step C

Ethyl 2-bromo-2-(5-methyl-1,2,4-oxadiazol-3-yl)propanoate

A CCl$_4$ (30 mL) solution containing the intermediate from Step B (1.9 g, 10.3 mmol), NBS (3.56 g, 20 mmol) and AIBN (0.1 g) was heated at reflux for 4 h. The solution was cooled to RT, filtered and concentrated. The residue was purified by silica gel chromatography using a hexanes/EtOAc gradient to give the title product.

Step D

Ethyl 3,3-dicyano-2-methyl-2-(5-methyl-1,2,4-oxadiazol-3-yl)propanoate

DBU (2.56 mL, 8.1 mmol) was added dropwise to a −78° C. THF (20 mL) solution of malononitrile (1.12 g, 17 mmol) and the intermediate from Step C (1.49 g, 5.66 mmol). The reaction solution was stirred at −78° C. for 15 min and then at RT for 1 h. The solution was then concentrated and the residue purified by silica gel chromatography using a hexanes/EtOAc gradient to afford the title product as the racemate. $^1$H NMR δ (ppm)(CHCl$_3$-d): 4.79 (1H, s), 4.30 (2H, dd, J=7.1, 2.6 Hz), 2.64 (3H, s), 2.02 (3H, s), 1.31-1.25 (3H, m).

INTERMEDIATE 6

Methyl 3,3-dicyano-2-(5-cyclopropyl-1,2,4-oxadiazol-3-yl)-2-methylpropanoate

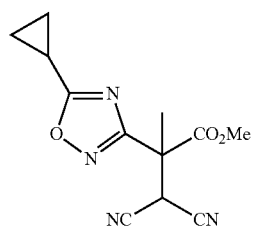 [SMILES: COC(=O)C(C)(c1noc(C2CC2)n1)C(C#N)C#N]

Step A

Methyl 3,3-dicyano-2-(5-cyclopropyl-1,2,4-oxadiazol-3-yl)-2-methylpropanoate t-Butyl methyl malonate (12.35 g, 71.0 mmol) and N'-hydroxycyclopropanecarboximidamide (3.55g, 35.5 mmol) were combined and the reaction was heated to 120° C. for 5 h. The reaction was cooled to RT and directly purified by silica chromatography using a 0 to 30% EtOAc in hexanes gradient to afford the title product.

Step B

Methyl 3,3-dicyano-2-(5-cyclopropyl-1,2,4-oxadiazol-3-yl)-2-methylpropanoate

The title compound was prepared analogous to steps B through D of I-5. $^1$H NMR (500 MHz, CDCl$_3$): δ 4.79 (1H, s), 3.90 (3H, s), 2.18-2.12 (1H, m), 2.07 (3H, s), 1.17-1.07 (4H, m).

INTERMEDIATE 7

Methyl 4-(1,1-dicyano-3-methoxy-2-methyl-3-oxopropan-2-yl)picolinate

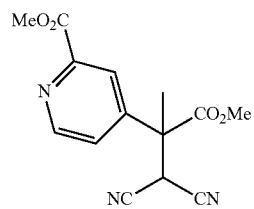 [SMILES: COC(=O)c1cc(C(C)(C(=O)OC)C(C#N)C#N)ccn1]

Step A

Methyl 2-(2-bromopyridin-4-yl)acetate 2-(2-Bromopyridin-4-yl)acetic acid (5 g, 23.1 mmol), benzene (40.5 ml) and MeOH (5.8 ml) were added to a 250 mL flask, then trimethylsilyldiazomethane (11.6 ml, 23.1 mmol, 2 M) was added dropwise over 5 min. The reaction was concentrated in vacuo. Silica gel chromatography using a hexanes/EtOAc gradient (0-100%) afforded the title compound.

Step B

Methyl 4-(2-methoxy-2-oxoethyl)picolinate

The intermediate from Step A (2g, 8.7 mmol), Pd(OAc)$_2$ (0.468 g, 2.1 mmol), DMF (43.5 ml) and dppf (2.31 g, 4.17 mmol) were added to a 100 mL flask. The flask was purged with N$_2$ three times. Hunig's base (7.59 ml, 43.5 mmol) and MeOH (31.7 ml, 782 mmol) were added via syringe. The flask was purged with N$_2$ three times, then was switched to a balloon with CO gas. The flask was vacuumed and refilled with CO three times, and was heated to 75° C. under CO balloon (1 atm) for 4 h. The reaction was cooled to RT and diluted with EtOAc (50 mL), then filtered through a syringe filter. The filtrate was washed with water (50 mL), brine (50 mL), dried with MgSO$_4$, filtered and concentrated under reduced pressure. Silica gel chromatography using a hexanes/EtOAc gradient (0-100%) afforded the title product.

Step C

Methyl 4-(1-methoxy-1-oxopropan-2-yl)picolinate

LHMDS (5.26 ml, 5.26 mmol, 1 M) was added to a 40 mL vial and cooled down to 0° C. under N$_2$. The Intermediate from Step B (1.1 g, 5.26 mmol) in THF (10.5 ml) was added dropwise via syringe over 10 min, and stirred at 0° C. for 1 h. Neat MeI (0.329 ml, 5.26 mmol) was added via syringe dropwise. After stirring at 0° C. for 45 min, the reaction was concentrated under reduced pressure. Silica gel chromatography using a hexanes/EtOAc gradient (0-100%) afforded the title product.

Step D

Methyl 4-(2-bromo-1-methoxy-1-oxopropan-2-yl)picolinate

To a 100 mL flask, intermediate from Step C (600 mg, 2.15 mmol 80%), acetonitrile (13.4 mL), magnesium perchlorate (316 mg, 1.4 mmol) were added and stirred at RT for 5 min. NBS (928 mg, 5.2 mmol) was added and heated to 50° C. for 48 h. The reaction was cooled to RT, diluted with EtOAc (50 mL), washed with $NaHCO_3$ saturated solution (30 mL), brine (30 mL), dried with $MgSO_4$, filtered and concentrated under reduced pressure. Silica gel chromatography using a hexanes/EtOAc gradient (0-100%) afforded the title product.

Step E

Methyl 4-(1,1-dicyano-3-methoxy-2-methyl-3-oxopropan-2-yl)picolinate

Sodium hydride (53.7 mg, 1.34 mmol) and DMF (5 mL) were added to a 40 mL vial, and cooled down to 0° C. under $N_2$. Malononitrile (89 mg, 1.34 mmol) in DMF (5 mL) was added dropwise over 5 min and the mixture was stirred at 0° C. for 15 min. The intermediate from Step D (390 mg, 1.03 mmol) in DMF (5 mL) was added dropwise over 5 min. The reaction was warmed up slowly to RT over 3 h. The reaction was quenched by ice-cold $NH_4Cl$ saturated solution (50 mL), then extracted with EtOAc (50 mL). The organic phase was washed with brine (50 mL) dried with $MgSO_4$, filtered and concentrated under reduced pressure. Silica gel chromatography using a hexanes/EtOAc gradient (0-100%) afforded the title product. $^1$H NMR (500 MHz, $CDCl_3$): δ 8.89 (1H, d, J=5.0 Hz), 8.17 (1H, d, J=2.0 Hz), 7.53 (1H, dd, J=5.0, 2.0 Hz), 4.60 (1H, s), 4.07 (3H, s), 3.88 (3H, s), 2.09 (3H, s), m/z=288.01 (M+1).

INTERMEDIATE 8

Ethyl 3,3-dicyano-2-methyl-2-(5-methylthiophen-2-yl)propanoate and the S and R isomers thereof

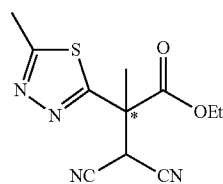 [SMILES: CCOC(=O)C(C)(c1nnc(C)s1)C(C#N)C#N]

Step A

2-Bromo-5-methyl-1,3,4-thiadiazole

Into a 250-mL 3-necked round-bottom flask were placed 5-methyl-1,3,4-thiadiazol-2-amine (20.0 g, 173.68 mmol, 1.0 equiv) and $HBr/H_2O$ (50 mL). This was followed by the addition of $Br_2$ (50 mL) dropwise with stirring at 0° C. To this was added a solution of $NaNO_2$ (30.4 g, 440.58 mmol, 2.5 equiv) in water (50 mL) dropwise with stirring at 0-10° C. The resulting solution was stirred for 1 h at 0° C. in a water/ice bath. The reaction was then quenched by the addition of $Na_2S_2O_3$ (sat., 100 mL). The pH value of the solution was adjusted to 8-9 with sodium hydroxide (4 N). The resulting solution was extracted with DCM (3×500 mL) and the organic layers were combined, dried over anhydrous sodium sulfate and filtered. The filtrate was concentrated in vacuo to dryness to afford the title product.

Step B 1,3-Diethyl 2-(5-methyl-1,3,4-thiadiazol-2-yl)propanedioate

Into a 1-L 3-necked round-bottom flask were placed the intermediate from Step A (23 g, 128.46 mmol, 1.0 equiv), 1,3-diethyl propanedioate (62.0 g, 387.1 mmol, 3.0 equiv), $Cs_2CO_3$ (168 g, 515.34 mmol, 4.0 equiv), CuI (4.9 g, 25.73 mmol, 0.2 equiv), pyridine-2-carboxylic acid (6.36 g, 51.66 mmol, 0.4 equiv) and dioxane (400 mL). The resulting mixture was stirred for 16 h at 100° C. in an oil bath. The solid was filtered out. The resulting mixture was diluted with EtOAc (1 L), washed with brine (3×500 mL), dried over anhydrous sodium sulfate and filtered. The filtrate was concentrated in vacuo to dryness. The residue was purified by silica chromatography using EtOAc/petroleum ether (1/20) to give the title product.

Step C

Ethyl 2-(5-methyl-1,3,4-thiadiazol-2-yl)acetate

Into a 250-mL round-bottom flask, were placed the intermediate from Step B (12 g, 46.46 mmol, 1.0 equiv), DMSO (150 mL), NaCl (5.4 g, 92.4 mmol, 2.0 equiv), and water (1.68 g, 2.0 equiv). The resulting mixture was stirred for 30 min at 180° C. in an oil bath. The resulting solution was diluted with EtOAc (1 L). The resulting mixture was washed with brine (3×300 mL), dried over anhydrous sodium sulfate and filtered. The filtrate was concentrated in vacuo to dryness. The residue was purified by silica chromatography using DCM/MeOH (30/1) to afford the title product.

Step D

Ethyl 2-(5-methyl-1,3,4-thiadiazol-2-yl)propanoate

Into a 250-mL 3-necked round-bottom flask purged and maintained with an inert atmosphere of nitrogen, was placed a solution of LiHMDS (5.4 mL, 1 N in THF, 1.0 equiv) in THF (50 mL). This was followed by the addition of the intermediate from Step C (1.0 g, 5.37 mmol, 1.0 equiv) dropwise with stirring at 0° C. The resulting mixture was stirred for 30 min at 0° C. To this was added a solution of iodomethane (760 mg, 5.35 mmol, 1.0 equiv) in THF (50 mL) dropwise with stirring at −20° C. The resulting solution was stirred for 2 h at −20° C. The reaction was then quenched by the addition of $NH_4Cl$ (sat., 200 mL). The resulting solution was extracted with EtOAc (3×100 mL). The organic layers were combined, dried over anhydrous sodium sulfate and filtered. The filtrate was concentrated in vacuo to dryness. The residue was purified by silica chromatography using EtOAc/petroleum ether (2/1) to afford the title product.

Step E

Ethyl 2-bromo-2-(5-methyl-1,3,4-thiadiazol-2-yl)propanoate

Into a 100-mL 3-necked round-bottom flask purged and maintained with an inert atmosphere of nitrogen, was placed a solution of the intermediate from Step D (300 mg, 1.5 mmol, 1.0 equiv) in THF (20 mL). This was followed by the addition of LiHMDS (1.8 mL, 1 N in THF, 1.2 equiv) dropwise with stirring at −78° C. in 30 min. To this was added NBS (374 mg, 2.1 mmol, 1.4 equiv). The resulting solution was stirred for 1 h at RT. The reaction was then quenched by the addition of NH$_4$Cl (sat., 100 mL). The resulting solution was extracted with EtOAc (3×100 mL). The organic layers were combined, dried over sodium sulfate and filtered. The filtrate was concentrated in vacuo to dryness. The residue was purified by silica chromatography using EtOAc/petroleum ether (1/5) to give the title product.

Step F

Ethyl 3,3-dicyano-2-methyl-2-(5-methyl-1,3,4-thiadiazol-2-yl)propanoate

Into a 8-mL round-bottom flask, were placed the intermediate from Step E (350 mg, 1.25 mmol, 1.0 equiv), malononitrile (165 mg, 2.5 mmol, 2.0 equiv), DMSO (4 mL), potassium carbonate (173 mg, 1.24 mmol, 1.0 equiv) and THF (1 mL). The resulting mixture was stirred for 1 h at 0° C. in a water/ice bath. The reaction was then quenched by the addition of brine (10 mL). The pH value of the solution was adjusted to 3-4 with aq. HCl (1 N). The resulting solution was extracted with EtOAc (3×50 mL). The organic layers were combined, dried over anhydrous sodium sulfate and filtered. The filtrate was concentrated in vacuo to dryness. The residue was applied onto a silica gel column with DCM/petroleum ether (1/1). The racemic material was resolved via chiral chromatography (IA column) to afford isomers I-8A (faster eluting) and I-8B (slower eluting) MS (ES, m/z) 265 [M+1]

INTERMEDIATE 9

Ethyl 3,3-dicyano-2-methyl-2-(5-methyl-1,3,4-oxadiazol-2-yl)propanoate, and the S and R isomers thereof

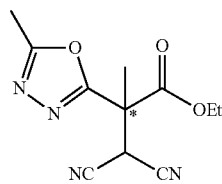 [SMILES: CCOC(=O)C(C)(c1nnc(C)o1)C(C#N)C#N]

Step A

Ethyl 2-(5-methyl-1,3,4-oxadiazol-2-yl)propanoate

Into a 100-mL round-bottom flask, were placed a solution of ethyl 2-(1H-1,2,3,4-tetrazol-5-yl) propanoate (prepared analogous to *J. Med. Chem.* 1996, 39 (12), 2354, from commercially available 2-ethyl 2-cyanopropanoate) (5 g, 29.38 mmol, 1.0 equiv) in toluene (20 mL). This was followed by the addition of acetyl acetate (4.5 g, 44.08 mmol, 1.3 equiv) in toluene (10 mL) dropwise with stirring at RT. The resulting solution was stirred 16 h at 110° C. The pH value of the solution was adjusted to 8 with sodium carbonate (sat.). The resulting solution was extracted with DCM (3×100 mL). The organic layers were combined, dried over anhydrous sodium sulfate and filtrated. The filtrate was concentrated in vacuo to dryness. The residue was purified by silica chromatography using EtOAc/petroleum ether (3:1) to afford the title product

Step B

Ethyl 2-bromo-2-(5-methyl-1,3,4-oxadiazol-2-yl)propanoate

Into a 100-mL 3-necked round-bottom flask purged and maintained with an inert atmosphere of nitrogen, was placed a solution of the intermediate from Step A (3.5 g, 19.0 mmol, 1.0 equiv) in THF (30 mL). This was followed by the addition of LiHMDS (3.8 g, 22.71 mmol, 1.2 equiv) dropwise with stirring at 0° C. The reaction mixture was stirred for 30 min at 0° C. To this was added NBS (4.7 g, 1.40 equiv). The resulting solution was stirred for 0.5 h at 0° C. and additional 0.5 h at 25° C. The reaction was then quenched by the addition of sodium thiosulfatepentahydrate (sat., 50 mL). The resulting solution was extracted with ether (3×100 mL). The organic layers were combined, dried over anhydrous sodium sulfate and filtrated. The filtrate was concentrated in vacuo to dryness. The residue was purified by silica chromatography using EtOAc/petroleum ether (3/1) to give the title product

Step C

Ethyl 3,3-dicyano-2-methyl-2-(5-methyl-1,3,4-oxadiazol-2-yl)propanoate

Into a 100-mL round-bottom flask, were placed the intermediate from Step B (2.7 g, 10.26 mmol, 1.0 equiv), propanedinitrile (1.4 g, 20.44 mmol, 2.0 equiv), DMSO (30 mL). This was followed by the addition of potassium carbonate (1.4g, 9.98 mmol, 1.0 equiv) in several batches at 10° C. The resulting mixture was stirred for 2 h at RT. The resulting mixture was quenched by the addition of water (50 mL). The pH value of the solution was adjusted to 3-4 with aq HCl (1 N). The resulting solution was extracted with EtOAc (2×50 mL) and the organic layers were combined, dried over anhydrous sodium sulfate and filtrated. The filtrate was concentrated in vacuo to dryness. The residue was purified by silica chromatography using EtOAc/petroleum ether (0%-50%). The racemic material was resolved via chiral chromatography (AD-H column) to afford isomers I-9A (faster eluting) and I-9B (slower eluting). $^1$H NMR (300 MHz, CDCl$_3$, ppm): δ 4.80 (s, 1H), 4.33 (q, J=7.2 Hz, 2H), 2.60 (s, 3H), 2.05 (s, 3H), 1.31 (t, J=7.2 Hz, 3H).

INTERMEDIATE 10

Ethyl 3,3-dicyano-2-(5-cyclopropyl-1,3,4-oxadiazol-2-yl)-2-methylpropanoate and the S and R isomers thereof

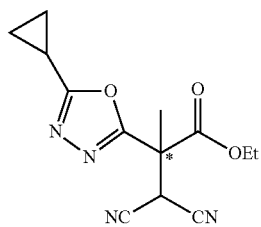 [SMILES: CCOC(=O)C(C)(c1nnc(C2CC2)o1)C(C#N)C#N]

Step A

Ethyl 2-(5-cyclopropyl-1,3,4-oxadiazol-2-yl)propanoate

Into a 100-mL round-bottom flask were placed ethyl 2-(1H-1,2,3,4-tetrazol-5-yl)propanoate (prepared analogous to *J. Med. Chem.* 1996, 39 (12), 2354 from commercially available 2-ethyl 2-cyanopropanoate) (10 g, 58.8 mmol, 1.0 equiv) and pyridine (40 mL). This was followed by the addition of cyclopropanecarbonyl chloride (8 g, 76.5 mmol, 1.3 equiv) dropwise with stirring at ambient temperature. The resulting solution was stirred for 2 h at ambient temperature, and then heated to reflux for 4 h. The reaction was then quenched by the addition of water (150 mL). The resulting solution was extracted with ether (3×100 mL) and the organic layers were combined, washed with aq. HCl (1 N, 3×100 mL) and brine (100 mL), dried over anhydrous sodium sulfate and filtered. The filtrate was concentrated under vacuum to afford the title product.

Step B

Ethyl 2-bromo-2-(5-cyclopropyl-1,3,4-oxadiazol-2-yl)propanoate

Into a 100-mL 3-necked round-bottom flask purged and maintained with an inert atmosphere of $N_2$ were placed the intermediate from Step A (2.5 g, 11.89 mmol, 1.0 equiv) and THF (30 mL). This was followed by the addition of LiHMDS (14.3 mL, 1.2 equiv, 1 N) dropwise with stirring at 0° C. The resulting solution was stirred for 0.5 h at 0° C. To this was added NBS (2.9 g, 16.57 mmol, 1.4 equiv). The resulting solution was stirred for 1.5 h at ambient temperature. The reaction was then quenched by the addition of 80 mL of $Na_2S_2O_3$ (sat.). The resulting solution was extracted with ether (3×100 Ml) and the organic layers were combined. The resulting mixture was washed with $Na_2S_2O_3$ (2×50 mL) and brine (50 mL). The mixture was dried over anhydrous sodium sulfate and filtered. The filtrate was concentrated under vacuum to afford the title product.

Step C

Ethyl 3,3-dicyano-2-(5-cyclopropyl-1,3,4-oxadiazol-2-yl)-2-methylpropanoate

Into a 250-mL 3-necked round-bottom flask purged and maintained with an inert atmosphere of nitrogen were placed the intermediate from Step B (8 g, 27.67 mmol, 1.0 equiv), DMSO (80 mL), THF (20 mL), and propanedinitrile (3.65 g, 55.25 mmol, 2.0 equiv). This was followed by the addition of potassium carbonate (3.82 g, 27.64 mmol, 1.0 equiv) in portions at 0° C. The resulting solution was stirred for 0.5 h at 0° C. The reaction progress was monitored by LCMS. The reaction was then quenched by the addition of water/ice (200 mL). The pH value of the solution was adjusted to 5 with aq. HCl (2 N). The resulting solution was extracted with EtOAc (4×150 mL) and the organic layers were combined, washed with brine (150 mL), dried over anhydrous sodium sulfate and filtered. The filtrate was concentrated under vacuum. The residue was purified by silica chromatography using MeOH/DCM (0%-1%). The racemic material was resolved via chiral chromatography (IA column): MS (ES, m/z); 275 [M+1]⁺ to afford isomers I-10A (faster eluting) and I-10B (slower eluting).

Using essentially the same procedures described for the synthesis of Intermediates 1 to 10, the following compounds in Table 1 were made.

TABLE 1

| INT. | Chiral Resolution Column | R¹ | R² | MS or ¹H NMR |
|---|---|---|---|---|
| 11 | OD column | quinoline | Me | m/z (M + H) 280 |
| 12 | AD column | pyrimidine | Et | m/z (M + H) 245 |

TABLE 1-continued

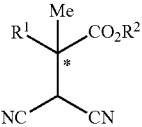

| INT. | Chiral Resolution Column | R¹ | R² | MS or ¹H NMR |
|---|---|---|---|---|
| 13 | CHIRALPAK IA | 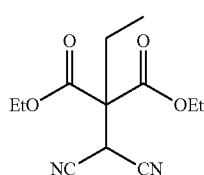 | Et | m/z (M + H) 278.2 |
| 14 | N/A (not applicable) | —CO₂Et | Et | ¹H NMR δ (ppm)(500 MHz, CDCl₃): δ 4.55 (1 H, s), 4.30-4.37 (4 H, m), 1.82 (3H, s), 1.34 (6 H, t, J = 7.12 Hz) |

INTERMEDIATE 15

Diethyl 2-(dicyanomethyl)-2-ethylmalonate

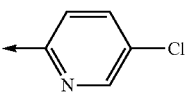

Diethyl 2-(dicyanomethylene)malonate (prepared analogous to Sentman et. al. *J. Org. Chem.* 1982, 47, 4577) (2 g, 9 mmol) was dissolved in THF (23 mL) and cooled to −25° C. and ethylmagnesium bromide (3.0 M, 5.10 mL, 15.3 mmol) was added dropwise. The reaction was transferred to a 0° C. bath and stirred for an additional h. The mixture was quenched with sat'd aq. ammonium chloride at 0° C. and diluted with EtOAc and water. The layers were separated and the organic layer was dried (anhydrous sodium sulfate) and concentrated. Silica gel chromatography using a hexanes/EtOAc gradient afforded the title product. ¹H NMR (500 MHz, CDCl₃): δ 4.42 (1H, s), 4.30-4.32 (4H, m), 2.24 (2H, d, J=7.58 Hz), 1.30 (6H, t, J=7.08 Hz), 1.04 (3H, t, J=7.47 Hz).

INTERMEDIATE 16

Diethyl 2-(dicyanomethyl)-2-isopropylmalonate

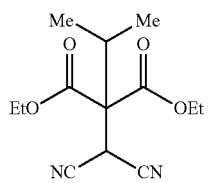

Diethyl 2-(dicyanomethylene)malonate (prepared analogous to Sentman et. al. *J. Org. Chem.* 1982, 47, 4577) (1 g, 4.5 mmol) was dissolved in THF (9 mL), cooled to −25° C. and isopropylmagnesium chloride lithium chloride complex (1.3 M, 5.19 mL, 6.75 mmol) was added dropwise. The reaction was stirred at −25° C. for 1 h, then slowly warmed to RT over an additional 2 h. The mixture was quenched with sat'd aq. ammonium chloride at RT and diluted with EtOAc and brine. The layers were separated and the organic layer was dried (anhydrous sodium sulfate), filtered and concentrated. Silica gel chromatography using a hexanes/EtOAc gradient afforded the title product. ¹H NMR (500 MHz, CDCl₃): δ 4.48 (1H, s), 4.38 (4H, q, J=7.15 Hz), 2.75-2.76 (1H, m), 1.37 (6H, t, J=7.18 Hz), 1.17 (6H, d, J=6.94 Hz).

INTERMEDIATE 17

Diethyl cyclopropyl (dicyanomethyl)propanedioate

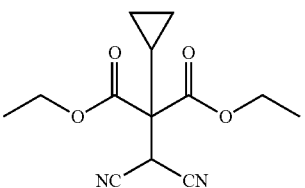 [SMILES: CCOC(=O)C(C(=O)OCC)(C(C#N)C#N)C1CC1]

A THF (45.0 ml) solution of diethyl (dicyanomethylidene)propanedioate (prepared analogous to Sentman et. al. *J. Org. Chem.* 1982, 47, 4577) (4.50 ml, 4.5 mmol, 1M solution in benzene) was cooled to 0° C. and cyclopropylmagnesium bromide (9.00 ml, 4.50 mmol) and LiCl (0.191 g, 4.5 mmol) were added. The reaction was stirred at 0° C. for 2 h and then warmed to RT while stirring for an additional 2 h. The reaction was diluted with EtOAc and quenched with saturated aq. NH₄Cl. The layers were separated and the organic layer dried (MgSO₄), filtered, and concentrated in vacuo. Purification by silica gel column chromatography using a hexanes/EtOAc gradient afforded the title product. ¹H NMR (500 MHz, CDCl₃): δ 4.41 (1H, s), 4.38-4.26 (4H, m), 1.52-1.45 (1H, m), 1.33 (6H, t, J=7.14 Hz), 0.86-0.79 (2H, m), 0.71-0.66 (2H, m).

INTERMEDIATE 18

Ethyl-2-(dicyanomethyl))-2-methylbut-3-ynoate and the S and R isomers thereof

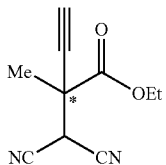

To a flask containing anhydrous LiCl (25.8 mg, 0.609 mmol) in THF (1 mL), was added a solution of ethynylmagnesium bromide (1.3 mL, 0.64 mmol, 0.5 M in THF). The reaction was stirred at RT for 25 min. The resulting solution was then quickly added dropwise via syringe to a solution of ethyl 3,3-dicyano-2-methylprop-2-enoate (prepared according to Hagiware et. al. *Synthesis* 1974, 9, 669) (0.609 mL, 0.609 mmol, 1M solution in benzene) in THF (22.5 mL) at −10 to −20° C. The reaction was stirred for 10 min in the cooling bath then quenched with sat'd aq. $NH_4^+$ Cl—, and then diluted with water and EtOAc. The layers were separated and the organic layer was dried (over sodium sulfate) and concentrated. The residue was purified by silica gel chromatography using a hexanes/EtOAc gradient to give the title product. The title product was resolved via chiral chromatography (OJ-H) to afford isomers I-18A (faster eluting) and I-18B (slower eluting). $^1$H NMR (499 MHz, $CDCl_3$): δ 4.34 (q, =7.17 Hz, 2H), 4.31 (s, 1H), 2.66 (s, 1H), 1.80 (s, 3H), 1.35 (t, J=7.14 Hz, 3H).

INTERMEDIATE 19

Methyl 2-cyclopropyl-2-(dicyanomethyl)but-3-ynoate

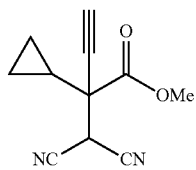

Step A methyl 3,3-dicyano-2-cyclopropylacrylate

A mixture of methyl 2-cyclopropyl-2-oxoacetate (prepared similarly to: *Russian Chemical Bulletin* 2007 56, 1515-1521) (800 mg, 6.24 mmol) and malononitrile (516 mg, 7.8 mmol) was stirred for 2-3 min. A solution of beta-alanine (27.8 mg, 0.312 mmol) in water (535 μl) was added in small portions over ~5 min period. The reaction was cooled in an ice-bath and EtOH (350 μl) was added. The reaction was stirred at RT for 24 h. The reaction was diluted with water and extracted with ethyl ether. The ether layer was back extracted 2× with water. The ether layer was further diluted with EtOAc and dried (over sodium sulfate).

The combined organic layers were purified by silica gel column chromatography using a hexanes/EtOAc gradient to give the title product.

Step B methyl 2-cyclopropyl-2-(dicyanomethyl)but-3-ynoate

To a flask containing anhydrous LiCl (144 mg, 3.41 mmol) in THF (2 mL) was added a solution of ethynylmagnesium bromide (6.8 mL, 3.41 mmol, 0.5M in THF). The reaction was stirred at RT for 30 min. The resulting solution was cooled to −30° C. A solution of the intermediate from Step A (0.500 g, 2.84 mmol) in THF (5 mL) was added. The reaction was stirred for 1 h in a cooling bath then raised up to RT slowly. The mixture was quenched with saturated aq. $NH_4Cl$, and then diluted with water and EtOAc. The layers were separated and the organic layer was dried with sodium sulfate and concentrated in vacuo. Purification by silica gel column chromatography using a hexanes/EtOAc gradient afforded the title product. $^1$H NMR (500 MHz, $CDCl_3$): δ 4.41 (1H, s), 3.93 (3H, s), 2.63 (1H, s), 1.31-1.24 (1H, m), 1.03-0.96 (1H, m), 0.92-0.79 (2H, m), 0.77-0.67 (1H, m).

INTERMEDIATE 20

Methyl 2-(dicyanomethyl)-2-ethylbut-3-ynoate

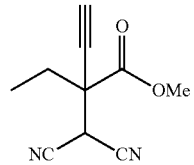

Step A

Methyl 2-(dicyanomethylene) butanoate

Methyl 2-oxobutanoate (15 g, 129 mmol) and malononitrile (12.80 g, 194 mmol) were added to a flask followed by the addition of 3-aminopropanoic acid (0.575 g, 6.46 mmol) as a solution in water (12.92 mL). EtOH (12.92 mL) was added and the reaction was stirred for 2 h. The mixture was diluted with EtOAc and water. The layers were separated and the organic layer was dried (anhydrous sodium sulfate), filtered and concentrated. Silica gel chromatography using a hexanes/EtOAc gradient afforded the title product.

Step B

Methyl 2-(dicyanomethyl)-2-ethylbut-3-ynoate

Ethynylmagnesium bromide (0.5 M, 4.20 mL, 2.1 mmol) was quickly added dropwise to a mixture of the intermediate from Step A (0.23 g, 1.40 mmol) in THF (3.5 mL) at −50° C. The mixture was slowly warmed in the bath for 30 min. The reaction was quenched with saturated aq. $NH_4Cl$ and extracted with EtOAc. The organic phase was washed with brine, dried (anhydrous $MgSO_4$), filtered, and concentrated. The residue was purified by silica gel chromatography using a hexanes/EtOAc gradient to give the title product. $^1$H NMR (500 MHz, CDCl₃): δ 4.28 (1H, s), 3.84 (3H, s), 2.68 (1H, s), 2.06-2.07 (2H, m), 1.03 (3H, t, J=7.44 Hz).

INTERMEDIATE 21

Methyl 3,3-dicyano-2-cyclopropyl-2-(oxazol-2-yl)propanoate

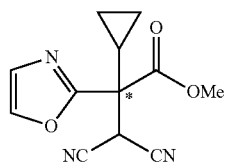 [SMILES: COC(=O)C(c1ncco1)(C(C#N)C#N)C1CC1]

To oxazole (0.862 g, 12.49 mmol) in THF (28.4 mL) at −78° C. was added n-BuLi (5.45 mL, 13.62 mmol, 2.5 M in hexane) dropwise. The reaction was stirred at −78° C. for 30 min and a solution of the intermediate from Step A of I-19 (2 g, 11.35 mmol) in THF (10 mL) was added. The resulting mixture was stirred below −15° C. for 1.5 h, quenched with ice-cold saturated aq. NH₄Cl, then extracted with EtOAc. The organic layer was dried with MgSO₄, filtered, and concentrated in vacuo. Purification by silica gel column chromatography using a hexanes/EtOAc gradient (0-30% EtOAc/Hexane) afforded the title product. ¹H NMR (500 MHz, CDCl₃): δ 7.97 (1H, s), 7.93 (1H, s), 4.89 (1H, s), 3.93 (3H, s), 0.89 (2H, m), 0.72 (1H, m), 0.64 (1H, m), 0.45 (1H, m), m/z=246.12 (M+1). The racemic material was resolved via chiral SFC (AD-H) to obtain isomer I-21A (faster eluting) and isomer I-21B (slower eluting).

INTERMEDIATE 22

Methyl 3,3-dicyano-2-cyclopropyl-2-(isoxazol-4-yl)propanoate

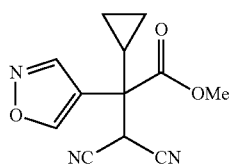 [SMILES: COC(=O)C(c1cnoc1)(C(C#N)C#N)C1CC1]

Isopropyl magnesium chloride lithium chloride complex (2.62 ml, 3.41 mmol) was added dropwise to 4-iodoisoxazole (0.609 g, 3.12 mmol) in THF (10 mL) at 0° C. and the mixture was stirred for 1 h, during which time the temperature rose to 18° C. A solution of methyl 3,3-dicyano-2-cyclopropylacrylate (see Step A of I-19) (0.5 g, 2.84 mmol) in THF (3 mL) was added at 0° C. The resulting mixture was allowed to rise to RT slowly and stirred for 4 h, then was quenched with ice-cold saturated aq. NH₄Cl and extracted with EtOAc. The organic layer was dried with MgSO₄, filtered, and concentrated in vacuo. Purification by silica gel column chromatography using a hexanes/EtOAc gradient (0-100% EtOAc/Hexane) afforded the title product. ¹H NMR (500 MHz, CDCl₃): δ 8.74 (1H, s), 8.53 (1H, s), 4.59 (1H, s), 3.89 (3H, s), 1.08 (1H, m), 0.91 (2H, m), 0.61 (1H, m), 0.52 (1H, m), m/z=246.13 (M+1).

INTERMEDIATE 23

Methyl-3,3-dicyano-2-cyclopropyl-2-(1-isopropyl-1H-pyrazol-3-yl)propanoate

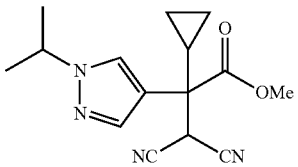 [SMILES: COC(=O)C(c1cnn(C(C)C)c1)(C(C#N)C#N)C1CC1]

Isopropylmagnesium chloride-lithium chloride complex (5.24 ml, 6.81 mmol) was added dropwise to 4-iodoisopropyl-1H-pyrazole (1.535 g, 6.24 mmol) in THF (10 mL) at 0° C. and the reaction was warmed to RT and stirred for a total of 2 h. A solution of methyl 3,3-dicyano-2-cyclopropylacrylate (see Step A of I-19) (1 g, 5.68 mmol) in THF (4 mL) was added at 0° C. The resulting mixture was allowed to rise to RT slowly and stirred overnight, then was quenched with ice-cold saturated aq. NH₄Cl and extracted with EtOAc. The organic layer was dried with MgSO₄, filtered, and concentrated in vacuo. Purification by silica gel column chromatography using a hexanes/EtOAc gradient (0-100% EtOAc/Hexane) afforded the title product. ¹H NMR (500 MHz, CDCl₃): δ 7.59 (2H, s), 4.47 (1H, s), 4.16 (1H, m), 3.86 (3H, s), 1.56 (6H, d, J=5 Hz), 0.91 (1H, m), 0.81 (2H, m), 0.64 (1H, m), 0.46 (1H, m), m/z=287.13 (M+1).

INTERMEDIATE 24

Methyl-3,3-dicyano-2-(5-methoxypyridin-3-yl)-2-methylpropanoate and the S and R isomers thereof

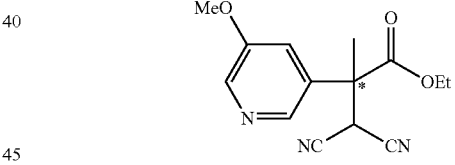

To 3-bromo-5-methoxypyridine (0.756 g, 4.02 mmol) in toluene (12 mL) and THF (3 mL) at −78° C. was added n-BuLi (1.61 mL, 4.02 mmol, 2.5 M in hexane) dropwise. The reaction was stirred at −78° C. for 30 min and then a solution of ethyl 3,3-dicyano-2-methylprop-2-enoate (prepared according to Hagiware et. al. *Synthesis* 1974, 9, 669) (0.6 g, 3.65 mmol) in benzene (1.2 mL) was added. The resulting mixture was warmed to RT and quenched with saturated aq. NH₄Cl and extracted with EtOAc. The organic layer was dried with MgSO₄, filtered, and concentrated in vacuo. Purification by silica gel column chromatography using a hexanes/EtOAc gradient afforded the title product. ¹H NMR (500 MHz, CDCl₃): δ 8.39 (1H, d, J=2.66 Hz), 8.29 (1H, d, J=2.00 Hz), 7.22 (1H, t, J=2.39 Hz), 4.53 (1H, s), 4.38-4.27 (2H, m), 3.93 (3H, s), 2.04 (3H, s), 1.30 (3H, t, J=7.13 Hz). The racemic material was resolved via chiral chromatography (IA-H column) to obtain isomer I-24A (faster eluting) and isomer I-24B (slower eluting).

Using essentially the same procedure described for Intermediates 15-24, the following compounds in Table 2 were made.

TABLE 2
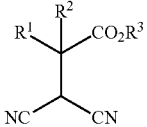
| INT. | Chiral Resolution Column | R¹ | R² | R³ | m/z (M + H) |
|---|---|---|---|---|---|
| 25 | Racemic | 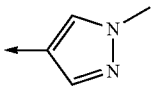 | Me |  | 259.2 |
| 26 | Racemic | 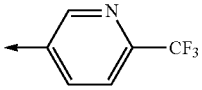 | Me | Et | See table below |
| 27 | Racemic | 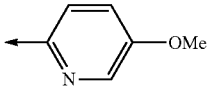 | Me | Et | 274.04 |
| 28 | Racemic | 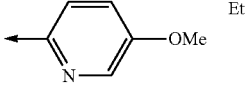 | Et | Et | 274.16 |
| 29 | Chiralpak AD column | 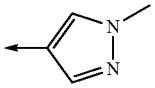 | Me | Et | 247.3 |
| 30 | Racemic | 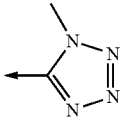 | Me |  | See table below |
| 31 | CHIRALPAK AD | 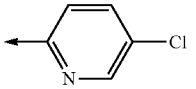 | Me |  | 290.1 |
| 32 | CHIRALPAK AD-H | 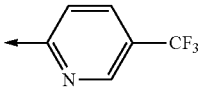 | Me |  | 322 [M − 1]⁻ |
| 33 | CHIRALPAK-AD | 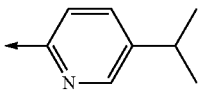 | Me | Et | 286.1 |
| INT. | Characterizaton Data |
|---|---|
| 27 | ¹H NMR δ (ppm)(CHCl₃-d): δ 8.78 (1 H, d, J = 2.35 Hz), 7.94 (1 H, dd, J = 8.40, 2.39 Hz), 7.79 (1 H, d, J = 8.34 Hz), 4.53 (1 H, s), 4.27-4.38 (2 H, m), 2.06 (3 H, s), 1.27-1.30 (3 H, m). |
| 30 | ¹H NMR δ (ppm)(CHCl₃-d): δ 4.92 (1 H, s), 4.24 (3 H, s), 3.94 (3 H, s), 1.73 (1 H, tt, J = 8.31, 5.45 Hz), 1.03-1.07 (2 H, m), 0.69-0.73 (1 H, m), 0.60-0.64 (1 H, m). |

INTERMEDIATE 34

Propyl 3-(3,3-difluorocyclobutyl)propanoate

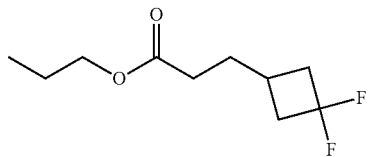

Step A 2-(3,3-difluorocyclobutyl)ethyl 4-methylbenzenesulfonate 2-(3,3-difluorocyclobutyl)ethanol (4.9 g, 36.0 mmol) was added in a flask (250 mL) in a water bath at rt, DCM (72.0 ml) was added, followed by TEA (15.05 ml, 108 mmol), DMAP (0.879 g, 7.2 mmol), and lastly TsCl (9.61 g, 50.4 mmol). The reaction was stirred at RT overnight. The mixture was poured onto ice-water (200 mL) and the water phase was extracted with EtOAc (200 mL). The organic phase was dried by $MgSO_4$, filtered and the solvent was evaporated under in vacuo. Silica gel chromatography (0-50% EtOAc in Hexanes) afforded the title compound.

Step B 3-(3,3-difluorocyclobutyl)propanenitrile 2-(3,3-difluorocyclobutyl)ethyl 4-methylbenzenesulfonate (8.88g, 30.6 mmol) and NaCN (1.649 g, 33.6 mmol) were added in a flask (100 mL), DMSO (61.2 ml) was added. flushed with $N_2$ for 2 min, then was heated to 90° C. for ~3 h, then 80° C. overnight. The reaction was cooled down to RT and added $Et_2O$ (100 mL) and water (100 mL) were added followed by 10 min. of stirring. The phases were separated and the ether layer was washed with brine (50 mL×2), dried by $MgSO_4$, filter and concentrated at RT at a pressure of 150 mmHg. The material was not concentrated completely. The title compound was carried onto the next step without further purification.

Step C propyl 3-(3,3-difluorocyclobutyl)propanoate 3-(3,3-difluorocyclobutyl)propanenitrile (4.4 g, 30.3 mmol) was added in a microwave vial (40 mL), followed by propanol (60.6 ml). HCl gas was passed through the solution for 20 min at RT, then sealed with a crimped cap. The reaction was heated to 90° C. for 2 h. The reaction was cooled to RT and the solids were filtered and rinsed with $Et_2O$ (100 mL). The filtrate was concentrated to afford the title compound in 80% purity. The material was used without further purification. $^1$H NMR (500 MHz, $CD_3OH$) δ 4.03 (t, J=6.5 Hz, 2H), 2.66-2.61 (m, 2H), 2.31 (t, J=7.5 Hz, 2H), 2.21-2.12 (m, 3H), 1.80 (q, J=7.0 Hz, 2H), 1.68-1.63 (m, 2H), 0.95 (t, J=7.0 Hz, 3H).

Using essentially the same procedure described in Steps C-F for the synthesis of Example 1 using Intermediate 34 or commercially available reagents, the following compounds in Table 3 were made.

TABLE 3

| INT. | Starting ester | $R^1$ | m/z (M + H$^+$) |
|---|---|---|---|
| I-35 | I-34 | (3,3-difluorocyclobutyl)ethyl group | 295.1 |
| I-36 | ethyl pentanoate | butyl group | 233.1 |
| I-37 | butyl 3-cyclobutylpropanoate | 2-cyclobutylethyl group | 259.2 |

TABLE 3-continued

| INT. | Starting ester | R¹ | m/z (M + H⁺) |
|---|---|---|---|
| I-38 | ethyl 2-methyl-4,4,4-trifluorobutanoate (structure) | CH(CH₃)CH₂CF₃ (structure) | 287 |

EXAMPLE 1

4-Amino-5-(5-fluoropyridin-2-yl)-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one

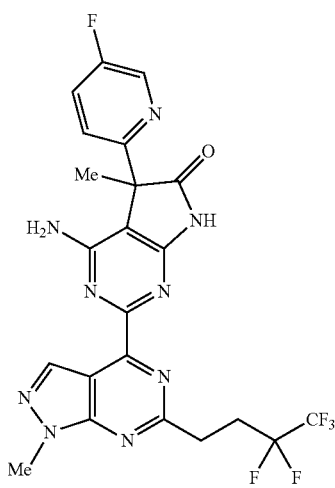 [SMILES: Cn1ncc2c(-c3nc(N)c4c(n3)NC(=O)C4(C)c3ccc(F)cn3)nc(CCC(F)(F)C(F)(F)F)nc21]

Step A

4,4,5,5,5-Pentafluoropentanoic acid

To a stirred solution of Jones reagent (chromium trioxide-H₂SO₄ complex in water) (20 ml, 160 mmol) in acetone (20 mL) at 0° C., a solution of 4,4,5,5,5-pentafluoropentan-1-ol (7.12 g, 40 mmol) in acetone (30 mL) was added dropwise. After the addition, the mixture was removed from the ice bath and was stirred continuously at RT for 1 h. The mixture was poured into ice/water and extracted with Et₂O. Crude ether mixture was extracted with aq. 2N sodium hydroxide. The inorganic layer was acidified with aq. 6 N HCl and the organic layer was extracted with Et₂O. The combined organic layers were washed with brine, dried over anhydrous sodium sulfate and concentrated in vacuo to give the title product.

Step B propyl 4,4,5,5,5-Pentafluoropentanoate

To a solution of the intermediate from Step A (25 g, 0.13 mol) in propanol (100 mL) at 0° C. was added thionyl chloride (14.9 mL, 0.195 mol). After addition, the mixture was removed from the ice bath and was stirred continuously at RT for 5 h. The solution was concentrated in vacuo. The residue was diluted with EtOAc and poured into ice water. The organic layer was washed with aq. NaHCO₃ solution, dried over Na₂SO₄, then concentrated in vacuo to give the title product.

Step C

1-Methyl-6-(3,3,4,4,4-pentafluorobutyl)-1H-pyrazolo[3,4-d]pyrimidin-4-ol

A mixture of 5-amino-1-methyl-1H-pyrazole-4-carboxamide (70 g, 0.49 mol), EtONa (117 g, 1.72 mol) and the intermediate from Step B (272 g, 1.16 mol) in EtOH (1 L) was stirred in a sealed bottle at 120° C. overnight. The mixture was concentrated and the residue was diluted with H₂O (2 L) and then adjusted to pH=6 with 2 N aq. HCl solution. The mixture was extracted with EtOAc (1 L×3). The combined organic layers were dried over Na₂SO₄, filtered and concentrated. The residue was purified by silica gel column chromatography using petroleum ether/EtOAc=1:1 to give the title product.

Step D

4-Chloro-1-methyl-6-(3,3,4,4,4-pentafluorobutyl)-1H-pyrazolo[3,4-d]pyrimidine The intermediate from Step C (43 g, 0.145 mmol) in POCl₃ (250 mL) was stirred at 115° C. overnight. The mixture was diluted with EtOAc (2 L) and then washed with H₂O (1 L×5). The organic layer was dried and concentrated in vacuo. The residue was purified by silica gel chromatography using petroleum ether/EtOAc=5:1 to give the title product.

Step E

1-Methyl-6-(3,3,4,4,4-pentafluorobutyl)-1H-pyrazolo[3,4-d]pyrimidine-4-carbonitrile The intermediate from Step D (38 g, 0.12 mol), ZnCN₂ (38 g, 0.33 mol), Pd₂(dba)₃ (3.5 g), dppf (4.3 g) in DMF (1 L) was stirred at 115° C. for 4 h. The mixture was filtered and the filtrate was concentrated in vacuo. The residue was purified by silica gel chromatography using petroleum ether/EtOAc=10:1 to give the title product.

Step F

1-Methyl-6-(3,3,4,4,4-pentafluorobutyl)-1H-pyrazolo[3,4-d]pyrimidine-4 carboximidamide Me₃Al (254 mL, 0.51 mol, 2 mol/L) was added dropwise to NH₄Cl (27 g, 0.51 mol) in toluene (1 L) and stirred at RT for 1 h. The intermediate from Step E (77.5 g, 0.25 mol) was then added and the solution was heated to 120° C. The mixture was stirred at 120° C. for 2 h, and then cooled to RT. MeOH, DCM and silica gel were added and stirred for 15 min, and then the solid was filtered off. The filtrate was concentrated and the crude solid was suspended in THF and filtered again. The filtrate was concentrated and washed with petroleum ether: EtOAc=10:1 (100 mL). The solid was dried in vacuo to get the title product Step G 4-Amino-5-(5-fluoropyridin-2-yl)-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one Into an 8-mL vial, were placed the intermediate from Step F (50 mg, 0.16 mmol, 1.0 equiv), I-2B (49 mg, 0.19 mmol, 1.2 equiv), potassium bicarbonate (19 mg, 0.19 mmol, 1.2 equiv), and t-butanol (2 mL). The resulting mixture was stirred for 16 h at 70° C. in an oil bath. The reaction was quenched by the addition of water (5 mL). The resulting solution was extracted with EtOAc (3×20 mL) and the organic layers were combined and dried over anhydrous sodium sulfate and filtered. The filtrate was concentrated in vacuo to dryness. The residue was purified by silica chromatography using EtOAc/petroleum ether (1/1). The crude product was re-crystallized from DCM/hexanes in a ratio of (1/1) to afford the title product. ¹H NMR (300 MHz, CDCl₃) δ 8.93 (brs, 1H), 8.67 (s, 1H), 8.48 (d, J=2.7 Hz, 1H), 7.61-7.55 (m, 1H), 7.49-7.43 (m, 1H), 4.16 (s, 3H), 3.58-3.52 (m, 2H), 2.94-2.77 (m, 2H), 1.93 (s, 3H); MS (ES, m/z) 538 [M+1]+.

EXAMPLE 2

4-Amino-5-(5-fluoropyridin-2-yl)-5-methyl-2-(1-(methyl-d3)-6-(3,3,4,4,4-pentafluorobutyl)-1H-pyrazolo[3,4-d]pyrimidin-4-yl)-5H-pyrrolo[2,3-d]pyrimidin-6(7H)-one-1H- and the S and R isomers thereof

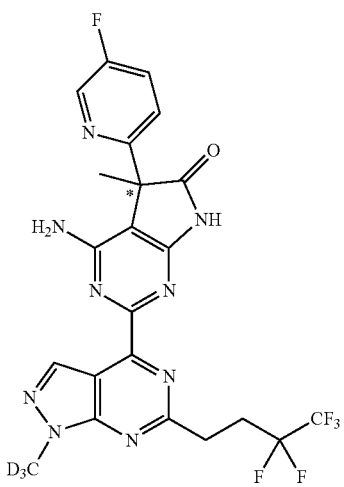 [SMILES: [2H]C([2H])([2H])n1ncc2c(-c3nc(N)c4c(n3)NC(=O)C4(C)c3ccc(F)cn3)nc(CCC(F)(F)C(F)(F)F)nc21]

Step A

5-Amino-1-(methyl-d3)-1H-pyrazole-4-carbonitrile

3-Amino-1H-pyrazole-4-carbonitrile (200 g, 1.85 mol) was dissolved in 1 L of DMF in a 2 L three-necked flask. Cs₂CO₃ (260 g, 2.03 mol) was then added. The mixture was cooled to 0° C. and CD₃I (280g, 1.93 mol) was added slowly at 0-10° C. The solution was stirred for 6 h at 0-10° C. The solvent was concentrated. DCM (500 mL) was added and the mixture was stirred for 0.5 h at RT. The solution was filtered and the cake washed with DCM (250 mL). An additional amount of DCM (250 mL) was added to the solid and the mixture was stirred for 0.5 h at RT. The mixture was filtered and the cake washed again with DCM (250 mL). The cake was dried to give the title product.

Step B

5-Amino-1-(methyl-d3)-1H-pyrazole-4-carboxamide

To the intermediate from Step A (120 g, 0.96 mol) was added 500 mL of conc. H₂SO₄ at 10° C. The resulting slurry was aged for 6.0 h at RT. CH₃CN (300 mL) was added slowly at 0-10° C. The resulting mixture was filtered and the cake washed with 1 L of CH₃CN. The solids were dissolved in water (600 mL) and 50 wt % NaOH aq. solution was added until the pH of the mixture was ~7. The mixture was concentrated and DMF (200 mL) was added. The mixture was filtered and the cake washed with DMF (100 mL). Another aliquot of DMF (100 mL) was added. The mixture was stirred for 0.5 h at RT, filtered and the cake washed with DMF (200 mL). The organic layers were combined and concentrated to give the title product.

Step C 6-(3,3,4,4,4-Pentafluorobutyl)-1-(methyl-d3)-1H-pyrazolo[3,4-d]pyrimidine-4-carboximidamide The title compound was prepared from the intermediate from Step B according to the procedure described in Steps C through F of Example 1.

Step D

4-Amino-5-(5-fluoropyridin-2-yl)-5-methyl-2-(1-(methyl-d3)-6-(3,3,4,4,4-pentafluorobutyl)-1H-pyrazolo[3,4-d]pyrimidin-4-yl)-5H-pyrrolo[2,3-d]pyrimidin-6(7H)-one The title compound was prepared from the intermediate from Step C and racemic I-2 using an analogous procedure to that described in Step G from Example 1. The racemic material was resolved via a chiral SFC (IC column) to afford Example 2A and 2B. ¹H NMR δ (ppm)(DMSO-d₆): 1.85 (3H, s), 2.89-2.86 (2H, m), 3.39-3.33 (2H, partially overlapping with H₂O), 6.70 (2H, br s), 7.73 (1H, t, J=6.05 Hz), 8.46 (1H, d, J=2.69 Hz), 8.53 (1H, d, J=5.04 Hz), 8.98 (1H, s), 11.52 (1H, br s) m/z=496.14 (M+1).

EXAMPLE 3

4-Amino-2-(6-((3,3-difluorocyclobutyl)methyl)-1-methyl-1H-pyrazolo[3,4-d]pyrimidin-4-yl)-5-(5-fluoropyridin-2-yl)-5-methyl-5,7-dihydro-6H-pyrrolo[2,3-d]pyrimidin-6-one

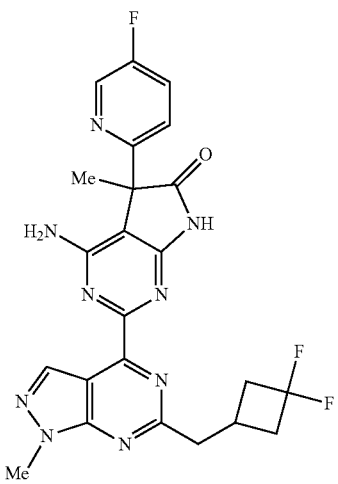 [SMILES: Cn1ncc2c(-c3nc(N)c4c(n3)NC(=O)C4(C)c3ccc(F)cn3)nc(CC3CC(F)(F)C3)nc21]

Step A (3,3-difluorocyclobutyl methyl 4-methylbenzenesulfonate

To a 250 mL round-bottom flask in a water bath at RT were added commercially available (3,3-difluorocyclobutyl) methanol (20 g, 164 mmol), DCM (100 ml), Et₃N (34.2 mL, 246 mmol), DMAP (2 g, 16.38 mmol) and TsCl (37.5 g, 197 mmol) and the reaction was stirred at RT overnight. The mixture was then poured into ice-water (200 mL). The water phase was extracted with EtOAc (200 mL). The organic phases were combined and concentrated. The crude product was re-dissolved in EtOAc (200 mL), washed with water (200 mL), brine (200 mL), dried over MgSO₄, filtered and the solvent was evaporated under reduced pressure. The material was filtered through a one inch silica gel pad, rinsed with EtOAc:Hexanes (1:1, 500 mL), and concentrated to afford the title product.

Step B 2-(3,3-dlfluorocyclobutyl)acetonitrile

To a 100 mL round-bottom flask, the intermediate from Step A (5 g, 18.1 mmol), sodium cyanide (0.976 g, 19.91 mmol) and DMSO (36.2 mL) were added. The reaction was flushed with nitrogen for 2 min, then was heated to 90° C. for 5 h, followed by TLC. The reaction was cooled down to RT, Et₂O (50 mL) and water (50 mL) were added and the resulting mixture was stirred for 10 min. The ether layer was washed with brine (50 mL×2), dried over MgSO₄, filtered and concentrated at RT, pressure at 150 mbar, to afford the title compound.

Step C

Propyl 2-(3,3-difluorocyclobutyl)acetate

To a 40 mL microwave vial, the intermediate from Step B (3.3 g, 70% w/w, 9.61 mmol) and propanol (19.22 ml) were added. HCl gas was bubbled through the reaction mixture for 20 min. The reaction vial was sealed and was heated to 90° C. for 1.5 h. The reaction was cooled down to RT, and the solid was filtered off and rinsed with ether. The solution was concentrated in vacuo to afford the title compound.

Step D 6-((3,3-difluorocyclobutyl)methyl)-1-methyl-1H-pyrazolo[3,4-d]pyrimidine-4-carboximidamide The title compound was prepared from the intermediate from Step C according to the procedure described in Step C to Step F of Example 1.

Step E

4-Amino-2-(6-((3,3-difluorocyclobutyl)methyl)-1-methyl-1H-pyrazolo[3,4-d]pyrimidin-4-yl)-5-(5-fluoropyridin-2-yl)-5-methyl-5H-pyrrolo[2,3-d]pyrimidin-6(7H)-one The title compound was prepared from the intermediate from Step D and I-2B using an analogous procedure to that described in Step G from Example 1. ¹H NMR (500 MHz, CDCl₃): δ 8.88 (1H, s), 8.51 (1H, s), 7.65 (1H, m), 7.60 (1H, m), 4.12 (3H, s), 3.37 (2H, d, J=8.3 Hz), 2.88 (1H, bs), 2.75 (2H, m)), 2.49 (2H, m), 1.94 (3H, s), m/z=496.14 (M+1).

EXAMPLE 4

4-Amino-5-(5-fluoropyridin-2-yl)-5-methyl-2-(1-methyl-6-(4,4,4-trifluorobutyl)-1H-pyrazolo[3,4-d]pyrimidin-4-yl)-5H-pyrrolo[2,3-d]pyrimidin-6(7H)-one

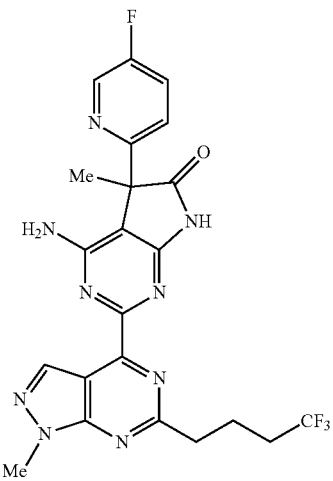 [SMILES: Cn1ncc2c(-c3nc(N)c4c(n3)NC(=O)C4(C)c3ccc(F)cn3)nc(CCCC(F)(F)F)nc21]

Step A propyl 5,5,5-pentafluoropentanoate

The title product was prepared from commercially available 5,5,5-trifluoropentanoic acid using a procedure analogous to that described in Step B of Example 1.

Step B 1-methyl-6-(4,4,4-trifluorobutyl)-1H-pyrazolo[3,4-d]pyrimidine-4-carboximidamide The title compound was prepared from the intermediate from Step A using a procedure analogous to that described in Step C to Step F of Example 1.

Step C

4-Amino-5-(5-fluoropyridin-2-yl)-5-methyl-2-(1-methyl-6-(4,4,4-trifluorobutyl)-1H-pyrazolo[3,4-d]pyrimidin-4-yl)-5H-pyrrolo[2,3-d]pyrimidin-6(7H)-one The title compound was prepared from the intermediate from Step B and I-2B using a procedure analogous to that described in Step G from Example 1. $^1$H NMR (300 MHz, CDCl$_3$) δ 8.67 (s, 1H), 8.48 (d, J=2.7 Hz, 1H), 7.61-7.55 (m, 1H), 7.48-7.43 (m, 1H), 4.16 (s, 3H), 3.40-3.30 (m, 2H), 2.29-2.26 (m, 4H), 1.93 (s, 3H).

EXAMPLE 5

4-Amino-2-(6-(2,3-difluorobenzyl)-1-methyl-1H-pyrazolo[3,4-d]pyrimidin-4-yl)-5-methyl-5-(3-methyl-1,2,4-oxadiazol-5-yl)-5,7-dihydro-6H-pyrrolo[2,3-d]pyrimidin-6-one

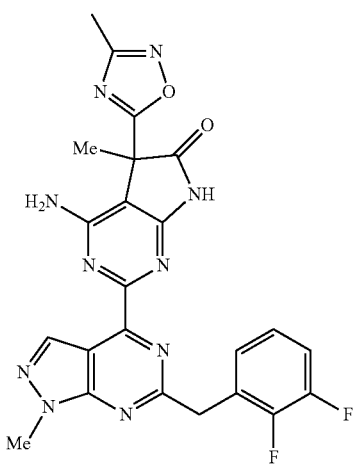 [SMILES: Cc1noc(C2(C)C(=O)Nc3nc(-c4nc(Cc5cccc(F)c5F)nc5c4cnn5C)nc(N)c32)n1]

Step A 6-(2,3-Difluorobenzyl)-1-methyl-1H-pyrazolo[3,4-d]pyrimidine-4-carboximidamide The title product was prepared from commercially available methyl 2-(2,3-difluorophenyl)acetate and the intermediate from Step B in Example 1 using a procedure analogous to that described in Steps C to Step F from Example 1.

Step B

4-Amino-2-(6-(2,3-difluorobenzyl)-1-methyl-1H-pyrazolo[3,4-d]pyrimidin-4-yl)-5-methyl-5-(3-methyl-1,2,4-oxadiazol-5-yl)-5,7-dihydro-6H-pyrrolo[2,3-d]pyrimidin-6-one The title compound was prepared with the intermediate from Step A and I-3 using a procedure analogous to that described in Step G from Example 1. $^1$H NMR δ (ppm) (DMSO-d$_6$): 8.98 (1H, s), 7.31-7.35 (1H, m), 7.17 (3H, s), 4.51 (2H, s), 4.00 (3H, s), 2.34 (3H, s), 1.91 (3H, s).

EXAMPLE 6

4-Amino-5-(5-fluoropyridin-2-yl)-5-methyl-2-(1-methyl-6-(4,4,4-trifluorobutan-2-yl)-1H-pyrazolo[3,4-d]pyrimidin-4-yl)-5,7-dihydro-6H-pyrrolo[2,3-d]pyrimidin-6-one

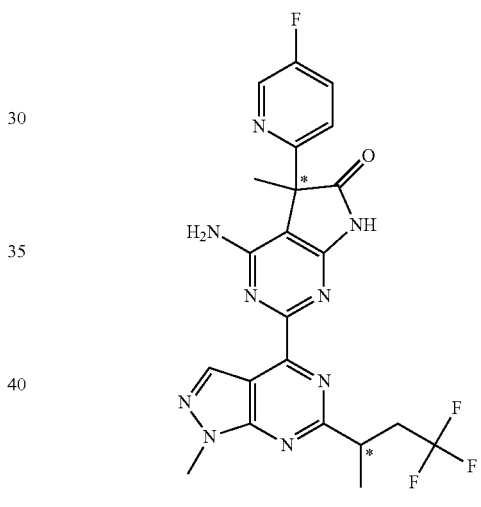

Into a 25-mL round-bottom vial, were placed 1-30, Table 3 (120 mg, 0.42 mmol, 1.0 equiv), I-2B (120 mg, 0.46 mmol, 1.1 equiv), tert-butanol (4 ml) and potassium bicarbonate (84 mg, 0.84 mmol, 2.0 equiv). The resulting mixture was stirred for 16 h at 80° C. The reaction was then quenched by the addition of brine (10 mL). The resulting solution was extracted with EtOAc (3×20 mL) and the organic layers were combined, dried over anhydrous sodium sulfate, filtered and the filtrate was concentrated in vacuo to dryness. The residue was applied onto a silica gel column with DCM/MeOH (10/1) to afford the title compound as a diastereomeric mixture. The diastereomers were resolved by Chiral-Prep-HPLC (Chiral-P(Lux-), SFC with 30% MeOH containing 0.2% diethylamine) to afford both diastereomers of the title compound.

Using essentially the same procedures described in Examples 1 to 6 and using the appropriate intermediates, the following compounds in Table 4 were made.

TABLE 4
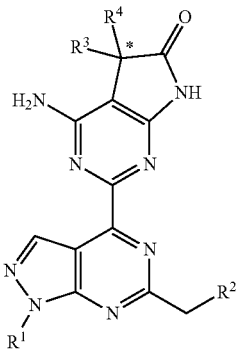
| EX. | Chirality Source or chiral resolution column | R¹ | R² | R³ | R⁴ | m/z (M + H) |
|---|---|---|---|---|---|---|
| 7 | I-1A | CD₃ | CH₂CF₂CF₃ | Me | 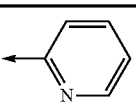 | 523 |
| 8 | Chiralpak AD column | CD₃ | CH₂CF₂CF₃ | Me | 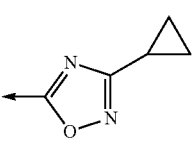 | 554 |
| 9 | I-12B | CD₃ | CH₂CF₂CF₃ | Me | 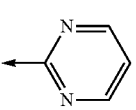 | 524 |
| 10 | IC column | CD₃ | CH₂CF₂CF₃ | Me | 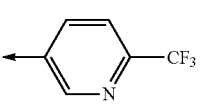 | 591 |
| 11 | | CD₃ | CH₂CF₂CF₃ | Me | 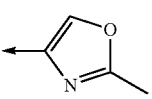 | 527 |
| 12 | IC column | CD₃ | CH₂CF₂CF₃ | Me | 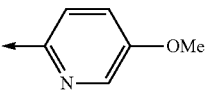 | 553 |
| 13 | I-11B | CD₃ | CH₂CF₂CF₃ | Me | 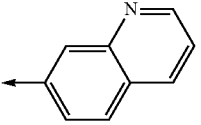 | 573 |
| 14 | I-23B | CD₃ | CH₂CF₂CF₃ | Me | 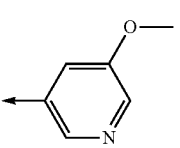 | 553 |
| 15 | OD column | CH₃ | CH₂CF₂CF₃ | cPr | 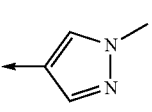 | 549 |
| 16 | IC column | CH₃ | CH₂CF₂CF₃ | cPr | 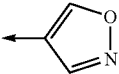 | 536 |

TABLE 4-continued

| | | | | | | |
|---|---|---|---|---|---|---|
| 17 | OJ column | CH₃ | CH₂CF₂CF₃ | Et | 5-pyridyl with 2-OMe | 564 |
| 18 | OD column | CD₃ | CH₂CF₂CF₃ | Me | pyridyl with methyl ester | See Table Below |
| 19 | OD column | CD₃ | CH₂CF₂CF₃ | Me | methyl-1,2,4-oxadiazole | See Table Below |
| 20 | OD column | CH₃ | CH₂CF₂CF₃ | Me | methyl-1,2,4-oxadiazole | See Table Below |
| 21 | IC column | CH₃ | CH₂CH₂CF₃ | Me | pyridyl | 484.0 |
| 22 | IC column | CH₃ | CH₂CF₂CF₃ | Me | pyridyl | 520.0 |
| 23 | I-28B or AD-H | CH₃ | CH₂CF₂CF₃ | Me | N-methylpyrazolyl | 523.0 |
| 24 | IC column | CD₃ | CH₂CF₂CF₃ | cPr | N-methylpyrazolyl | 552.4 |
| 25 | OJ column | CD₃ | CH₂CF₂CF₃ | cPr | N-methyltetrazolyl | See Table Below |
| 26 | IC column | CH₃ | CH₂CF₂CF₃ | cPr | N-isopropylpyrazolyl | 577.2 |
| 27 | I-8A | CH₃ | CH₂CF₂CF₃ | Me | methyl-1,3,4-thiadiazolyl | 505.0 |
| 28 | IC column | CH₃ | CH₂CF₂CF₃ | cPr | oxazolyl | 535.8 |

TABLE 4-continued

| EX. | | R | R' | R'' | Ar | MS |
|---|---|---|---|---|---|---|
| 29 | I-2B | CH₃ | CH₂-(3,3-difluorocyclobutyl) | Me | 2-pyridyl-5-F | 510.1 |
| 30 | I-2B | CH₃ | CH₂-cyclobutyl | Me | 2-pyridyl-5-F | 474.0 |
| 31 | I-31A | CH₃ | 3,3-difluorocyclobutyl | cPr | 2-pyridyl-5-Cl | 538.1 |
| 32 | I-32A | CH₃ | 3,3-difluorocyclobutyl | cPr | 2-pyridyl-5-CF₃ | 572.1 |
| 33 | IC column-ent B | CH₃ | 3,3-difluorocyclobutyl | Me | 2-pyridyl-5-OMe | 508.1 |
| 34 | I-2B | CH₃ | CH₂CH₂CH₃ | Me | 2-pyridyl-5-F | 448.1 |
| 35 | I-33A | CH₃ | CH₂CH₂CH₃ | Me | 2-pyridyl-5-iPr | 472.1 |
| 36 | ChiralPak AD-H ent A | CH₃ | CH₂CH₂CH₃ | Me | 2-pyridyl-5-OMe | 460.2 |
| 37 | I-13A | CH₃ | 3,3-difluorocyclobutyl | Me | 2-pyridyl-5-Cl | 512.4 |

| EX. | Data |
|---|---|
| 18 | ¹H NMR δ (ppm)(500 MHz, DMSO-d₆): 11.35 (1 H, s), 8.97 (1 H, s), 7.38-6.94 (5 H, m), 4.51 (2 H, s), 3.99 (3 H, s), 2.33 (3 H, s), 1.91 (3 H, s). |
| 19 | ¹H NMR δ (ppm)(500 MHz, DMSO-d₆): 8.97 (1 H, s), 3.30-3.40 (2 H, overlapping with water), 2.81-2.90 (2 H, m), 2.56 (3 H, s), 1.82 (3 H, s). |
| 20 | ¹H NMR δ (ppm)(DMSO-d₆): 8.97 (1 H, s), 4.06 (3 H, s), 3.30-3.40 (2 H, overlapping with water), 2.83-2.91 (2 H, m), 2.56 (3 H, s), 1.82 (3 H, s). |
| 25 | ¹H NMR δ (ppm)(DMSO-d₆): 11.72 (1 H, s), 9.01 (1 H, s), 7.00 (2 H, br s), 4.18 (3 H, s), 3.33-3.36 (2 H, m partially overlapping with H₂O), 2.86-2.89 (2 H, m), 2.14-2.17 (1 H, m), 0.85-0.88 (2 H, m), 0.61-0.68 (1 H, m), 0.24-0.26 (1 H, m). |

EXAMPLE 38

4-Amino-5-cyclopropyl-5-(5-cyclopropyl-1,3,4-oxadiazol-2-yl)-2-(1-(methyl-d3)-6-(3,3,4,4,4-pentafluorobutyl)-1H-pyrazolo[3,4-d]pyrimidin-4-yl)-5,7-dihydro-6H-pyrrolo[2,3-d]pyrimidin-6-one and the S and R isomers thereof

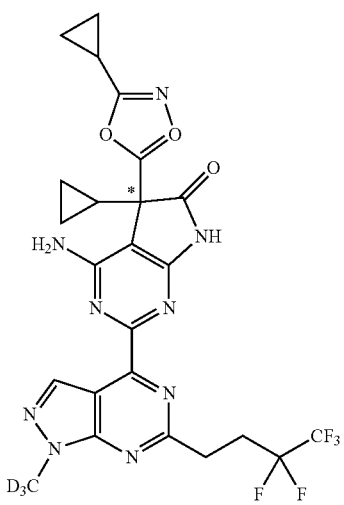

Step A

Ethyl 4-amino-5-cyclopropyl-2-(6-(3,3,4,4,4-pentafluorobutyl)-1-(methyl-d3)-1H-pyrazolo[3,4-d]pyrimidin-4-yl)-6-oxo-6,7-dihydro-5H-pyrrolo[2,3-d]pyrimidine-5-carboxylate The title compound was prepared from 6-(3,3,4,4,4-pentafluorobutyl)-1-(methyl-d3)-1H-pyrazolo[3,4-d]pyrimidine-4-carboximidamide the intermediate from Step C of Example 2, and I-17 analogous to the procedure described in Step G of Example 1.

Step B

4-Amino-5-cyclopropyl-2-(6-(3,3,4,4,4-pentafluorobutyl)-1-(methyl-d3)-1H-pyrazolo[3,4-d]pyrimidin-4-yl)-6-oxo-6,7-dihydro-5H-pyrrolo[2,3-d]pyrimidine-5-carbohydrazide Hydrazine hydrate (0.40 mL, 8.29 mmol) was added to a MeOH (8 mL) solution of the intermediate from Step A (0.315 g, 0.58 mmol). The mixture was heated at 50° C. for 2 h, cooled to RT, and concentrated in vacuo. The crude product was purified by silica gel chromatography using a MeOH/DCM gradient to give the title compound.

Step C

4-Amino-N'-(cyclopropanecarbonyl)-5-cyclopropyl-2-(1-methyl-6-(3,3,4,4,4-pentafluorobutyl)-1-(methyl-d3)-1H-pyrazolo[3,4-d]pyrimidin-4-yl)-6-oxo-6,7-dihydro-5H-pyrrolo[2,3-d]pyrimidine-5-carbohydrazide To a mixture of the intermediate from Step B (0.303 g, 0.573 mmol), cyclopropanecarboxylic acid (0.108 g, 1.26 mmol), and PyBOP (0.745 g, 1.43 mmol) in DMF (5 mL) was added DIEA (0.370 g, 2.86 mmol). The solution was stirred at RT for 18 h and water (10 mL) was added. The material was extracted with EtOAc. The organic layer was dried, filtered, and concentrated in vacuo. The crude product was purified by silica gel chromatography using MeOH/DCM gradient to give title compound.

Step D

4-Amino-5-cyclopropyl-5-(5-cyclopropyl-1,3,4-oxadiazol-2-yl)-2-(1-(methyl-d3)-6-(3,3,4,4,4-pentafluorobutyl)-1H-pyrazolo[3,4-d]pyrimidin-4-yl)-5,7-dihydro-6H-pyrrolo[2,3-d]pyrimidin-6-one To the intermediate from Step C (0.35 g, 0.586 mmol) was added polyphosphoric acid (2 mL). The resulting mixture was heated at 125° C. for 18 h and cooled to RT. Water (5 mL) was added and followed by solid $K_2CO_3$ until pH=7. The material was extracted with EtOAc. The organic layer was dried, filtered, and concentrated in vacuo. The crude product was purified by reversed-phase HPLC using water/acetonitrile (0.1% TFA) to give the title compound. Resolution via chiral SFC (AD column) provided Isomer 38A (faster eluting) and Isomer 38B (slower eluting) of the title compound. $^1$H NMR (500 MHz, DMSO-$d_6$): δ 11.62 (1H, s), 9.00 (1H, s), 7.14 (2H, s), 3.37-3.25 (2H, overlapping with $H_2O$), 2.94-2.81 (3H, m), 2.28-2.22 (1H, m), 2.00-1.94 (1H, m), 1.18-1.14 (2H, m), 1.03-0.98 (2H, m), 0.68-0.53 (3H, m), 0.40-0.34 (1H, m). m/z=581 (M+H).

Using essentially the same procedures described for Example 38, the following compounds in Table 5 were synthesized.

TABLE 5

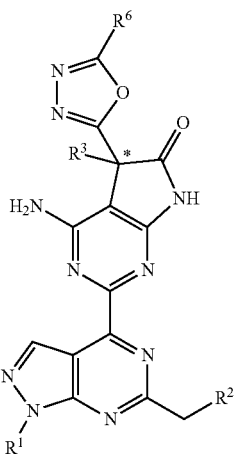

| EX. | Chirality Source or chiral resolution column | R¹ | R² | R³ | R⁶ | m/z (M + H) |
|---|---|---|---|---|---|---|
| 39 | IC column | CD₃ | CH₂CF₂CF₃ | Me | cyclopropyl | 554.1 |
| 40A | AD column | CD₃ | CH₂CF₂CF₃ | cyclopropyl | Me | 554.0 |
| 40B | AD column | CD₃ | CH₂CF₂CF₃ | cyclopropyl | Me | 554.0 |
| 42 | OD column | CD₃ | CH₂CF₂CF₃ | Et | cyclopropyl | 567.9 |
| 43 | IC column | CD₃ | CH₂CH₂CF₃ | cyclopropyl | cyclopropyl | 544.1 |
| 44 | IA column | CH₃ | CH₂CF₂CF₃ | cyclopropyl | cyclopropyl | 577 |
| 45 | OD column | Et | CH₂CF₂CF₃ | cyclopropyl | cyclopropyl | See table below |
| 46 |  | CD₃ | CH₂CF₂CF₃ | cyclopropyl | cyclobutyl | 594.0 |
| 47 | IC column | CD₃ | CH₂CF₃ | cyclopropyl | cyclopropyl | See Table below |
| 48 | IB-3 column | CH₃ | CH₂CF₂CF₃ | cyclopropyl | 1-methylcyclopropyl | 591.4 |
| 49 | IB-3 column | CH₃ | CH₂CF₂CF₃ | cyclopropyl | iPr | 579.1 |
| 50 | IB-3 column | CH₃ | CH₂CF₂CF₃ | Me | iPr | 553.0 |
| 51 | IB-3 column | CH₃ | 3,3-difluorocyclobutyl | cyclopropyl | cyclopropyl | 535.5 |

TABLE 5-continued

| 52 | IB-3 column | CH₃ | [cyclobutyl-CF₂ linker to cyclopropyl] | Et | 565.3 |
| 53 | IB-3 column | CH₃ | CH₂CF₂CF₃ | Et | [cyclopropyl] | 565.2 |

| EX. | ¹H NMR DATA |
|---|---|
| 45 | ¹H NMR δ (ppm)(DMSO-d₆): 8.98 (1 H, s), 4.49 (2 H, q, J = 7.18 Hz), 3.33 (2H, overlapped by H₂O), 2.85-2.89 (2 H, m), 2.23-2.24 (1 H, m), 1.94-1.97 (1 H, m), 1.45 (3 H, t, J = 7.16 Hz), 1.13-1.15 (2 H, m), 0.99-1.01 (2 H, m), 0.58-0.64 (3 H, m), 0.35-0.37 (1 H, m). |
| 47 | ¹H NMR δ (ppm)(DMSO-d₆): 8.99 (1 H, s), 3.33 (2 H, m, partially overlapped by H₂O), 2.90-2.92 (2 H, m), 2.23-2.24 (1 H, m), 1.95-1.96 (1 H, m), 1.13-1.14 (2 H, m), 0.99-1.00 (2 H, m), 0.59-0.61 (3 H, m), 0.35-0.36 (1 H, m). |

EXAMPLE 54

4-Amino-5-cyclopropyl-5-(1-methyl-1H-1,2,3-triazol-4-yl)-2-(1-(methyl-d3)-6-(3,3,4,4,4-pentafluorobutyl)-1H-pyrazolo[3,4-d]pyrimidin-4-yl)-5,7-dihydro-6H-pyrrolo[2,3-d]pyrimidin-6-one

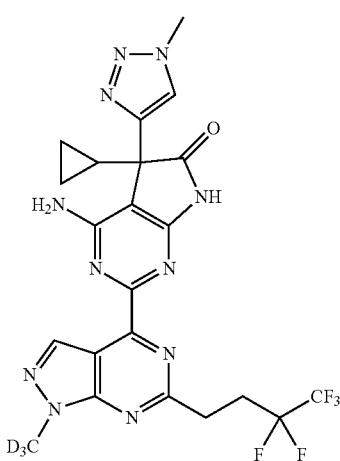 [SMILES: [2H]C([2H])([2H])n1ncc2c(-c3nc(N)c4c(n3)NC(=O)C4(c3cn(C)nn3)C3CC3)nc(CCC(F)(F)C(F)(F)F)nc21]

Step A

4-Amino-5-cyclopropyl-5-ethynyl-2-(6-(3,3,4,4,4-pentafluorobutyl)-1-methyl-d3-1H-pyrazolo[3,4-d]pyrimidin-4-yl)-5H-pyrrolo[2,3-d]pyrimidin-6(7)-one A solution of I-19 (375 mg, 1.73 mmol) in t-BuOH (5 mL) was added to the intermediate from Step C of Example 2 (470 mg, 1.45 mmol). The resulting solution was heated at 85° C. for 7 h. The reaction was then cooled to RT, water (7 mL) was added, and the material reheated to 85° C. for 20 min then allowed to return to RT over several hours without stirring and allowed to stand at ambient temperature for 16 h. The resulting precipitate was collected to afford the title compound. Chiral separation using SFC on a Chiralcel OD column provided both Isomer A and Isomer B of the title compound.

Step B

4-Amino-5-cyclopropyl-5-(1-methyl-1H-1,2,3-triazol-4-yl)-2-(1-(methyl-d3)-6-(3,3,4,4,4-pentafluorobutyl)-1H-pyrazolo[3,4-d]pyrimidin-4-yl)-5,7-dihydro-6H-pyrrolo[2,3-d]pyrimidin-6-one Iodomethane (50 μL, 0.80 mmol) was added to a stirred suspension of sodium azide (48 mg, 0.74 mmol) in DMF (2 mL) in a vial wrapped with foil. The suspension was stirred for 16 h then water (1 mL), copper sulfate (10 mg, 0.06 mmol), sodium ascorbate (96 mg, 0.48 mmol), and Isomer A from Step A (80 mg, 0.161 mmol) were added. The reaction mixture was heated at 40° C. for 72 h. The solution was diluted with EtOAc and washed with water. The organic layer was dried with MgSO₄, filtered, and concentrated in vacuo. The crude product was purified by reverse phase HPLC (ceric ammonium nitrate, water, 0.1% TFA modifier) to give the title compound. ¹H NMR (500 MHz, DMSO-d₆) δ: 11.43 (1H, s), 9.00 (1H, s), 8.15 (1H, s) 7.03 (2H, s), 4.06 (3H, s), 3.47-3.29 (2H, m, partially overlapping with H₂O), 2.94-2.80 (2H, m), 1.79-1.70 (1H, m), 0.58-0.46 (3H, m), 0.43-0.31 (1H, m). m/z=553 (M+1).

EXAMPLE 55

4-Amino-5-cyclopropyl-5-(1-methyl-1H-1,2,3-triazol-4-yl)-2-(1-methyl-6-(3,3,4,4,4-pentafluorobutyl)-1H-pyrazolo[3,4-d]pyrimidin-4-yl)-5,7-dihydro-6H-pyrrolo[2,3-d]pyrimidin-6-one

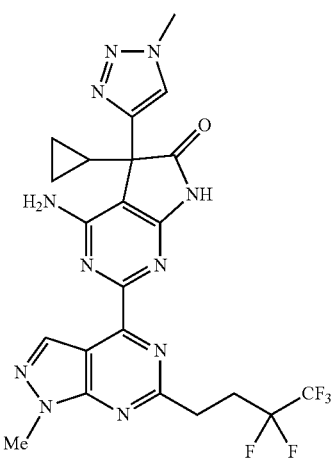 [SMILES: Cn1cc(C2(C3CC3)C(=O)Nc3nc(-c4nc(CCC(F)(F)C(F)(F)F)nc5c4cnn5C)nc(N)c32)nn1]

Step A

4-Amino-5-cyclopropyl-5-ethynyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one The title compound was prepared with I-19 and the intermediate from Step F of Example 1. The racemic material was resolved by chiral resolution using Chiralpak IC column to afford Isomer A (faster eluting) and Isomer B (slower eluting) of the title compound.

Step B 4-Amino-5-cyclopropyl-5-(1-methyl-1H-1,2,3-triazol-4-yl)-2-(1-methyl-6-(3,3,4,4,4-pentafluorobutyl)-1H-pyrazolo[3,4-d]pyrimidin-4-yl)-5,7-dihydro-6H-pyrrolo[2,3-d]pyrimidin-6-one Into a 10-mL vial, were placed DMF (8 mL), and MeI (66 mg, 0.47 mmol, 2.3 equiv). This was followed by the addition of sodium azide (53 mg, 0.81 mmol, 4.0 equiv) at ambient temperature. The resulting solution was stirred for 16 h at ambient temperature. To this was added Isomer A from Step A (100 mg, 0.20 mmol, 1.0 equiv), 5-(1,2-dihydroxyethyl)-4-hydroxy-3-(sodiooxy)-2,5-dihydrofuran-2-one (40 mg, 0.20 mmol, 1.0 equiv), water (1 mL), and copper sulfate (13 mg, 0.4 equiv) and the resulting mixture was stirred for 3 days at 50° C. The resulting solution was diluted with water (100 mL) and extracted with EtOAc (3×100 mL) and the organic layers were combined, dried over anhydrous sodium sulfate, and filtered. The filtrate was concentrated in vacuo to dryness. The residue was applied onto a silica gel column with DCM/MeOH (100/1). Then the crude product was purified by reverse phase HPLC (MeCN, water, 0.05% TFA modifier) to afford the title product: 1H NMR (400 MHz, CDCl$_3$) δ: 9.29-9.25 (br, 1H), 8.77 (s, 1H), 7.76 (d, J=4.0 Hz, 1H), 4.18 (s, 3H), 4.12 (s, 3H), 3.58-3.53 (m, 2H), 2.90-2.76 (m, 2H), 1.64-1.57 (m, 1H), 0.66-0.56 (m, 4H); MS (ES, m/z) 550 [M+1]+.

EXAMPLE 56

4-Amino-5-(1-isopropyl-1H-1,2,3-triazol-4-yl)-5-methyl-2-(1-methyl-6-(3,3,4,4,4-pentafluorobutyl)-1H-pyrazolo[3,4-d]pyrimidin-4-yl)-5,7-dihydro-6H-pyrrolo[2,3-d]pyrimidin-6-one

Step A

4-Amino-5-ethynyl-5-methyl-6-(3,3,4,4,4-pentafluorobutyl)-1H-pyrazolo[3,4-d]pyrimidin-4-yl)-5H-pyrrolo[2,3-d]pyrimidin-6(7H)-one and the R and S enantiomers thereof The title compound was prepared from I-18 and the intermediate from Step F of Example 1. The racemic material was resolved by chiral SFC (IC-H column) to obtain Isomer A (faster eluting) and Isomer B (slower eluting) of the title compound.

Step B

4-Amino-5-(1-Isopropyl-1H-1,2,3-triazol-4-yl)-5-methyl-2-(1-methyl-6-(3,3,4,4,4-pentafluorobutyl)-1H-pyrazolo[3,4-d]pyrimidin-4-yl)-5,7-dihydro-6H-pyrrolo[2,3-d]pyrimidin-6-one To a 40 mL microwave vial, Isomer A from Step A (590 mg, 1.26 mmol) and bromotris(triphenylphosphine)copper (I) (235 mg, 0.25 mmol) were added. The vial was capped and flushed with nitrogen for 2 min. DMSO (12.7 mL) and 2-azidopropane (340 mg, 3.8 mmol) were added via syringe, and the reaction was heated to 55° C. overnight. The reaction was cooled to RT, diluted with EtOAc (50 mL), washed with water (250 mL) and brine (50 mL). The organic phase was stirred with NH$_4$OH (10 mL×2, 1 h each), washed with water (50 mL×2), dried by MgSO$_4$, filtered and concentrated under reduced pressure. Silica gel chromatography using a hexanes/EtOAc gradient (0-100%) afforded the title product. $^1$H NMR (500 MHz, CDOD$_3$): δ 8.94 (1H, s), 8.01 (1H, s), 4.89 (1H, m), 4.15 (3H, s), 3.48 (2H, m), 2.92 (2H, m), 1.90 (3H, s), 1.60 (6H, dd, J=6.7, 3.4 Hz); m/z=552.26 (M+1).

EXAMPLE 57

4-Amino-5-(1-isopropyl-1H-1,2,3-triazol-4-yl)-5-methyl-2-(1-(methyl-d3)-6-(3,3,4,4,4-pentafluorobutyl)-1H-pyrazolo[3,4-d]pyrimidin-4-yl)-5,7-dihydro-6H-pyrrolo[2,3-d]pyrimidin-6-one

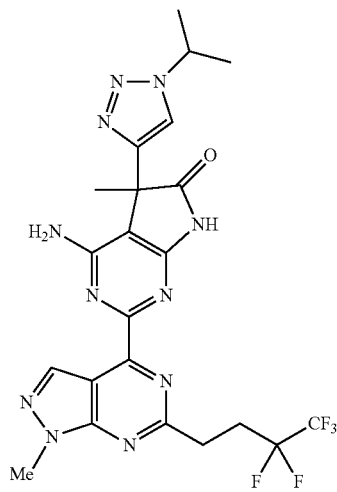 [SMILES: CC(C)n1cc(C2(C)C(=O)Nc3nc(-c4nc(CCC(F)(F)C(F)(F)F)nc5c4cnn5C)nc(N)c32)nn1]

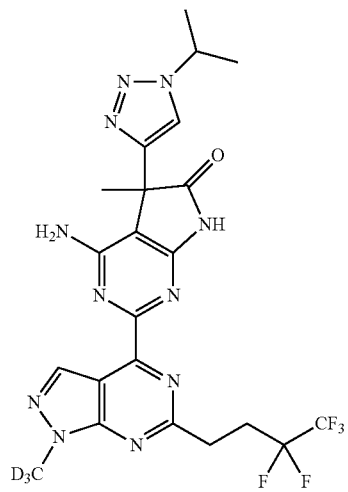 [SMILES: [2H]C([2H])([2H])n1ncc2c(-c3nc(N)c4c(n3)NC(=O)C4(C)c3cn(C(C)C)nn3)nc(CCC(F)(F)C(F)(F)F)nc21]

Step A

4-Amino-5-ethynyl-5-methyl-2-(6-(3,3,4,4,4-pentafluorobutyl)-1-(methyl-d3)-1H-pyrazolo[3,4-d]pyrimidin-4-yl)-5H-pyrrolo[2,3-d]pyrimidin-6(7H)-one and the R and S enantiomers thereof The title compound was prepared from I-18 and the intermediate from Step B of Example 2. The racemic material was resolved by chiral resolution using a chiral SFC (IC-H column) to afford Isomer A (faster eluting) and Isomer B (slower eluting).

Step B

4-Amino-5-(1-Isopropyl-1H-1,2,3-triazol-4-yl)-5-methyl-2-(1-(methyl-d3)-6-(3,3,4,4,4-pentafluorobutyl)-1H-pyrazolo[3,4-d]pyrimidin-4-yl)-5,7-dihydro-6H-pyrrolo[2,3-d]pyrimidin-6-one To sodium azide (111 mg, 1.7 mmol) in a microwave vial, DMSO (2 mL) was added, and the vial was capped. Next, MeI (107 µl, 1.7 mmol) was added via syringe and the mixture was heated to 40° C. for 16 h. Isomer A from Step A (80 mg, 0.17 mmol) and bromotris(triphenylphosphine)copper(I) (63.4 mg, 0.068 mmol) were added in a microwave vial (4 mL), capped and flushed with $N_2$ for 2 min, DMSO (1704 µl) was added and after everything was dissolved, the methylazide solution was added and the reaction heated at 50° C. for 16 h. The mixture was cooled, diluted with EtOAc (20 mL) and washed with water (20 mL), brine (20 mL) and $NH_4OH$ (8 mL). The mixture was stirred for 2 h, and the organic layer separated off and treated again with $NH_4OH$ (4 mL) for 1 h. The organic was separated off and was extracted with brine (20 mL×2), then dried by $MgSO_4$, filtered and the solvent was evaporated under reduced pressure. Purification by silica gel chromatography (0-100% EtOAc gradient in hexanes) afforded the title compound. m/z=557.1 (M+1)

EXAMPLE 58

4-Amino-5-ethyl-5-(1-methyl-1H-1,2,3-triazol-4-yl)-2-(1-methyl-6-(3,3,4,4,4-pentafluorobutyl)-1H-pyrazolo[3,4-d]pyrimidin-4-yl)-5,7-dihydro-6H-pyrrolo[2,3-d]pyrimidin-6-one

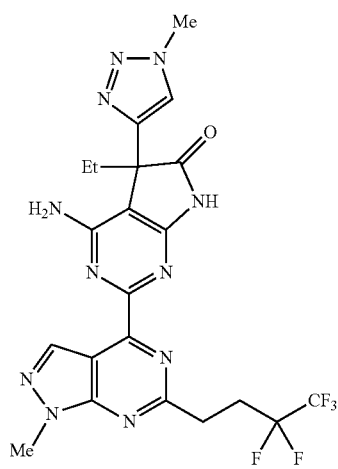 [SMILES: CCC1(c2cn(C)nn2)C(=O)Nc2nc(-c3nc(CCC(F)(F)C(F)(F)F)nc4c3cnn4C)nc(N)c21]

Step A

4-Amino-5-ethyl-5-ethynyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one The title compound was prepared from I-19 and the intermediate from Step F of Example 1. The racemic material was resolved by chiral resolution using SFC conditions (30% IPA (0.2% diethylamine), $CO_2$, IC-H column) to obtain Isomer A (faster eluting) and Isomer B (slower eluting) of the title compound.

Step B

4-Amino-5-ethyl-5-(1-methyl-1H-1,2,3-triazol-4-yl)-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one To sodium azide (108 mg, 1.665 mmol) in a microwave vial, DMSO (2 mL) was added, the vial was capped and then MeI (104 µl, 1.67 mmol) added via syringe and heated to 40° C. for 16 h. Isomer A from Step A ((80 mg, 0.167 mmol) and bromo-tris(triphenylphosphine)copper(I) (62 mg, 0.07 mmol) were added in another microwave vial (4 mL), the vial was capped and flushed with $N_2$ for 2 min, DMSO (1685 µl) was added and after everything was dissolved, the methylazide solution was added and the reaction mixture was heated at 50° C. for 16 h. The mixture was cooled, diluted with EtOAc (20 mL) and washed with water (20 mL), brine (20 mL) and $NH_4OH$ (8 mL). The mixture was stirred for 2 h, and the organic layer separated off and treated again with $NH_4OH$ (4 mL) for 1 h. The organic layer was separated off and was extracted with brine (20 mL×2), then dried with $MgSO_4$, filtered and the solvent was evaporated in vacuo. The resulting material was purified by silica gel chromatography (0-100% EtOAc gradient in hexanes). The material was further purified via reverse phase (ceric ammonium nitrate, water, 0.1% TFA) to afford the title compound. m/z=538.1 (M+1)

EXAMPLE 59

4-Amino-5-(1-cyclopropyl-1H-1,2,3-triazol-4-yl)-5-methyl-2-(1-methyl-6-(3,3,4,4,4-pentafluorobutyl)-1H-pyrazolo[3,4-d]pyrimidin-4-yl)-5,7-dihydro-6H-pyrrolo[2,3-d]pyrimidin-6-one

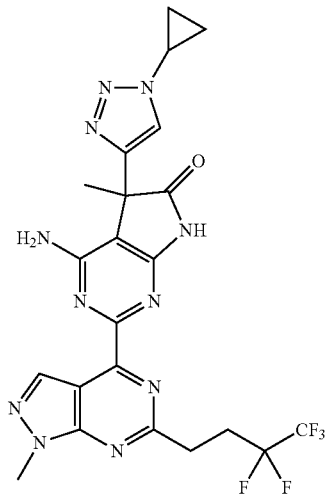 [SMILES: Cn1ncc2c(-c3nc(N)c4c(n3)NC(=O)C4(C)c3cn(C4CC4)nn3)nc(CCC(F)(F)C(F)(F)F)nc21]

Step A

4-Amino-5-ethynyl-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one The title compound was prepared from I-17A and the intermediate from Step F of Example 1 analogous to Step G of Example 1.

Step B

4-Amino-5-(1-cyclopropyl-1H-1,2,3-triazol-4-yl)-5-methyl-2-(1-methyl-6-(3,3,4,4,4-pentafluorobutyl)-1H-pyrazolo[3,4-d]pyrimidin-4-yl)-5,7-dihydro-6H-pyrrolo[2,3-d]pyrimidin-6-one Into an 8-mL vial, were placed potassium carbonate (379 mg, 2.8 mmol), cyclopropanamine (98 mg, 1.7 mmol), copper sulfate (66 mg, 0.41 mmol) and MeOH (11.2 mL). To this was added 1H-imidazole-1-sulfonyl azide hydrochloride (431 mg, 2.1 mmol) in water (5.6 mL). The resulting mixture was stirred for 5 h at RT. This was followed by the addition of sodium (R)-2-((S)-1,2-dihydroxyethyl)-4-hydroxy-5-oxo-2,5-dihydrofuran-3-olate (109 mg, 0.55 mmol) and the intermediate from the previous step (160 mg, 0.34 mmol). The resulting mixture was stirred for 16 h at 70° C. The reaction mixture was quenched by the addition of ammonia (50 mL). The resulting solution was extracted with EtOAc (3×50 mL) and the organic layers combined. The resulting solution was washed with ammonia (3×50 mL) and brine (50 mL). The mixture was dried over anhydrous sodium sulfate, and filtered. The filtrate was concentrated in vacuo to dryness. The crude product was purified by Prep-HPLC (water with 0.05% ammonia and MeCN (35% MeCN up to 50% in 8 min) to afford the title compound: $^1$H NMR (CD$_3$OD, 400 MHz): δ 8.93 (s, 1H), 8.02 (s, 1H), 4.15 (s, 3H), 3.97-3.91 (m, 1H), 3.50-3.46 (m, 2H), 2.98-2.84 (m, 2H), 1.88 (s, 3H), 1.31-1.15 (m, 4H); MS (ES, m/z) 550 [M+1]$^+$.

EXAMPLE 60

4-Amino-S-methyl-2-(1-methyl-6-(3,3,4,4,4-pentafluorobutyl)-1H-pyrazolo[3,4-d]pyrimidin-4-yl)-5-(1H-1,2,3-triazol-4-yl)-5,7-dihydro-6H-pyrrolo[2,3-d]pyrimidin-6-one

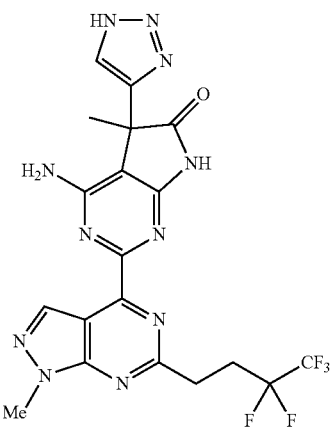 [SMILES: Cn1ncc2c(-c3nc(N)c4c(n3)NC(=O)C4(C)c3c[nH]nn3)nc(CCC(F)(F)C(F)(F)F)nc21]

To a 4 mL microwave vial, Isomer A from Step A of Example 56 (100 mg, 0.214 mmol) and bromotris(triphenylphosphine)copper(I) (39.9 mg, 0.04 mmol) were added. The vial was capped and flushed with nitrogen for 2 min. DMSO (2144 μl) and azidotrimethylsilane (148 μl, 1.07 mmol) were added. The reaction was set up in a microwave at 120° C. for 2 h. Upon cooling down to RT, the reaction was purified by reverse phase HPLC (MeCN, water, 0.1% TFA). The product TFA salt fractions were lyophilized overnight. The dry product TFA salt was dissolved in EtOAc (50 mL), stirred with NH$_4$OH (6 mL 2×, 1 h each). The NH$_4$OH phase was extracted with EtOAc (20 mL 2×). The organic phase was combined and washed with brine (20 mL 2×) and acidified to a pH ~5 with acetic acid, dried over MgSO$_4$, filtered and concentrated in vacuo to afford the title compound. $^1$H NMR (500 MHz, CDOD$_3$): δ 8.93 (1H, s), 7.85 (1H, s), 4.15 (3H, s), 3.48 (2H, m), 2.91 (2H, m), 1.91 (3H, s), m/z=510.07 (M+1).

EXAMPLE 61

4-Amino-5-(2-isopropyl-2H-1,2,3-triazol-4-yl)-5-methyl-2-(1-methyl-6-(3,3,4,4,4-pentafluorobutyl)-1H-pyrazolo[3,4-d]pyrimidin-4-yl)-5,7-dihydro-6H-pyrrolo[2,3-d]pyrimidin-6-one

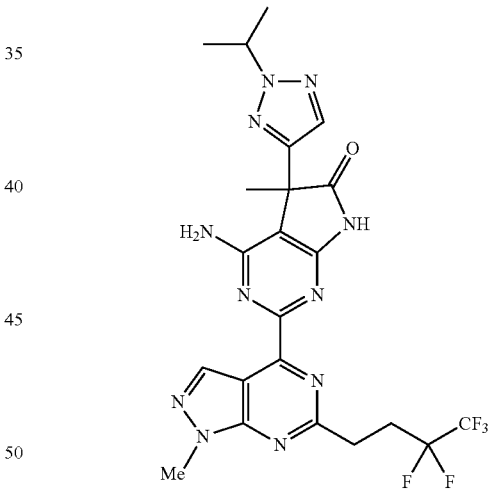

The product of Example 60 (100 mg, 0.137 mmol, 70%), K$_2$CO$_3$ (57.0 mg, 0.412 mmol), DMF (687 μl) and 2-bromopropane (15.64 μl, 0.165 mmol) were added to a 4 mL vial. The reaction was run at RT for 48 h. The reaction was diluted with EtOAc (20 mL), washed with water (10 mL), brine (10 mL), dried with MgSO$_4$, filtered and was concentrated in vacuo. Silica gel chromatography using a hexanes/EtOAc gradient (0-100%) afforded the title product. $^1$H NMR (500 MHz, CDOD$_3$): δ 8.93 (1H, s), 7.68 (1H, s), 4.84 (1H, m), 4.15 (3H, s), 3.48 (2H, m), 2.91 (2H, m), 1.89 (3H, s), 1.56 (6H, dd, J=6.6, 1.6 Hz), m/z=552.06 (M+1).

Using essentially the same procedures described in Examples 54-61, the following compounds in Table 6 were made.

TABLE 6

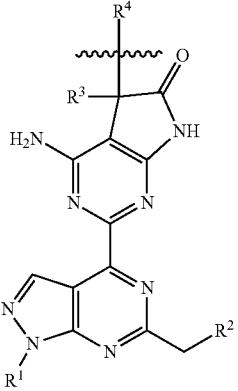

| EX. | Chirality Source or chiral resolution column | R¹ | R² | R³ | R⁴ | m/z (M + H) |
|---|---|---|---|---|---|---|
| 62 | Isomer A, Step A, Example 55 | CH₃ | CH₂CH₂CF₃ | cyclopropyl | 1-methyl-1,2,3-triazol-4-yl | 514 |
| 63 | IC column | CD₃ | CH₂CF₂CF₃ | Me | 1-(cyclopropylmethyl)-1,2,3-triazol-4-yl | 567.14 |
| 64 | OJ Column | CD₃ | CH₂CF₂CF₃ | Me | 1-ethyl-1,2,3-triazol-4-yl | 541.1 |
| 65 | AD Column | CH₃ | CH₂CF₂CF₃ | Me | 1-(cyclopropylmethyl)-1,2,3-triazol-4-yl | 564.15 |
| 66 | Isomer A, Step A, Example 58 | CH₃ | CH₂CF₂CF₃ | Et | 1-ethyl-1,2,3-triazol-4-yl | 552.12 |
| 67 | OD column | CD₃ | CH₂CF₂CF₃ | Me | 1-isopropyl-1,2,3-triazol-4-yl | 555.18 |

TABLE 6-continued

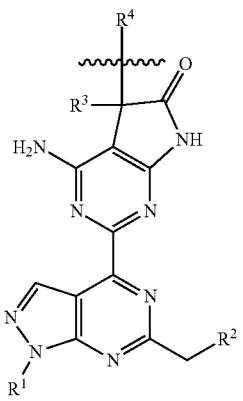

| EX. | Chirality Source or chiral resolution column | R¹ | R² | R³ | R⁴ | m/z (M + H) |
|---|---|---|---|---|---|---|
| 68 | Isomer A, Step A, Example 58 | $CH_3$ | $CH_2CF_2CF_3$ | Et | 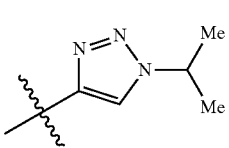 [SMILES: *c1cn(C(C)C)nn1] | 566.15 |
| 69 | Isomer A, Step A, Example 56 | $CH_3$ | $CH_2CF_2CF_3$ | Me | 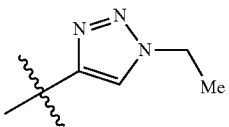 [SMILES: *c1cn(CC)nn1] | 538.02 |
| 70 | Isomer A, Step A, Example 56 | $CH_3$ | $CH_2CF_2CF_3$ | Me | 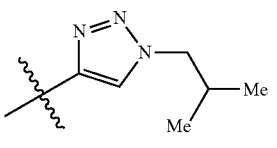 [SMILES: *c1cn(CC(C)C)nn1] | 566.15 |
| 71 | Isomer A, Step A, Example 56 | $CH_3$ | $CH_2CF_2CF_3$ | Me | 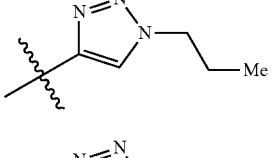 | 552.17 |
| 72 | Isomer A, Step A, Example 58 | $CH_3$ | $CH_2CF_2CF_3$ | Et | 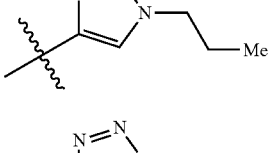 | 566.18 |
| 73 | Isomer A, Step A, Example 56 | $CH_3$ | $CH_2CF_2CF_3$ | Me | 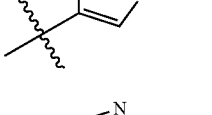 | 524.15 |
| 74 | Isomer A, Step A, Example 56 | $CH_3$ | $CH_2CF_2CF_3$ | Me | 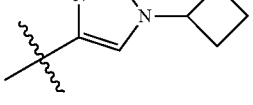 | 564.23 |
| 75 | Isomer A, Step A, Example 56 | $CH_3$ | $CH_2CF_2CF_3$ | Me | 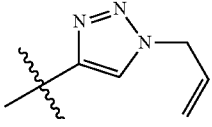 [SMILES: *c1cn(CC=C)nn1] | 550.20 |

TABLE 6-continued
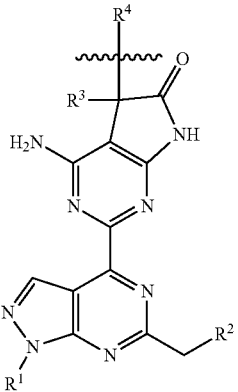
| EX. | Chirality Source or chiral resolution column | R$^1$ | R$^2$ | R$^3$ | R$^4$ | m/z (M + H) |
|---|---|---|---|---|---|---|
| 76 | Isomer A, Step A Example 57 | CD$_3$ | CH$_2$CF$_2$CF$_3$ | Me | triazole-N-CD$_3$ | 530.21 |
| 77 | Isomer A, Step A, Example 56 | CH$_3$ | CH$_2$CF$_2$CF$_3$ | Me | triazole-N-CD$_3$ | 527.23 |
| 78 | IC column | CH$_3$ | CH$_2$CH$_2$CF$_3$ | Me | triazole-N-CH(Me)$_2$ | 516.24 |
| 79 | Example 59 | CH$_3$ | CH$_2$CF$_2$CF$_3$ | Me | 2-CH$_2$Me triazole | 538.11 |
| 80 | Example 59 | CH$_3$ | CH$_2$CF$_2$CF$_3$ | Me | 2-Me triazole | 524.14 |

EXAMPLE 81

4-Amino-5-(1-isopropyl-1H-1,2,3-triazol-4-yl)-5-methyl-2-(1-methyl-6-(3,3,4,4,4-pentafluorobutyl)-1H-pyrazolo[3,4-d]pyrimidin-4-yl)-5,7-dihydro-6H-pyrrolo[2,3-d]pyrimidin-6-one

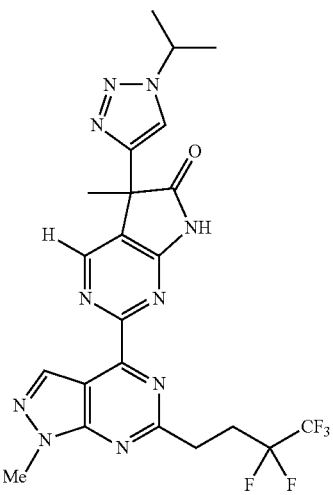 [SMILES: CC(C)n1cc(C2(C)C(=O)Nc3nc(-c4nc(CCC(F)(F)C(F)(F)F)nc5c4cnn5C)ncc32)nn1]

A mixture of the product of Example 56 (51 mg, 0.092 mmol) and t-butyl nitrite (0.08 mL, 0.65 mmol) was stirred at 60° C. for 20 min. The mixture was then cooled to RT and diluted with EtOAc and water. The organic layer was dried (magnesium sulfate), filtered and concentrated in vacuo. The material was purified by prep-TLC using 1:2 Hexanes:EtOAc gradient to afford the title product. $^1$H NMR δ (ppm)(DMSO-$d_6$): 12.00 (1H, s), 8.75 (1H, s), 8.73 (1H, s), 8.30 (1H, s), 4.77-4.81 (1H, m), 4.09 (3H, s), 3.39 (2H, t, J=7.88 Hz), 2.87-2.95 (2H, m), 1.83 (3H, s), 1.48 (6H, dd, J=6.73, 1.94 Hz).

EXAMPLE 82

Ethyl 3-(2-(4-amino-5-cyclopropyl-2-(1-(methyl-d3)-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidin-5-yl)thiazol-4-yl)-2,2-dimethylpropanoate and the S and R analogs thereof

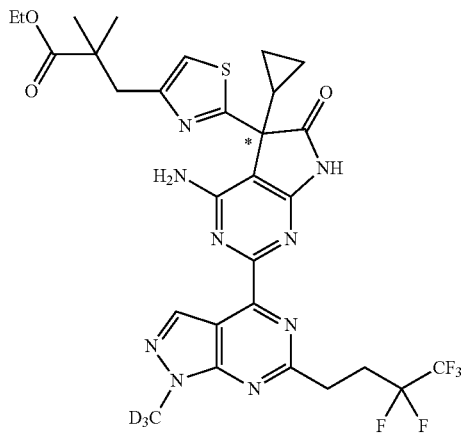 [SMILES: [2H]C([2H])([2H])n1ncc2c(-c3nc(N)c4c(n3)NC(=O)C4(c3nc(CC(C)(C)C(=O)OCC)cs3)C3CC3)nc(CCC(F)(F)C(F)(F)F)nc21]

Step A

4-Amino-5-cyclopropyl-2-(6-(3,3,4,4,4-pentafluorobutyl)-1-(methyl-d3)-1H-pyrazolo[3,4-d]pyrimidin-4-yl)-6-oxo-6,7-dihydro-5H-pyrrolo[2,3-d]pyrimidine-5-carboxamide Intermediate from Step A of Example 38 (330 mg, 0.607 mmol) was dissolved in 7M ammonia in MeOH (4.3 mL) and heated at 70° C. in a sealed tube for 3 h. The MeOH/NH$_3$ was removed under reduced pressure and the resulting material was suspended in DCM and purified by silica chromatography (0-7% MeOH in DCM gradient) to afford the title product.

Step B

4-Amino-5-cyclopropyl-2-(6-(3,3,4,4,4-pentafluorobutyl)-1-(methyl-d3)-1H-pyrazolo[3,4-d]pyrimidin-4-yl)-6-oxo-6,7-dihydro-5H-pyrrolo[2,3-d]pyrimidine-5-carbothioamide The intermediate from Step A (225 mg, 0.43 mmol, Example 54) and Lawesson's reagent (177 mg, 0.43 mmol) were stirred in 1,4-dioxane (3 mL) at 80° C. for 18 h. Water (3 mL) was then added and the reaction mixture was stirred at 80° C. for an additional 30 min. The reaction mixture was cooled to RT and concentrated in vacuo. The resulting material was dissolved in EtOAc and washed with saturated aq. NaHCO$_3$. The organic layer was dried over MgSO$_4$, filtered, and concentrated in vacuo. The residue was purified by silica gel chromatography using a DCM/MeOH gradient to give the title product.

Step C

Ethyl 3-(2-(4-amino-5-cyclopropyl-2-(1-(methyl-d3)-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidin-5-yl)thiazol-4-yl)-2,2-dimethylpropanoate To the intermediate from Step B (90 mg, 0.17 mmol) in EtOH (2 mL) was added ethyl 5-bromo-2,2-dimethyl-4-oxopentanoate (63 mg, 0.25 mmol). The solution was stirred at 80° C. for 18 h. The reaction mixture was cooled to RT and concentrated in vacuo. The resulting material was resolved using SFC (IC column) to provide isomer 82A (faster eluting) and isomer 82B (slower eluting) of the title compound. m/z=683.50 (M+1).

EXAMPLE 83

3-(2-(4-Amino-5-cyclopropyl-2-(1-(methyl-d3)-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidin-5-yl)thiazol-4-yl)-2,2-dimethylpropanoic acid

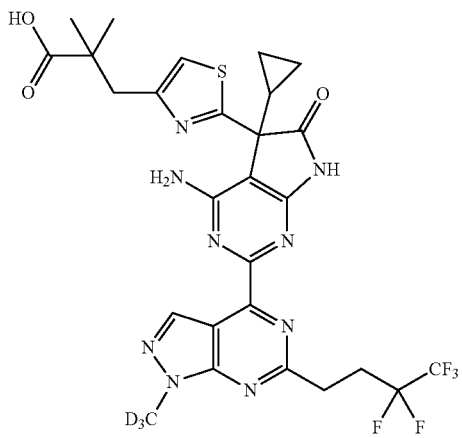 [SMILES: [2H]C([2H])([2H])n1ncc2c(-c3nc(N)c4c(n3)NC(=O)C4(c3nc(CC(C)(C)C(=O)O)cs3)C3CC3)nc(CCC(F)(F)C(F)(F)F)nc21]

To a solution of Isomer 82B from Example 82 (35 mg, 0.05 mmol) in THF was added 3M NaOH aq. solution (0.47 mL, 1.3 mmol) was added. The solution was heated to 50° C. for 96 h. 1N HCl (4 mL, 4 mmol) was added and the mixture was extracted with EtOAc. The organic layer was then dried with MgSO$_4$, filtered, and concentrated in vacuo. The crude product was purified by reverse phase HPLC using (water/acetonitrile, 0.1% TFA). The fractions were concentrated in vacuo and the aq. mixture was made basic with 1M K$_2$CO$_3$ aq. solution. The material was then extracted with EtOAc. The organic layer was washed with a 0.2% formic acid solution and brine, dried with MgSO$_4$, filtered, and concentrated in vacuo to afford the title compound. $^1$H NMR (500 MHz, DMSO-d$_6$) δ: 12.20 (1H, s), 11.62 (1H, s), 9.00 (1H, s), 7.36 (2H, s), 7.33 (1H, s), 3.38-3.31 (2H, m, partially overlapping with H$_2$O), 2.94 (2H, s), 2.92-2.82 (2H, m), 1.85-1.77 (1H, m), 1.12 (3H, s), 1.09 (3H, s), 0.67-0.62 (1H, m), 0.58-0.50 (2H, m), 0.46-0.38 (1H, m). m/z=655 (M+1).

EXAMPLE 84

4-Amino-5-methyl-2-(1-methyl-6-(3,3,4,4,4-pentafluorobutyl)-1H-pyrazolo[3,4-d]pyrimidin-4-yl)-5-(1H-tetrazol-1-yl)-5,7-dihydro-6H-pyrrolo[2,3-d]pyrimidin-6-one

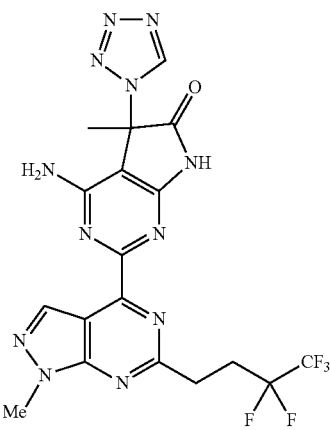 [SMILES: Cn1ncc2c(-c3nc(N)c4c(n3)NC(=O)C4(C)n3cnnn3)nc(CCC(F)(F)C(F)(F)F)nc21]

Step A

4-Amino-5-methyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidine-5-carbohydrazide The title compound was prepared using a procedure analogous to that described in Steps A-B from Example 38, starting from the ester intermediate prepared analogous to Step G of Example 1 from the intermediates from Step F of Example 1 and 1-14.

Step B

N-[4-Amino-5-methyl-2-[1-methyl-6-(3,3,4,4,4-pentafluorobutyl)-1H-pyrazolo[3,4-d]pyrimidin-4-yl]-6-oxo-5H,6H,7H-pyrrolo[2,3-d]pyrimidin-5-yl] carbamate and the S and R analogs thereof Into a 100-mL 3-necked round-bottom flask purged and maintained with an inert atmosphere of nitrogen, were added the intermediate from Step A (2.0 g, 4.0 mmol, 1.0 equiv), THF (40 mL) and TFA (0.52 g, 4.64 mmol, 1.15 equiv). This was followed by the addition of t-butyl nitrite (1.2 g, 11.99 mmol, 3.0 equiv) dropwise while stirring at 0° C. The resulting solution was stirred for 1 h at 0° C., and then concentrated in vacuo. To this was added t-BuOH (40 mL). The resulting solution was allowed to react, with stirring for additional 1 h while the temperature was maintained at 80° C. The reaction was then quenched by the addition of water (100 mL). The pH value of the solution was adjusted to a pH of 8 with NaHCO$_3$ (1 N). The resulting solution was extracted with EtOAc (4×100 mL) and the organic layers were combined, washed with brine (100 mL), dried over anhydrous sodium sulfate and filtered. The filtrate was concentrated in vacuo to dryness. The residue was applied onto a silica gel column with MeOH/DCM (2% to 5%). The crude was washed with DCM/MeOH (3×3 mL) in a ratio of 10/1 to afford the title product. The compounds were resolved via chiral SFC (IA column) to afford Isomer A (faster eluting) and Isomer B (slower eluting) of the title compound.

Step C 4,5-diamino-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one Isomer B from Step B (360 mg, 0.65 mmol, 1.00 equiv) and DCM (5 mL) were combined in a flask followed by the addition of TFA (2.5 mL). The resulting solution was stirred for 3 h at RT. The resulting mixture was concentrated in vacuo. The pH value of the solution was adjusted to a pH of 8 with NaHCO$_3$ (sat.). The resulting solution was extracted with EtOAc (3×50 mL) and the organic layers were combined. The resulting mixture was washed with brine (50 mL), dried over anhydrous sodium sulfate and filtered. The filtrate was concentrated in vacuo to dryness to afford the title product.

Step C

4-Amino-5-methyl-2-(1-methyl-6-(3,3,4,4,4-pentafluorobutyl)-1H-pyrazolo[3,4-d]pyrimidin-4-yl)-5-(1H-tetrazol-1-yl)-5,7-dihydro-6H-pyrrolo[2,3-d]pyrimidin-6-one Into a 5-mL microwave vial were placed the intermediate from the previous step (50 mg, 0.113 mmol, 1.0 equiv), sodium azide (11 mg, 0.17 mmol, 1.5 equiv), triethoxymethane (26 mg, 0.17 mmol, 1.5 equiv), and AcOH (2.5 mL). The resulting mixture was stirred for 30 min at 80° C. The reaction was quenched by the addition of water/ice (50 mL) and the pH was adjusted to pH of 9 with sat'd NaHCO₃. The resulting solution was extracted with EtOAc (3×50 mL) and the combined organic layers were washed with brine (50 mL), dried over anhydrous sodium sulfate, and filtered. The residue was purified by preparative TLC (DCM/MeOH=20/1). The crude product was purified by reverse phase HPLC (MeCN/Water, 0.05% TFA modifier). The mixture was conc. in vacuo, and sodium carbonate (1 mol/L) was added to adjust the pH to 10. The resulting solution was extracted with 3×50 mL of EtOAc and the organic layers were combined, dried over anhydrous sodium sulfate and filtered. The crude product was re-crystallized from hexane/EtOAc in a ratio of 5/1 to give the title compound: 1H-NMR (CD₃OD, 300 MHz, ppm) δ 9.54 (s, 1H), 8.92 (s, 1H), 4.14 (s, 3H), 3.51-3.45 (m, 2H), 2.99-2.81 (m, 2H), 2.25 (s, 3H); MS (ES, m/z) 511 [M+1]⁺.

EXAMPLE 85

4-Amino-5-(5-fluoropyridin-2-yl)-5,7'-dimethyl-2'-(3,3,4,4,4-pentafluorobutyl)-5,7-dihydro-6H,7'H-[2,4'-bipyrrolo[2,3-d]pyrimidin]-6-one

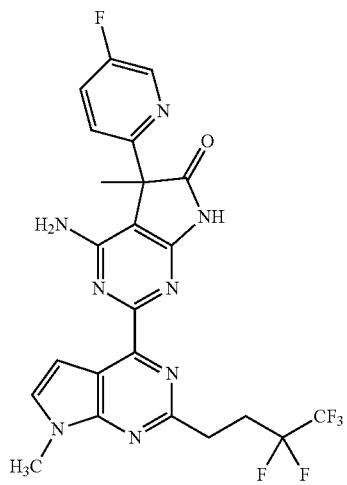 [SMILES: Cn1ccc2c(-c3nc(N)c4c(n3)NC(=O)C4(C)c3ccc(F)cn3)nc(CCC(F)(F)C(F)(F)F)nc21]

Step A 4,4,5,5,5-pentafluoropentanimidamide

Trimethyl aluminum (2.0 M toluene, 32.5 mL, 65.1 mmol) was added to ammonium chloride (3.48 g, 65.1 mmol) suspended in toluene (100 mL) at 0° C. The solution was then stirred at RT for 1 h to give a 0.49 M amino(chloro)methylaluminum solution in toluene. 4,4,5,5,5-Pentafluoropentanoic acid (2.5 g, 13.0 mmol), as described in Step A of Example 1, was added and the resulting mixture was left stirring at 100° C. for 18 h. The reaction mixture was cooled to RT and quenched with silica-gel and 1:1 MeOH-chloroform (50 mL). The resulting slurry was stirred vigorously for 30 min. The reaction mixture was filtered through a silica gel pad and washed with MeOH. The filtrate was concentrated. The crude product was purified by silica gel chromatography using MeOH (with 2M NH₃)/DCM gradient to give the title compound.

Step B 6-amino-5-(2,2-diethoxyethyl)-2-(3,3,4,4,4-pentafluorobutyl)pyrimidin-4-ol A mixture of the intermediate from Step A (1.01 g, 5.29 mmol) and NaOEt (0.72 g, 10.6 mmol) in EtOH (20 mL) was stirred at RT for 20 min. A solution of ethyl 2-cyano-4,4-diethoxybutanoate (1.34 g, 5.8 mmol) in 20 mL of EtOH was added and the resulting mixture was refluxed for 18 h. The reaction mixture was cooled to RT, concentrated in vacuo and the residue was diluted with EtOAc. The solution was then washed with water, dried over MgSO₄, filtered, and concentrated in vacuo. The crude product was purified by silica gel chromatography using MeOH (with 2M NH₃)/DCM gradient to give the title compound.

Step C 2-(3,3,4,4,4-pentafluorobutyl)-7H-pyrrolo[2,3-d]pyrimidin-4-ol

To a solution of the intermediate from Step B (1.170 g, 3.13 mmol) in 50 mL of EtOH was added TFA dropwise. The resulting mixture was stirred at RT for 18 h and concentrated in vacuo to give the title compound which was used in the next step without further purification.

Step D 4-chloro-2-(3,3,4,4,4-pentafluorobutyl)-7H-pyrrolo[2,3-d]pyrimidine

A solution of the intermediate from Step C (0.88 g, 3.1 mmol) in POCl₃ (10 mL) was refluxed for 3 h. The resulting mixture was concentrated in vacuo and the residue was diluted with diethyl ether, washed with water, dried over MgSO₄, filtered, and concentrated in vacuo. The crude product was purified by silica gel chromatography using hexanes/DCM gradient to give the title compound.

Step E 4-chloro-7-methyl-2-(3,3,4,4,4-pentafluorobutyl)-7H-pyrrolo[2,3-d]pyrimidine To a suspension of NaH (0.2 g, 5.0 mmol) in DMF (5 mL) at 0° C. was added a solution the intermediate from Step D (0.748 g, 2.5 mmol) in DMF (10 mL) dropwise. The reaction mixture was stirred at RT for 15 min and MeI (0.709 g, 5.0 mmol) was added. The resulting mixture was then stirred at RT for 1 h and partitioned between EtOAc and water. The organic phase was washed with brine, dried with MgSO₄, filtered, and concentrated in vacuo. The crude product was purified by silica gel chromatography using EtOAc/hexanes gradient to give the title compound.

Step F 7-methyl-2-(3,3,4,4,4-pentafluorobutyl)-7H-pyrrolo[2,3-d]pyrimidine-4-carbonitrile To a solution of the intermediate from Step E (0.681 g, 2.17 mmol) in DMF (10 mL) was added zinc cyanide (0.255 g, 2.17 mmol), Pd₂dba₃ (0.199 g, 0.217 mmol), and dppf (0.241 g, 0.434 mmol). The resulting solution was heated at 100° C. for 1 h. The reaction was cooled to RT, diluted with water (10 mL) and extracted with EtOAc. The organic phase was washed with brine, dried with MgSO₄, filtered, and concentrated in vacuo. The crude product was purified by silica gel chromatography using EtOAc/hexanes gradient to give the title compound.

Step G 7-methyl-2-(3,3,4,4,4-pentafluorobutyl)-7H-pyrrolo[2,3-d]pyrimidine-4-carboximidamide Trimethylaluminum (2.0 M in toluene, 18.9 mL, 37.8 mmol) was added dropwise to a suspension of ammonium chloride (2.02 g, 37.8 mmol) in 55 mL toluene cooled to 0° C. The solution was then stirred at RT for 1 h to give a 0.51 M amino(chloro)methylaluminum solution in toluene. This solution (27.9 mL, 14.2 mmol) was then added to the intermediate from Step F (0.541 g, 1.8 mmol) and then heated at 100° C. for 18 h. The reaction mixture was cooled to RT and quenched with silica-gel and 1:1 MeOH-chloroform (25 mL). The resulting slurry was stirred vigorously for 30 min. The reaction mixture was filtered through a silica gel pad (1") and washed with MeOH. The filtrate was concentrated in vacuo to yield the title compound.

Step H

4-Amino-5-(5-fluoropyridin-2-yl)-5,7'-dimethyl-2'-(3,3,4,4,4-pentafluorobutyl)-5,7-dihydro-6H,7'H-[2,4'-bipyrrolo[2,3-d]pyrimidin]-6-one A t-BuOH (1.5 mL) solution containing the intermediate from Step G (35 mg, 109 mmol), I-2B (56.9 mg, 0.22 mmol) and potassium bicarbonate (22 mg, 0.62 mmol) was heated at 80° C. in a sealed tube for 24 h. The reaction was cooled to RT, concentrated and purified via silica chromatography using a EtOAc gradient in hexanes to give the title product.
¹H NMR δ (500 MHz, DMSO-d₆): δ 11.24 (1H, s), 7.63 (1H, d, J=3.48 Hz), 7.36-7.28 (3H, m), 7.17 (1H, t, J=8.75 Hz), 6.66 (2H, s), 3.84 (3H, s), 3.35-3.28 (2H, partially overlapping with H₂O), 2.91-2.78 (2H, m), 1.80 (3H, s).

EXAMPLE 86

4-Amino-5-(5-cyclopropyl-1,3,4-oxadiazol-2-yl)-5,7'-dimethyl-2'-(3,3,4,4,4-pentafluorobutyl)-5,7-dihydro-6H,7'H-[2,4'-bipyrrolo[2,3-d]pyrimidin]-6-one

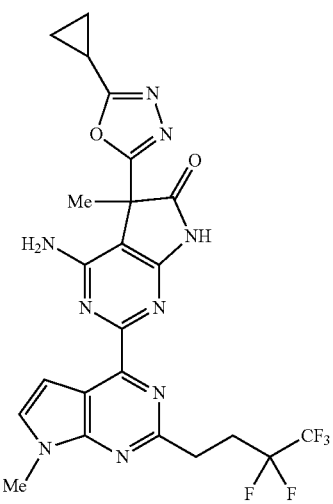 [SMILES: Cn1ccc2c(-c3nc(N)c4c(n3)NC(=O)C4(C)c3nnc(C4CC4)o3)nc(CCC(F)(F)C(F)(F)F)nc21]

Into an 8-mL vial, were placed the intermediate from Step G of Example 85 (52 mg, 0.16 mmol, 1.0 equiv), I-10B (38 mg, 0.14 mmol, 1.0 equiv), potassium bicarbonate (16 mg, 0.16 mmol, 1.0 equiv) and tert-butanol (2 mL). The resulting mixture was stirred for 16 h at 70° C. in an oil bath. The reaction mixture was cooled to RT and quenched by the addition of water (60 mL). The resulting solution was extracted with EtOAc (3×40 mL) and the organic layers were combined. The resulting mixture was washed with brine (50 mL), dried over anhydrous sodium sulfate and filtered. The filtrate was concentrated in vacuo to dryness. The residue was applied onto a silica gel column with EtOAc/petroleum ether (70%-80%) to give the title product.
¹H NMR (300 MHz, CDCl₃) δ 9.13 (s, 1H), 7.30-7.23 (m, 2H), 5.82 (brs, 2H), 3.92-3.87 (s, 3H), 3.59-3.49 (m, 2H), 2.91-2.60 (m, 2H), 2.16-2.06 (m, 1H), 1.98 (s, 3H), 1.20-1.11 (m, 4H); MS (ES, m/z) 550 [M+H]+.

Using essentially the same procedures described in Examples 86 or steps A through D of Example 38, the following compounds in Table 7 were made.

TABLE 7

| Ex. | Chirality Source or chiral resolution column | R³ | R⁶ | m/z (M + H) |
|---|---|---|---|---|
| 87 | I-9A | Me | Me | 523.9 |
| 88 | Chiralpak IB-3 column | ◁ | ◁ | 576.4 |

BIOLOGICAL ASSAY 1

Cell-based sGC Functional Assay (CASA Assay)
Rationale sGC is a heme-containing enzyme that converts GTP to secondary messenger cGMP. Increases in cGMP levels affect several physiological processes including vasorelaxation through multiple downstream pathways. The rate by which sGC catalyzes cGMP formation is greatly increased by NO and by recently discovered NO-independent activators and stimulators. Heme-dependent activators (HDAs) preferentially activate sGC containing a ferrous heme group. To determine the effect of sGC activators on enzyme activity, the CASA assay was developed to monitor the generation of cGMP in a cell line that stably expresses the heterodimeric sGC protein.

Methods

A CHO-K1 cell line stably expressing the sGC α1/β1 heterodimer was generated using a standard transfection protocol. CHO-K1 cells were transfected with plasmids pIREShyghsGCα1 and pIRESneo-hsGCβ1 simultaneously using FUGENE reagent. Clones that stably express both subunits were selected with hygromycin and neomycin for ~2 weeks. Clone #7 was chosen for the assay and was designated CHO-K1/sGC. CHO-K1/sGC cells were maintained in F-K12 medium containing 10% heat-inactivated Fetal Bovine Serum (FBS), 100 μg/mL penicillin/streptomycin, 0.5 mg/mL hygromycin and 0.25 mg/mL G418. The cells were then cryopreserved in LN2. On the day of the assay, cells thawed and resuspended in EBSS Assay Buffer (EAB, Sigma, E3024) supplemented with 5 mM $MgCl_2$, 10 mM HEPES (4-(2-hydroxyethyl)piperazine-1-ethanesulfonic acid) and 0.05% BSA (bovine serum albumin) and cell density was then adjusted to $4 \times 10^5$/mL with EAB. IBMX (3-isobutyl-1-methylxanthin, 0.5 mM) was added to inhibit degradation of cGMP. Compounds were diluted from DMSO stock solutions and added to the assay at a final DMSO concentration of 2.5%. Cells were incubated with compounds in the presence and absence of 1 μM of Diethylenetriamine/nitric oxide adduct (DETA-NO; Sigma, 17018) for 1 hr at 37° C. At the end of the incubation period, the reaction was terminated and the cells were lysed with the detection reagents from Cisbio Kits. The level of intracellular cGMP was determined using an HTRF-based assay kit (CisBio, 62GM2PEC), which detects the displacement of a fluorescence labeled cGMP from its specific antibody. The cGMP produced by test compounds was directly compared to the maximum cGMP production (this value was set to equal 100% activation.) of the published sGC-HDA Compound A:

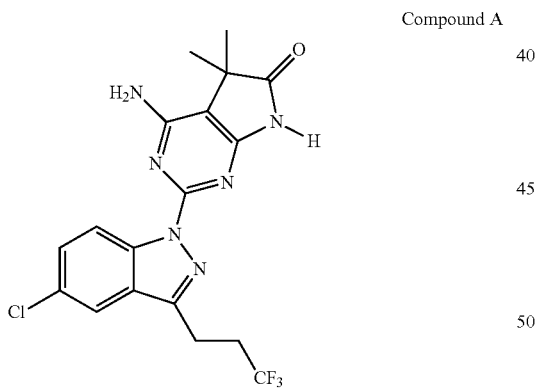

Compound A (Example 1 in WO 2010/065275, published Jun. 10, 2010). The test compounds' activity were then expressed as a percentage of Compound A, the standard in every experiment. This percent activation was calculated either in the presence or absence of DETA-NO which was then plotted. IP and maximum fold induction was derived using ADA analysis software for 4P fit.

The compounds in the Examples of the instant invention had inflection points (IP) less than or equal to 10 μM and more particularly less than or equal to about 1 μM. Most preferred compounds had an IP of less than or equal to about 500 nM. Data for the compounds of the Examples is provided in Table 8.

TABLE 8

| EX. | IP (nM) | % Act. |
|---|---|---|
| 1 | 55 | 123 |
| 2 | 72 | 135 |
| 3 | 104 | 117 |
| 4 | 54 | 115 |
| 5 | 10 | 88 |
| 6 | 604 | 137 |
| 7 | 212 | 147 |
| 8 | 49 | 126 |
| 9 | 116 | 121 |
| 10 | 665 | 114 |
| 11 | 626 | 126 |
| 12 | — | 104 |
| 13 | 29 | 89 |
| 14 | 709 | 131 |
| 15 | 475 | 100 |
| 16 | 160 | 107 |
| 17 | 122 | 116 |
| 18 | 411 | 88 |
| 19 | 225 | 157 |
| 20 | 103 | 132 |
| 21 | 138 | 111 |
| 22 | 71 | 103 |
| 23 | 435 | 88 |
| 24 | 885 | 84 |
| 25 | 991 | 93 |
| 26 | 230 | 72 |
| 27 | 208 | 89 |
| 28 | 891 | 126 |
| 29 | 230 | 121 |
| 30 | 35 | 98 |
| 31 | 44 | 169 |
| 32 | 59 | 113 |
| 33 | 32 | 104 |
| 34 | 44 | 109 |
| 35 | 96 | 88 |
| 36 | 43 | 116 |
| 37 | 41 | 192 |
| 38 | 265 | 165 |
| 39 | 150 | 115 |
| 40A | 371 | 89 |
| 40B | 292 | 68 |
| 42 | 887 | 120 |
| 43 | 825 | 143 |
| 44 | 225 | 113 |
| 45 | 738 | 101 |
| 46 | 258 | 97 |
| 47 | 2076 | 108 |
| 48 | 399 | 112 |
| 49 | 149 | 113 |
| 50 | 84 | 176 |
| 51 | 119 | 154 |
| 52 | 90 | 148 |
| 53 | 280 | 165 |
| 54 | 229 | 93 |
| 55 | 251 | 118 |
| 56 | 1017 | 126 |
| 57 | 147 | 125 |
| 58 | 713 | 105 |
| 59 | 29 | 117 |
| 60 | 933 | 136 |
| 61 | 269 | 110 |
| 62 | 800 | 99 |
| 63 | 235 | 93 |
| 64 | 114 | 120 |
| 65 | 169 | 111 |
| 66 | 327 | 108 |
| 67 | 120 | 128 |
| 68 | 811 | 133 |
| 69 | 259 | 105 |
| 70 | 294 | 132 |
| 71 | 217 | 169 |
| 72 | 503 | 121 |
| 73 | 416 | 117 |
| 74 | 78 | 120 |
| 75 | 175 | 139 |
| 76 | 168 | 148 |
| 77 | 168 | 157 |
| 78 | 368 | 103 |

TABLE 8-continued

| EX. | IP (nM) | % Act. |
|---|---|---|
| 79 | 491 | 169 |
| 80 | 408 | 90 |
| 81 | 620 | 102 |
| 82 | 509 | 78 |
| 83 | 797 | 80 |
| 84 | 365 | 111 |
| 85 | 112 | 108 |
| 86 | 410 | 104 |
| 87 | 378 | 86 |
| 88 | 715 | 109 |

Acute Efficacy in Spontaneously Hypertensive Rats (SHR)

Spontaneously hypertensive rats (SHR, male, Charles River) were implanted with DSI TA11PA-C40 telemetry device (Data Sciences, Inc., St. Paul, Minn.) under isoflurane or ketamine/metomidine anesthesia. The telemetry unit catheter was inserted into the descending aorta via the femoral artery and the telemetry device was implanted subcutaneously in the left flank area. Animals were allowed to recover from surgery for 14 days before the start of any studies. Blood pressure, heart rate, and activity signals from conscious, freely moving rats were recorded continuously for 30 seconds every 10 min. On the day prior to administration of compound, a single oral dose of vehicle (10% transcutol/20% Cremophor/70% water) was administered to all animals to establish baseline control data. The blood pressure lowering efficacy of compound (PO) or vehicle was evaluated following a single oral gavage. Data were collected as hourly averages, and changes in blood pressure were calculated by subtracting control baseline data on an hourly basis. Animals were maintained on normal diet with a 12 hour light-dark cycle.

Maximum peak decreases of systolic blood pressure (SBP) in SHR at a particular P.O. dose (mpk milligrams per kilogram) for the following representative compounds are provided in Table 9. Category A=SBP in SHRs <15 mmHg; Category B=SBP in SHRs 15-25 mmHg; Category C=SBP in SHRs >25 mmHg

TABLE 9

| EX. | Dose, P.O. mpk | Category |
|---|---|---|
| 1 | 0.3 | C |
| 3 | 0.3 | C |
| 4 | 0.3 | B |
| 19 | 1 | C |
| 25 | 3 | C |
| 40 | 1 | C |
| 38 | 1 | C |
| 44 | 1 | B |
| 54 | 1 | B |
| 55 | 1 | B |
| 56 | 1 | C |
| 63 | 1 | A |
| 66 | 1 | B |
| 67 | 0.3 | B |
| 69 | 1 | C |
| 78 | 1 | C |
| 84 | 1 | A |
| 86 | 1 | B |

What is claimed is:

1. A compound having structural Formula I, or a pharmaceutically acceptable salt thereof:

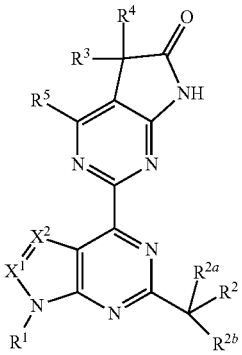

or a pharmaceutically acceptable salt thereof wherein:
$X^1$ and $X^2$ are each independently CR or N;
R is —H, halo or cyclopropyl;
$R^1$ is —H or —$C_{1-6}$alkyl unsubstituted or substituted with one to three of —F;
$R^2$ is (a) —$C_{1-6}$alkyl unsubstituted or substituted with:
  (i) one to six of —F,
  (ii) —$C_{3-6}$cycloalkyl unsubstituted or substituted with one to three of —F, or
  (iii) phenyl unsubstituted or independently substituted at each occurrence with one to three of halo, —CN, —$CH_3$ or —$OCH_3$;
  (b) —$C_{3-6}$cycloalkyl unsubstituted or substituted with one to three of —F, or
(c) phenyl unsubstituted or independently substituted at each occurrence with one to three of halo, —CN, —$CH_3$ or —$OCH_3$;
$R^{2a}$ is —H or —$C_{1-3}$alkyl unsubstituted or substituted with one to three of —F;
$R^{2b}$ is —H or —$C_{1-2}$ alkyl unsubstituted or substituted with one to three of —F;
or $R^{2b}$ is —H and $R^2$ and $R^{2a}$ are joined together with the carbon to which they are both attached to represent
  (a) —$C_{3-6}$cycloalkyl unsubstituted or substituted with one to three of —F, or
  (b) a 4 to 6 membered heterocycle comprised of carbons and one or two heteroatoms independently selected from N, O or S, wherein the heterocycle is unsubstituted or independently substituted at each occurrence with one to three of halo, —CN, —$CH_3$ or —$OCH_3$;
$R^3$ is —$C_{1-6}$alkyl or —$C_{3-6}$cycloalkyl;
$R^4$ is
  (a) a 5-membered heteroaryl ring comprised of at least one and up to three carbon atoms, at least one and up to four N atoms, and optionally one O atom or one S atom;
  (b) a 6-membered heteroaryl ring comprised of carbon atoms and one or two N atoms; or
  (c) an 8 to 10 membered bicyclic heteroaryl ring system comprised of carbon atoms and one to two heteroatoms independently selected from N, O or S;
wherein $R^4$ is unsubstituted or substituted on an available carbon or nitrogen in the ring or ring system with $R^6$;
$R^6$ is selected from:
  (a) halo,
  (b) —$C_{1-6}$alkyl unsubstituted or substituted with one to three of —F, or —$C_{3-6}$ cycloalkyl for example but not limited to:

[Structure: cyclopropylmethyl group] or [Structure: 1-cyclopropylethyl group], (c) —$C_{1-6}$alkyl substituted with —$C_{3-6}$ cycloalkyl, such that the cycloalkyl and the alkyl share a common carbon at the point of attachment to each other, wherein said attachment can be with any non-terminal carbon in the alkyl group, for example but not limited to:

[Structure: 1-methylcyclopropyl-methyl]

(d) —$C_{3-6}$ cycloalkyl,
(e) —$OC_{1-6}$alkyl,
(f) —$C_{2-6}$alkenyl,
(g) —C(O)O$C_{1-4}$alkyl,
(h) —$C_{1-6}$alkyl-C(O)OH,
(i) —$C_{1-6}$alkyl-C(O)O$C_{1-3}$alkyl, or
(j) -$CD_3$;

$R^5$ is —H, —$OR^7$ or —$NHR^7$; and
$R^7$ is —H, —$C_{1-6}$alkyl or —$C_{3-6}$ cycloalkyl.

2. The compound of claim 1 or a pharmaceutically acceptable salt thereof wherein: $X^1$ and $X^2$ are each independently CH or N,
$R^1$ is —H or —$C_{1-3}$alkyl;
$R^3$ is —$C_{1-6}$alkyl or —$C_{3-6}$cycloalkyl; and
$R^5$ is —H, —OH or —$NH_2$.

3. The compound according to claim 1 or a pharmaceutically acceptable salt thereof wherein $R^2$ is:
(a) —$C_{1-6}$alkyl substituted with
  (i) one to six of —F,
  (ii) —$C_{3-6}$cycloalkyl substituted with one to three of —F; or
  (iii) phenyl independently substituted at each occurrence with one to three of halo, —CN, —$CH_3$ or —$OCH_3$,
(b) —$C_{3-6}$cycloalkyl substituted with one to three of —F, or
(c) phenyl independently substituted at each occurrence with one to three of -halo, —CN, —$CH_3$ or —$OCH_3$.

4. The compound according to claim 1 or a pharmaceutically acceptable salt thereof wherein $R^3$ is —$C_{1-3}$alkyl or cyclopropyl.

5. The compound according to claim 1 or a pharmaceutically acceptable salt thereof wherein $R^4$ is a 5-membered heteroaryl ring selected from:

[Structures: various 5-membered heteroaryl rings with $R^{6a}$ substituents — oxadiazoles, oxazoles, isoxazole, pyrazole, triazoles, tetrazoles, thiadiazole, thiazole, oxazole]

and $R^{6a}$ is —H or $R^6$.

6. The compound according to claim 1 or a pharmaceutically acceptable salt thereof wherein $R^4$ is

[Structures: pyridine or 6-membered heteroaryl with $X^3$–$X^7$ and $R^{6a}$]

wherein one of $X^3$, $X^4$, $X^5$, $X^6$ or $X^7$ is N and the others are CH; and $R^{6a}$ is —H or $R^6$.

7. The compound according to claim 1 or a pharmaceutically acceptable salt thereof wherein $R^4$ is

[Structures: fused bicyclic heteroaryl with $X^8$–$X^{11}$ or benzodioxane]

wherein one or two of $X^8$, $X^9$, $X^{10}$ or $X^{11}$ is N and the others are CH.

8. The compound of claim 1 or a pharmaceutically acceptable salt thereof wherein $R^5$ is —H, —OH or —$NH_2$.

9. The compound of claim 1 or a pharmaceutically acceptable salt thereof wherein $R^6$ is: (a) —F or —Cl, (b) —$C_{1-6}$alkyl, (c) —$CF_3$, (d) —$CH_2$—$C_{3-6}$cycloalkyl, (e) —$C_{1-3}$alkyl substituted with —$C_{3-4}$ cycloalkyl such that the cycloalkyl and the alkyl share a common carbon at the point of attachment to each other, (f) —$C_{3-6}$cycloalkyl, (g) —$OC_{1-6}$alkyl, (h) —$C_{2-4}$alkenyl, (i) —C(O)O$C_{1-4}$alkyl, (j) —$C_{1-4}$alkyl-C(O)OH, (k) —$C_{1-4}$alkyl-C(O)O$CH_3$, or (l) -$CD_3$.

10. The compound of claim 1 having the structural Formula Ia, or a pharmaceutically acceptable salt thereof:

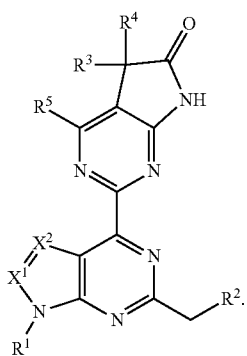

11. The compound of claim 1, having the structural Formula Ib or a pharmaceutically acceptable salt thereof:

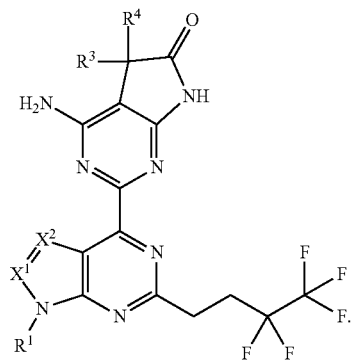

12. The compound of claim 1, which is:
4-Amino-5-(5-fluoropyridin-2-yl)-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one;
4-Amino-2-(6-((3,3-difluorocyclobutyl)methyl)-1-methyl-1H-pyrazolo[3,4-d]pyrimidin-4-yl)-5-(5-fluoropyridin-2-yl)-5-methyl-5H-pyrrolo[2,3-d]pyrimidin-6(7H)-one;
4-Amino-5-(5-fluoropyridin-2-yl)-5-methyl-2-(1-methyl-6-(4,4,4-trifluorobutyl)-1H-pyrazolo[3,4-d]pyrimidin-4-yl)-5H-pyrrolo[2,3-d]pyrimidin-6(7H)-one;
4-Amino-5-methyl-5-(5-methyl-1,2,4-oxadiazol-3-yl)-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one;
4-Amino-5-cyclopropyl-5-(1-methyl-1H-tetrazol-5-yl)-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one;
4-Amino-5-cyclopropyl-5-(5-cyclopropyl-1,3,4-oxadiazol-2-yl)-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one;
4-Amino-5-cyclopropyl-5-(5-methyl-1,3,4-oxadiazol-2-yl)-2-(6-(3,3,4,4,4-pentafluorobutyl)-1-trideuteriomethyl-1H-pyrazolo[3,4-d]pyrimidin-4-yl)-5H-pyrrolo[2, 3-d]pyrimidin-6(7H)-one;
4-Amino-5-cyclopropyl-5-(5-cyclopropyl-1,3,4-oxadiazol-2-yl)-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one;
4-Amino-5-cyclopropyl-5-(1-methyl-1H-1,2,3-triazol-4-yl)-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one;
4-Amino-5-cyclopropyl-5-(1-methyl-1H-1,2,3-triazol-4-yl)-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one;
4-Amino-5-(1-isopropyl-1H-1,2,3-triazol-4-yl)-5-methyl-2-(1-methyl-6-(3,3,4,4,4-pentafluorobutyl)-1H-pyrazolo[3,4-d]pyrimidin-4-yl)-5H-pyrrolo[2, 3-d]pyrimidin-6(7H)-one;
4-Amino-5-(1-(cyclopropylmethyl)-1H-1,2,3-triazol-4-yl)-5-methyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one;
4-Amino-5-ethyl-5-(1-ethyl-1H-1,2,3-triazol-4-yl)-2-(1-methyl-6-(3,3,4,4,4-pentafluorobutyl)-1H-pyrazolo[3, 4-d]pyrimidin-4-yl)-5H-pyrrolo[2,3-d]pyrimidin-6 (71H)-one;
4-Amino-5-(1-isopropyl-1H-1,2,3-triazol-4-yl)-5-methyl-2-(6-(3,3,4,4,4-pentafluorobutyl)-1-trideuteriomethyl-1H-pyrazolo[3,4-d]pyrimidin-4-yl)-5H-pyrrolo[2,3d]pyrimidin-6(7H)-one;
4-Amino-5-(1-ethyl-1H-1,2,3-triazol-4-yl)-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6 (7H)-one;
4-Amino-5-(1-isopropyl-1H-1,2,3-triazol-4-yl)-5-methyl-2-(1-methyl-6-(4,4,4-trifluorobutyl)-1H-pyrazolo[3,4-d]pyrimidin-4-yl)-5H-pyrrolo[2,3-d]pyrimidin-6(7H)-one;
4-Amino-5-methyl-2-(1-methyl-6-(3,3,4,4, 4-pentafluorobutyl)-1H-pyrazolo[3,4-d]pyrimidin-4-yl)-5-(1H-tetrazol-1-yl)-5H-pyrrolo[2,3-d]pyrimidin-6(7H)-one;
4-Amino-5-(5-cyclopropyl-1,3,4-oxadiazol-2-yl)-5,7-dimethyl-2'-(3,3,4,4,4-pentafluorobutyl)-5H,7'H-[2,4'-bipyrrolo[2,3-d]pyrimidin-6(7H)-one;
or a pharmaceutically acceptable salt of each of the foregoing compounds.

13. The compound of claim 1 which is:
4-Amino-5-(5-fluoropyridin-2-yl)-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one;
4-Amino-2-(6-((3,3-difluorocyclobutyl)methyl)-1-methyl-1H-pyrazolo[3,4-d]pyrimidin-4-yl)-5-(5-fluoropyridin-2-yl)-5-methyl-5H-pyrrolo[2,3-d]pyrimidin-6(7H)-one;
4-Amino-5-(5-fluoropyridin-2-yl)-5-methyl-2-(1-methyl-6-(4,4,4-trifluorobutyl)-1H-pyrazolo[3,4-d]pyrimidin-4-yl)-5H-pyrrolo[2, 3-d]pyrimidin-6(7H)-one;
4-Amino-5-methyl-5-(5-methyl-1,2,4-oxadiazol-3-yl)-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one;
4-Amino-5-cyclopropyl-5-(1-methyl-1H-tetrazol-5-yl)-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one;
4-Amino-5-cyclopropyl-5-(5-cyclopropyl-1,3,4-oxadiazol-2-yl)-2-(6-(3,3,4,4,4-pentafluorobutyl)-1-trideuteriomethyl-1H-pyrazolo[3,4-d]pyrimidin-4-yl)-5H-pyrrolo[2, 3-d]pyrimidin-6(7H)-one;
4-Amino-5-cyclopropyl-5-(5-methyl-1,3,4-oxadiazol-2-yl)-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one;

4-Amino-5-cyclopropyl-5-(5-cyclopropyl-1,3,4-oxadi-azol-2-yl)-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one;

4-Amino-5-cyclopropyl-5-(1-methyl-1H-1,2,3-triazol-4-yl)-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one;

4-Amino-5-cyclopropyl-5-(1-methyl-1H-1,2,3-triazol-4-yl)-2-(1-methyl-6-(3,3,4,4,4-pentafluorobutyl)-1H-pyrazolo[3,4-d]pyrimidin-4-yl)-5H-pyrrolo[2, 3-d]pyrimidin-6(7H)-one;

4-Amino-5-(1-isopropyl-1H-1,2,3-triazol-4-yl)-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one;

4-Amino-5-(1-(cyclopropylmethyl)-1H-1,2,3-triazol-4-yl)-5-methyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one;

4-Amino-5-ethyl-5-(1-ethyl-1H-1,2,3-triazol-4-yl)-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one;

4-Amino-5-(1-isopropyl-1H-1,2,3-triazol-4-yl)-5-methyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one;

4-Amino-5-(1-ethyl-1H-1,2,3-triazol-4-yl)-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one;

4-Amino-5-(1-isopropyl-1H-1,2,3-triazol-4-yl)-5-methyl-2-(1-methyl-6-(4,4,4-trifluorobutyl)-1H-pyrazolo[3,4-d]pyrimidin-4-yl)-5H-pyrrolo[2,3-d]pyrimidin-6(7H)-one;

4-Amino-5-methyl-2-(1-methyl-6-(3,3,4,4,4-pentafluorobutyl)-1H-pyrazolo[3,4-d]pyrimidin-4-yl)-5-(1H-tetrazol-1-yl)-5H-pyrrolo[2,3-d]pyrimidin-6(7H)-one;

4-Amino-5-(5-cyclopropyl-1,3,4-oxadiazol-2-yl)-5,7'-dimethyl-2-(3,3,4,4,4-pentafluorobutyl)-5H,7'H-[2,4'-bipyrrolo[2,3-d]pyrimidin]-6(7H)-one;

or a pharmaceutically acceptable salt of each of the foregoing compounds.

14. The compound claim 1, which is 4-amino-5-(5-isopropyl-1,3,4-oxadiazolyl-2-yl)-5-methyl-2-(1-methyl-6-(3,3,4,4,4-pentafluorobutyl)-1H-pyrazolo[3,4-d]pyrimidine-4-yl)-5,7-dihydro-6H-pyrrolo[2,3-d]pyrimidin-6-one, or a pharmaceutically acceptable salt thereof.

15. A pharmaceutical composition comprising the compound of claim 1, or a pharmaceutically acceptable salt thereof and a pharmaceutically acceptable carrier.

16. The pharmaceutical composition of claim 15 further comprising one or more additional active agents selected from an angiotensin converting enzyme inhibitor, an angiotensin II receptor antagonist, a neutral endopeptidase inhibitor, an aldosterone antagonist, a renin inhibitor, an endothelin receptors antagonist, an aldosterone synthase inhibitor, a phosphodiesterase-5 inhibitor, a vasodilator, a calcium channel blocker, a potassium channel activator, a diuretic, a sympatholitic, a beta-adrenergic blocking drug, an alpha adrenergic blocking drug, a central alpha adrenergic agonist, a peripheral vasodilator, a lipid lowering agent or a metabolic altering agent.

17. A method for activating soluble guanylate cyclase comprising the step of administering an amount efficacious therefore of the compound of claim 1 or a pharmaceutically acceptable salt thereof.

18. A method for the treatment of one or more conditions selected from cardiovascular disease, endothelial dysfunction, diastolic dysfunction, atherosclerosis, hypertension, heart failure, pulmonary hypertension, angina pectoris, thrombosis, restenosis, myocardial infarction, stroke, cardiac insufficiency, pulmonary hypertonia, erectile dysfunction, asthma bronchiale, chronic kidney disease, diabetes or cirrhosis of the liver in a patient comprising administering a therapeutically effective amount of the compound of claim 1, or a pharmaceutically acceptable salt thereof, to a patient in need thereof.

19. A method for the treatment of hypertension comprising administering a therapeutically effective amount of the compound of claim 1, or a pharmaceutically acceptable salt thereof to a patient in need thereof.

20. A method for the treatment of heart failure comprising administering a therapeutically effective amount of the compound of claim 1, or a pharmaceutically acceptable salt thereof, to a patient in need thereof.

* * * * *